United States Patent
Hwang et al.

(10) Patent No.: US 10,043,980 B2
(45) Date of Patent: *Aug. 7, 2018

(54) COMPOUND AND ORGANIC LIGHT-EMITTING DEVICE INCLUDING THE SAME

(71) Applicant: SAMSUNG DISPLAY CO., LTD., Yongin-si, Gyeonggi-Do (KR)

(72) Inventors: Seokhwan Hwang, Yongin-si (KR); Jongwoo Kim, Yongin-si (KR); Youngkook Kim, Yongin-si (KR); Jino Lim, Yongin-si (KR)

(73) Assignee: Samsung Display Co., Ltd., Yongin-si, Gyeonggi-do (KR)

( * ) Notice: Subject to any disclaimer, the term of this patent is extended or adjusted under 35 U.S.C. 154(b) by 197 days.

This patent is subject to a terminal disclaimer.

(21) Appl. No.: 14/870,036

(22) Filed: Sep. 30, 2015

(65) Prior Publication Data

US 2016/0293847 A1   Oct. 6, 2016

(30) Foreign Application Priority Data

Mar. 30, 2015 (KR) ........................ 10-2015-0044395

(51) Int. Cl.

| | | |
|---|---|---|
| *H01L 51/00* | (2006.01) | |
| *H01L 27/32* | (2006.01) | |
| *C07D 409/04* | (2006.01) | |
| *C07D 307/77* | (2006.01) | |
| *C07D 307/91* | (2006.01) | |
| *C07D 409/10* | (2006.01) | |
| *C09K 11/06* | (2006.01) | |
| *H01L 51/50* | (2006.01) | |

(52) U.S. Cl.
CPC ........ *H01L 51/0061* (2013.01); *C07D 307/77* (2013.01); *C07D 307/91* (2013.01); *C07D 409/04* (2013.01); *C07D 409/10* (2013.01); *C09K 11/06* (2013.01); *H01L 27/3248* (2013.01); *H01L 51/006* (2013.01); *H01L 51/0052* (2013.01); *H01L 51/0058* (2013.01); *H01L 51/0059* (2013.01); *H01L 51/0073* (2013.01); *H01L 51/0074* (2013.01); *H01L 51/0077* (2013.01); *C09K 2211/1029* (2013.01); *C09K 2211/1033* (2013.01); *C09K 2211/1044* (2013.01); *C09K 2211/1088* (2013.01); *C09K 2211/1092* (2013.01); *C09K 2211/185* (2013.01); *H01L 51/506* (2013.01); *H01L 51/5012* (2013.01); *H01L 51/5056* (2013.01); *H01L 51/5072* (2013.01); *H01L 51/5076* (2013.01)

(58) Field of Classification Search
None
See application file for complete search history.

(56) References Cited

U.S. PATENT DOCUMENTS

| | | | |
|---|---|---|---|
| 4,720,432 A | 1/1988 | Vanslyke et al. | |
| 4,918,101 A | 4/1990 | Bair | |
| 5,061,569 A | 10/1991 | Vanslyke et al. | |
| 6,242,115 B1 | 6/2001 | Thomson et al. | |
| 7,507,485 B2 * | 3/2009 | Oh ........................ | H01L 51/006 313/504 |
| 2006/0020136 A1 | 1/2006 | Hwang et al. | |
| 2008/0124572 A1 | 5/2008 | Mizuki et al. | |
| 2013/0328021 A1 * | 12/2013 | Lim ....................... | C07C 211/54 257/40 |
| 2016/0155952 A1 * | 6/2016 | Hwang ................ | H01L 51/0061 257/40 |

FOREIGN PATENT DOCUMENTS

| | | |
|---|---|---|
| JP | 11-144873 A | 5/1999 |
| JP | 2000-302756 A | 10/2000 |
| JP | 2003-133075 A | 5/2003 |
| JP | 2004-079265 A | 3/2004 |
| JP | 2006-151979 A | 6/2006 |
| KR | 10-2014-0091487 A | 7/2014 |

OTHER PUBLICATIONS

Machine translation for KR 10-2014-091487 (publication date Jul. 2014).*
Extended European Search Report dated Dec. 21, 2015 in Corresponding European Patent Application No. 15193432.0.
GuideChem Image Phenanthro[4,5-bcd]furan-3-ol(7Cl,8Cl,9Cl), printed Jun. 3, 2015.
ChemSpider Image Phenanthro[4,5-bcd]furan-1-ol, printed Jun. 3, 2015.

* cited by examiner

*Primary Examiner* — Dawn L Garrett
(74) *Attorney, Agent, or Firm* — Lee & Morse, P.C.

(57) ABSTRACT

A compound, an organic light-emitting device including the compound, and a display apparatus including the organic light-emitting device, the compound being represented by the following Formula 1:

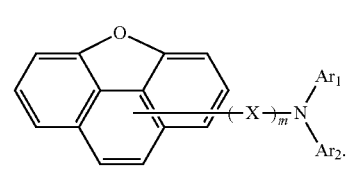

<Formula 1>

15 Claims, 1 Drawing Sheet

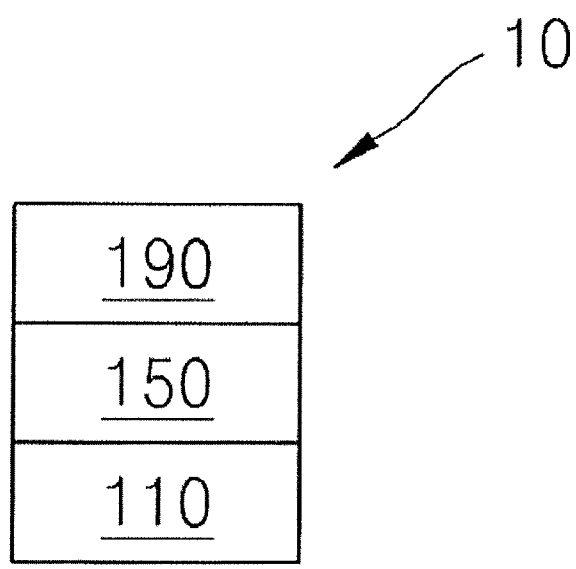

COMPOUND AND ORGANIC LIGHT-EMITTING DEVICE INCLUDING THE SAME

CROSS-REFERENCE TO RELATED APPLICATION

Korean Patent Application No. 10-2015-0044395, filed on Mar. 30, 2015, in the Korean Intellectual Property Office, and entitled: "Compound and Organic Light-Emitting Device Including the Same," is incorporated by reference herein in its entirety.

BACKGROUND

1. Field

Embodiments relate to a compound and an organic light-emitting device including the same.

2. Description of the Related Art

Organic light-emitting devices (OLEDs) are self-emitting devices that have wide viewing angles, high contrast ratios, and short response times. OLEDs also exhibit excellent brightness, driving voltage, and response speed characteristics, and produce multicolored images.

The OLED may include a first electrode disposed on a substrate, and a hole transport region, an emission layer, an electron transport region, and a second electrode, which are sequentially disposed on the first electrode. Holes provided from the first electrode move toward the emission layer through the hole transport region, and electrons provided from the second electrode move toward the emission layer through the electron transport region. Carriers, such as holes and electrons, are recombined in the emission layer to produce excitons. These excitons change from an excited state to a ground state, thereby generating light.

SUMMARY

Embodiments are directed to a compound and an organic light-emitting device including the same.

The embodiments may provide a compound as a hole transporting material having improved high efficiency, low driving voltage, high luminance, and long lifespan characteristics and an organic light-emitting device including the compound.

According to an embodiment, there is provided a compound represented by Formula 1:

<Formula 1>

In Formula 1, $Ar_1$ and $Ar_2$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, X may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, m may be an integer selected from 0 to 4, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_2$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and

—N($Q_{31}$)($Q_{32}$), wherein $Q_{11}$ to $Q_{17}$, $Q_{21}$ to $Q_{27}$, and $Q_{31}$ to $Q_{32}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and X may be identical to or different from each other, when m is 2, 3, or 4.

Another embodiment may provide a first electrode; a second electrode facing the first electrode; and an organic layer disposed between the first electrode and the second electrode and including an emission layer, wherein the organic layer includes the compound of Formula 1.

Another embodiment may provide a flat display apparatus including the organic light-emitting device of which the first electrode is electrically coupled to source and drain electrodes of a thin film transistor.

BRIEF DESCRIPTION OF THE DRAWING

Features will be apparent to those of skill in the art by describing in detail exemplary embodiments with reference to the attached drawing in which:

The FIGURE illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

There is provided a compound represented by Formula 1:

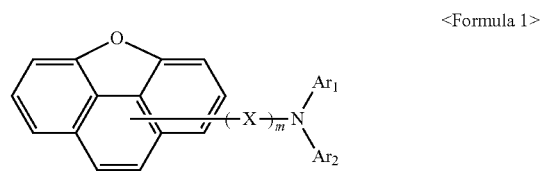

<Formula 1>

In Formula 1, $Ar_1$ and $Ar_2$ may each independently be selected from or include, e.g., a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

X may be selected from or include, e.g., a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

m may be an integer selected from 0 to 4, e.g., may be 0, 1, 2, 3, or 4.

In an implementation, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_2$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and

—N($Q_{31}$)($Q_{32}$), wherein $Q_{11}$ to $Q_{17}$, $Q_{21}$ to $Q_{27}$, and $Q_{31}$ to $Q_{32}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In ani implementation, X may be identical to or different from each other when m is 2 or more, e.g., 2, 3, or 4.

The compound represented by Formula 1 may have a high glass transition temperature (Tg) or a high melting point, e.g., due to the introduction or inclusion of the condensed ring. Thus, the compound of Formula 1 may have high heat resistance against Joule heat generated in an organic layer or between an organic layer and a metal electrode when light emission occurs. The compound of Formula 1 may also have high durability in a high-temperature environment. An organic light-emitting device including the compound of Formula 1 may have high durability when stored or operated.

In addition, the compound of Formula 1 may have a phenanthrofuran structure including a phenantrene moiety that is condensed in a molecule. In this regard, π-electrons of the compound of Formula 1 may be delocalized, and accordingly, unshared electron pairs of an oxygen atom may partially provide an extra electron.

In Formula 1, the phenanthrofuran group linked to amine via X may influence hole-transporting capabilities, and accordingly, the compound of Formula 1 may have an increased resistance against electrons provided from an emission layer.

The improvement in the hole-transporting capabilities may relate to improvement in lifespan of the molecule, and thus the compound of Formula 1 according to an embodiment may exhibit improved lifespan characteristics, compared to those of other arylamine derivatives.

In addition, due to the substitution of the phenanthrofuran group in a molecule, a state of a molecular film that is formed as a film is improved, and accordingly, the characteristics of the organic light-emitting device may be improved. In this regard, when the organic light-emitting device includes the compound of Formula 1 as a material for transporting a hole may result in long lifespan characteristics. Accordingly, the organic light-emitting device including the compound of Formula 1 according to an embodiment may be manufactured as a device having high efficiency, low driving voltage, high brightness, and long lifespan characteristics.

The substituents of Formula 1 will be described in more detail.

In an exemplary embodiment, in Formula 1, X may be or may include, e.g., a substituted or unsubstituted $C_6$-$C_{60}$ arylene group, a substituted or unsubstituted $C_1$-$C_{60}$ heteroarylene group, or a substituted or unsubstituted divalent non-aromatic condensed polycyclic group.

In an exemplary embodiment, X in Formula 1 may be or include a group represented by one of the following Formulae 2a to 2c.

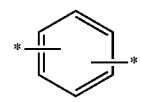

2a

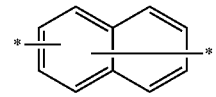

2b

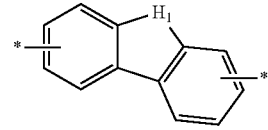

2c

In Formulae 2a to 2c, $H_1$ may be, e.g., $CR_1R_2$, O, or S.

$R_1$ and $R_2$ may each independently be selected from or include, e.g., a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

* denotes a binding site.

In an exemplary embodiment, in Formula 1, $Ar_1$ and $Ar_2$ may each independently be or include, e.g., a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

In an exemplary embodiment, in Formula 1, $Ar_1$ and $Ar_2$ may each independently be a group represented by one of the following Formulae 3a to 3d.

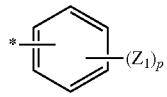
3a

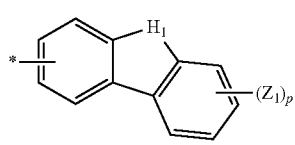
3b

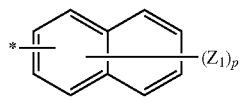
3c

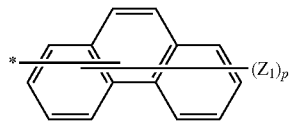
3d

In Formulae 3a to 3d, $H_1$ may be, e.g., $CR_1R_2$, O, or S.

$R_1$, $R_2$, and $Z_1$ may each independently be selected from or include, e.g., a hydrogen, a deuterium, an amine group substituted with a $C_6$-$C_{20}$ aryl group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

p may be an integer selected from 1 to 9.

* denotes a binding site.

In an exemplary embodiment, in the formulae above, $R_1$, $R_2$, and $Z_1$ may each independently be selected from, e.g., a hydrogen, a deuterium, and a group represented by one of the following Formulae 4a to 4e.

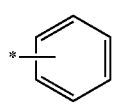
4a

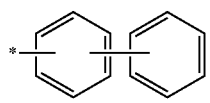
4b

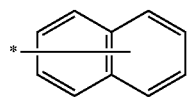
4c

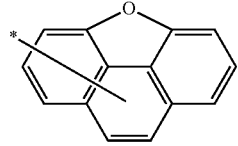
4d

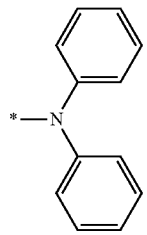
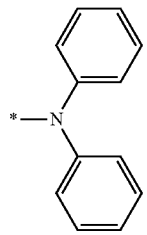
4e

In Formulae 4a to 4e, * denotes a binding site.

In an exemplary embodiment, the compound represented by Formula 1 may be represented by Formula 2, in which X, m, $Ar_1$, and $Ar_2$ are defined the same as those of Formula 1.

<Formula 2>

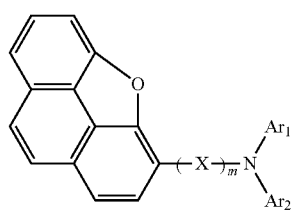

In an exemplary embodiment, the compound of Formula 1 may be represented by Formula 3, in which X, m, $Ar_1$, and $Ar_2$ are defined the same as those of Formula 1.

<Formula 3>

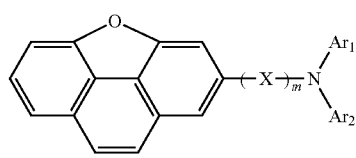

In an exemplary embodiment, the compound of Formula 1 may be represented by Formula 4, in which X, m, $Ar_1$, and $Ar_2$ are defined the same as those of Formula 1.

<Formula 4>

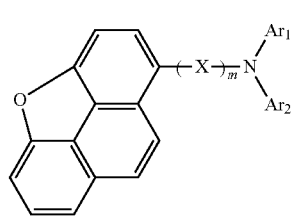

Substituents in Formulae 2 to 4 may be defined the same as those provided above.
In an exemplary embodiment, the compound represented by Formula 1 may be one of the following Compounds 1 to 90.
1
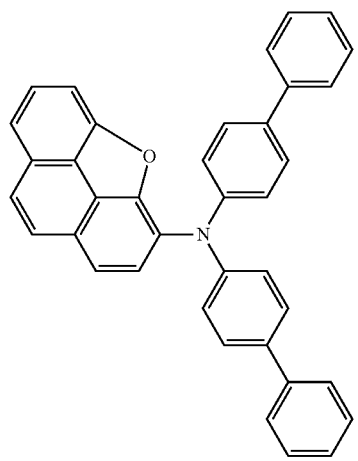
2
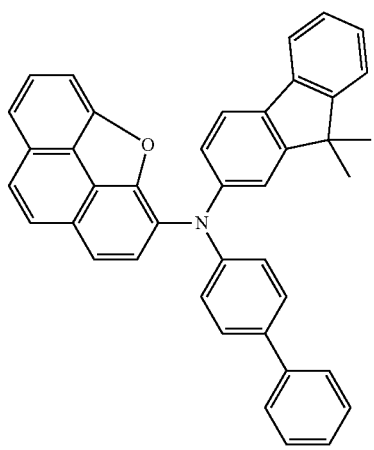
3
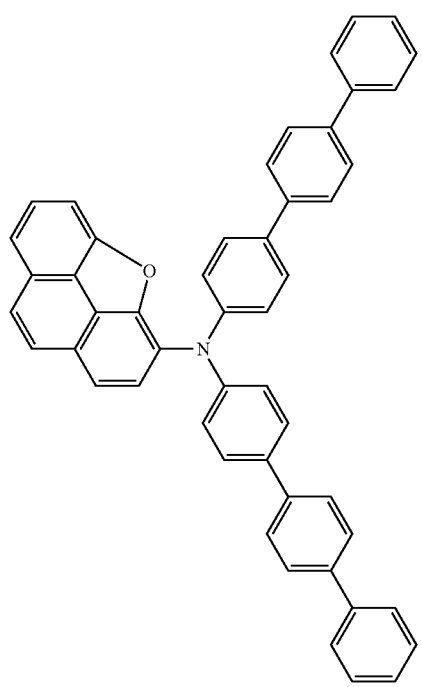
4
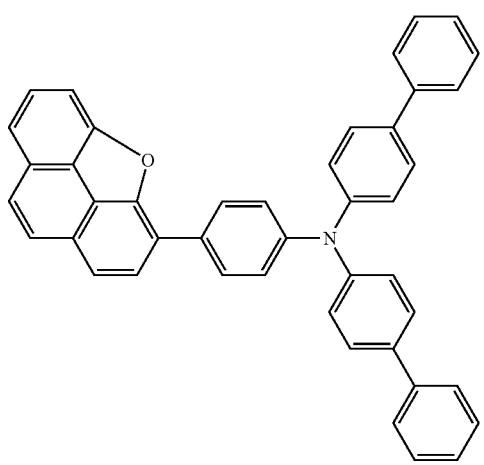
5
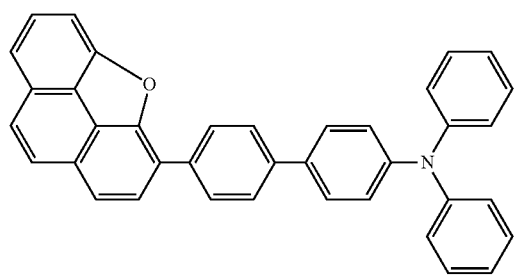
6
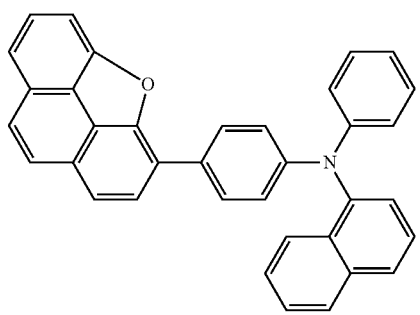

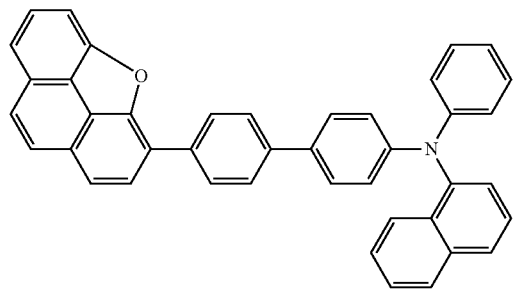
7
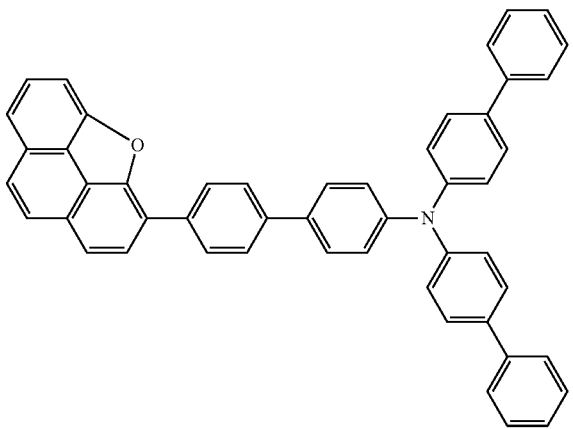
8
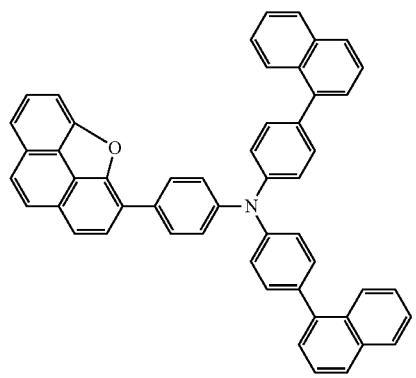
9
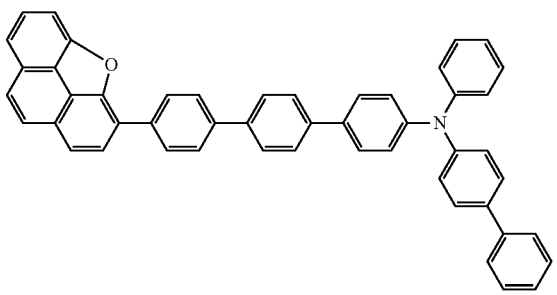
10
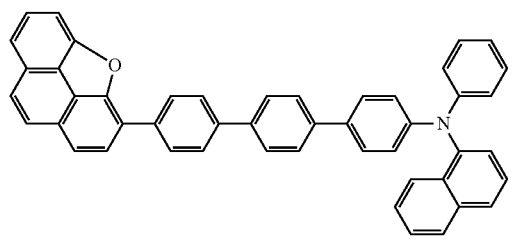
11
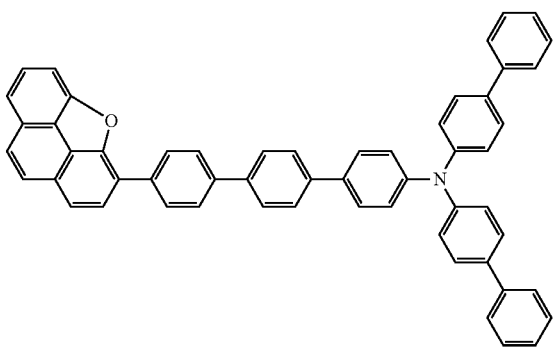
12
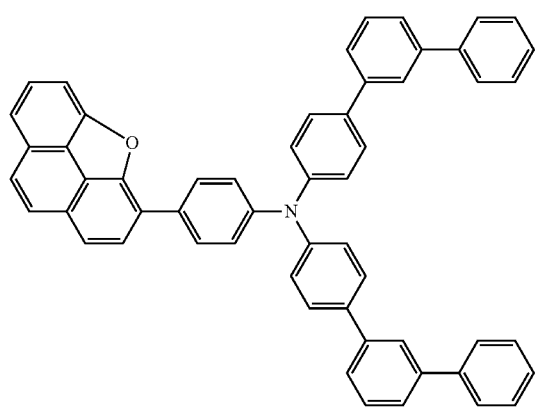
13
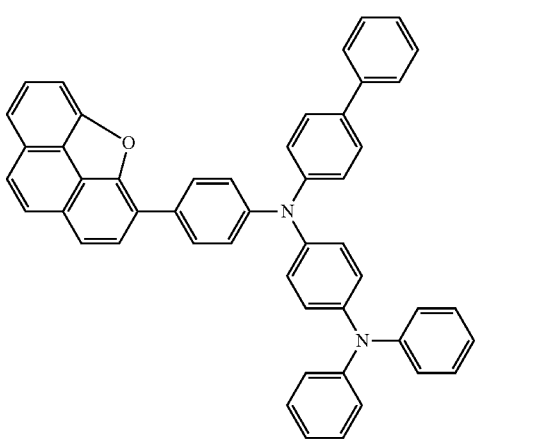
14

-continued
15
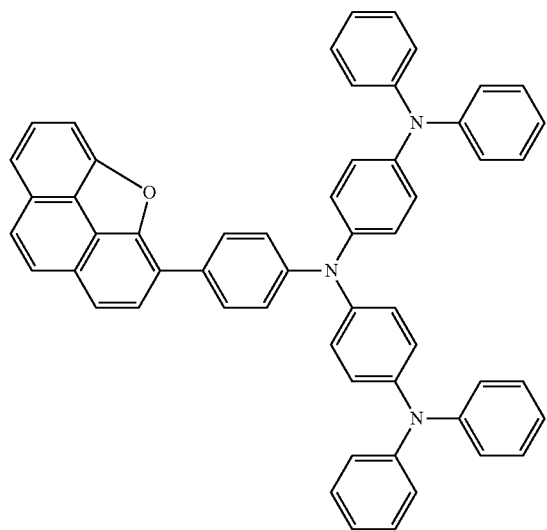
16
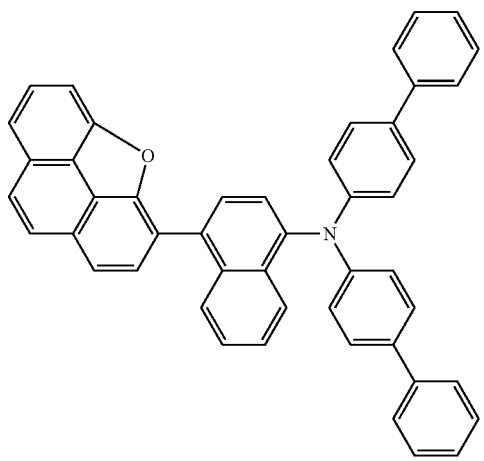
17
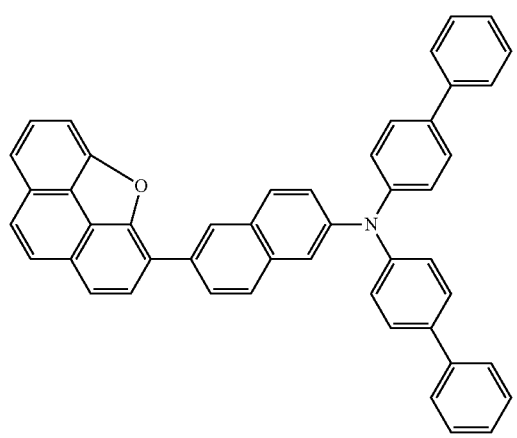
18
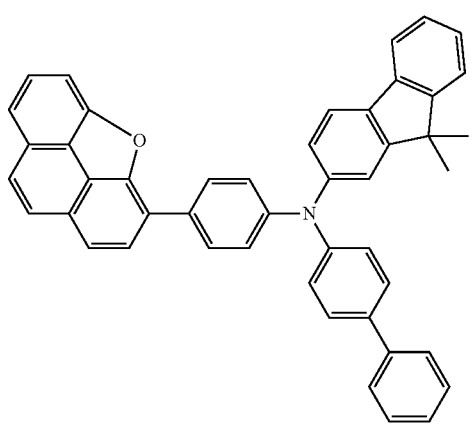
19
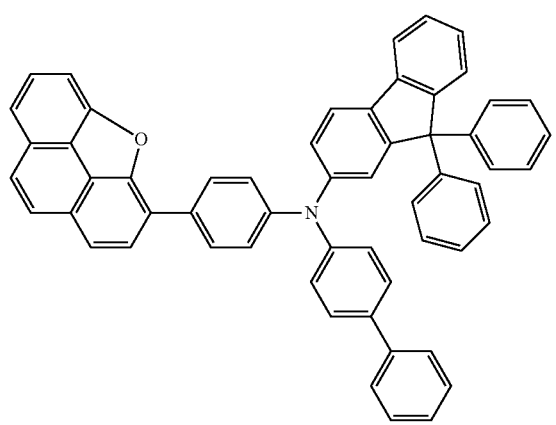
20
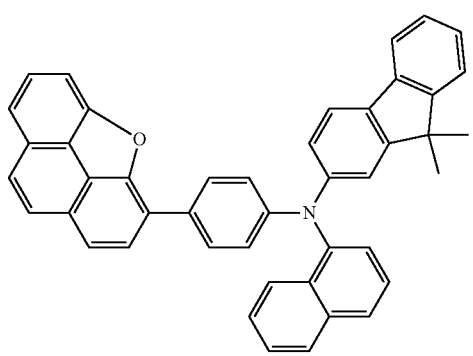

-continued
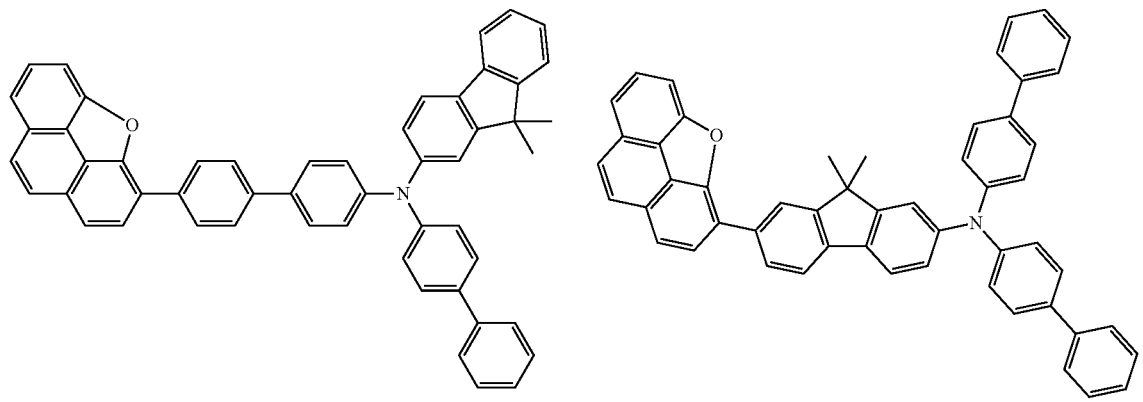
21
22
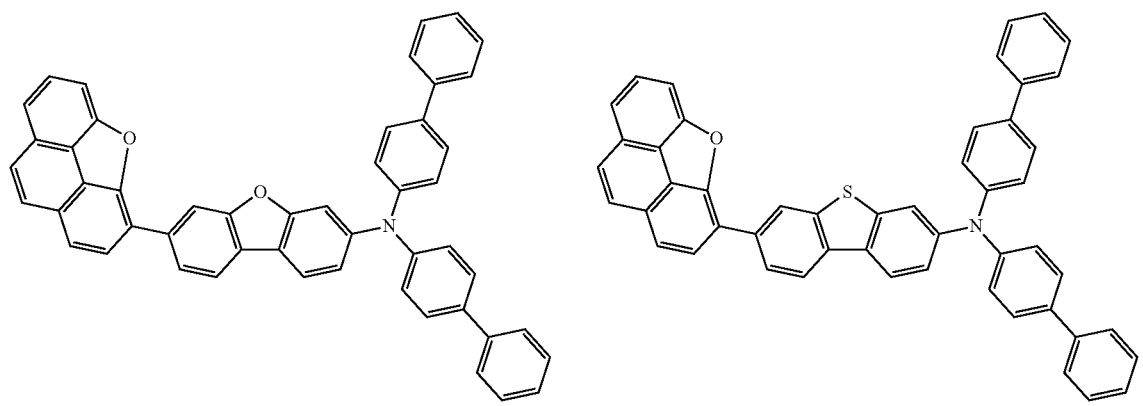
23
24
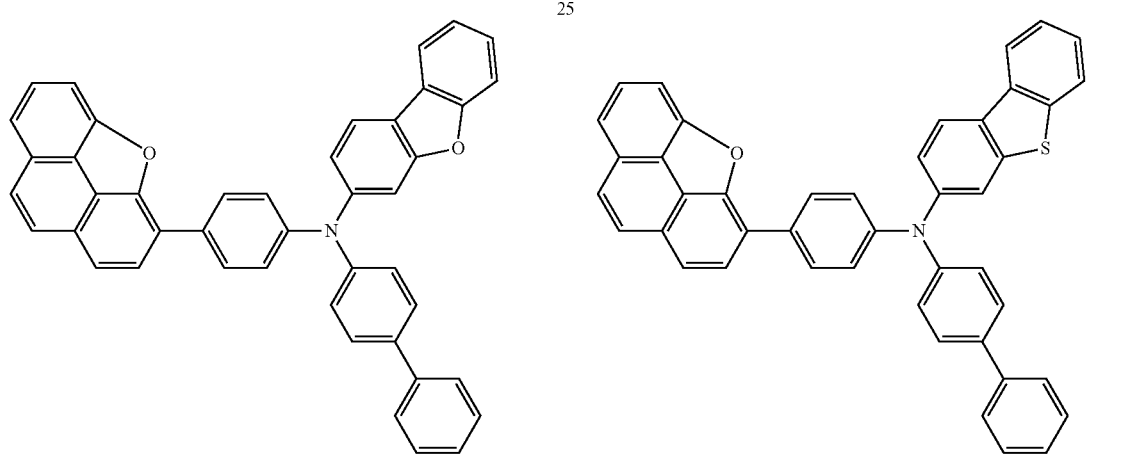
25
26

-continued
27
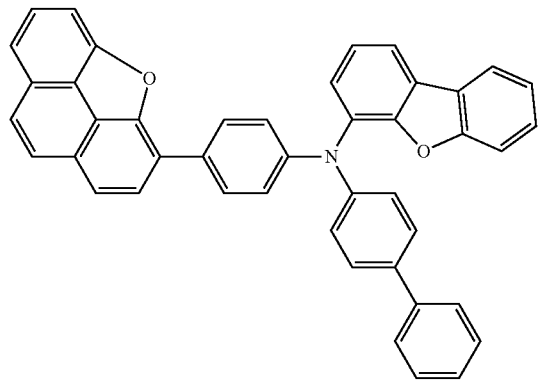
28
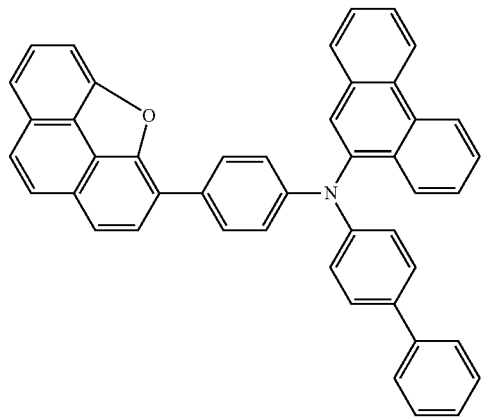
29
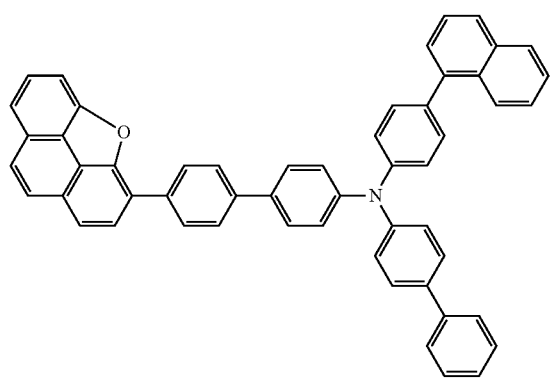
30
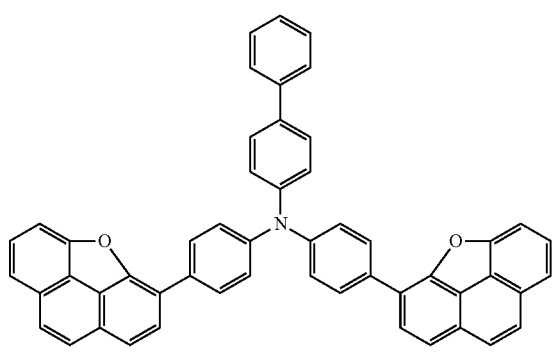
31
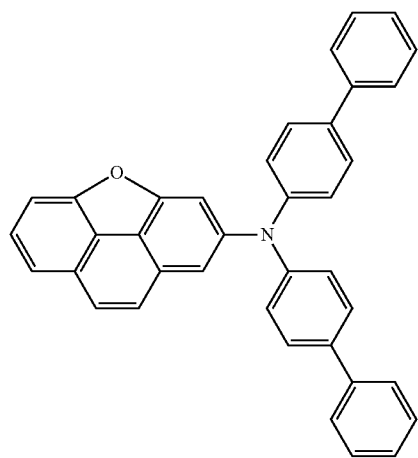
32
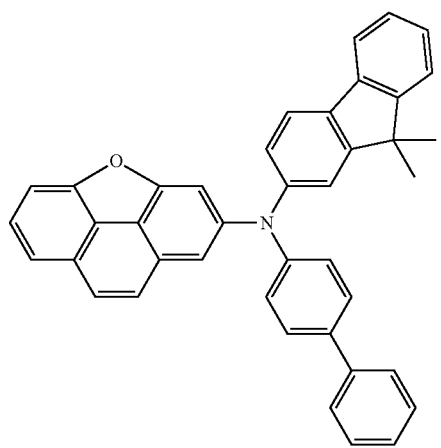

-continued
33
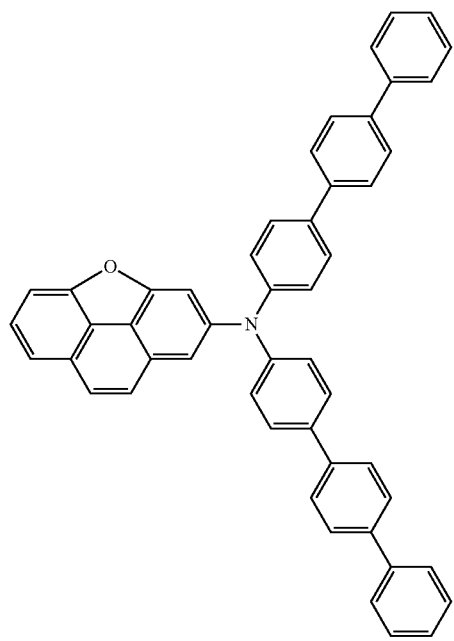
34
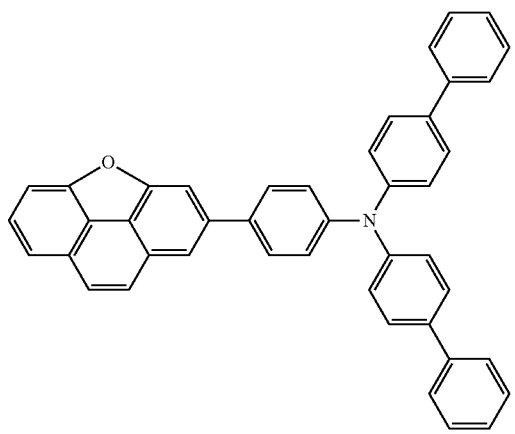
35
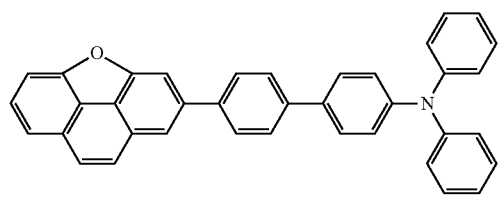
36
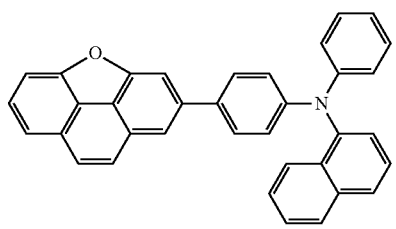
37
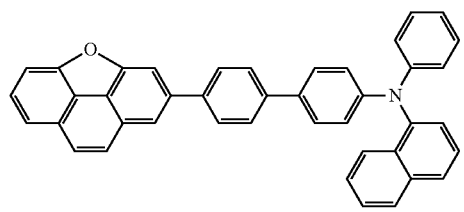
38
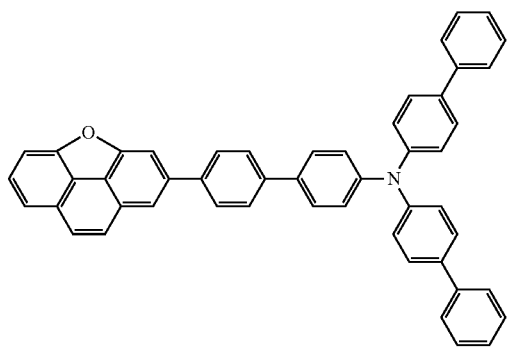
39
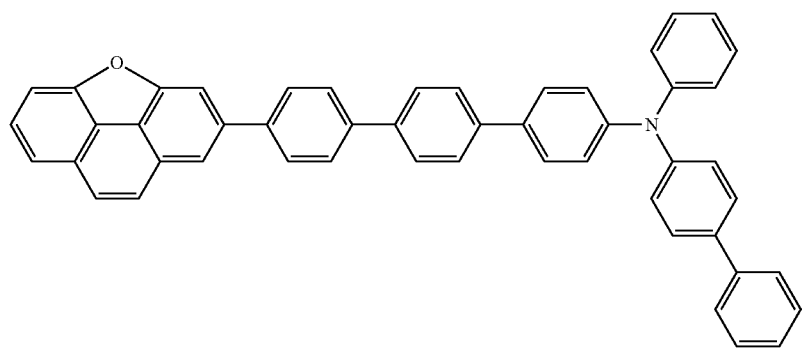

-continued
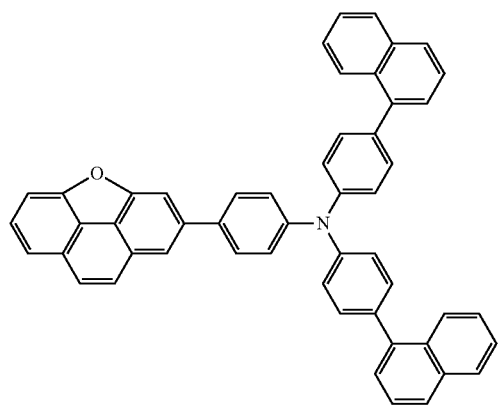
40
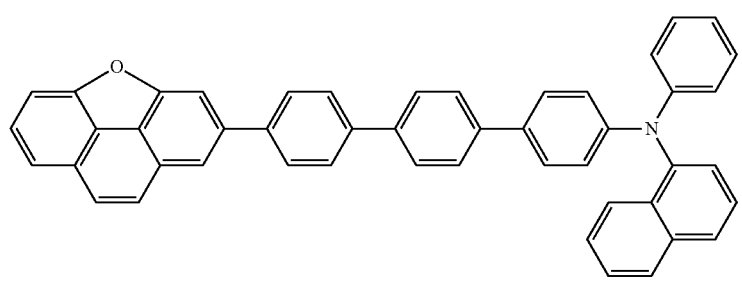
41
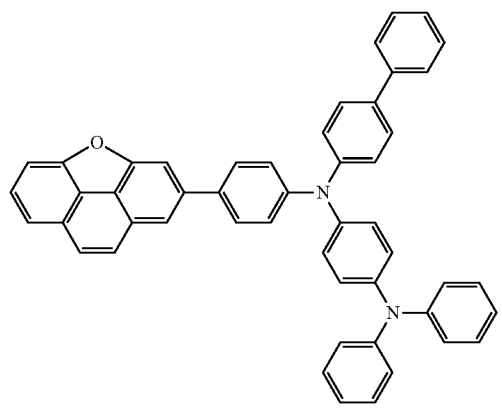
42
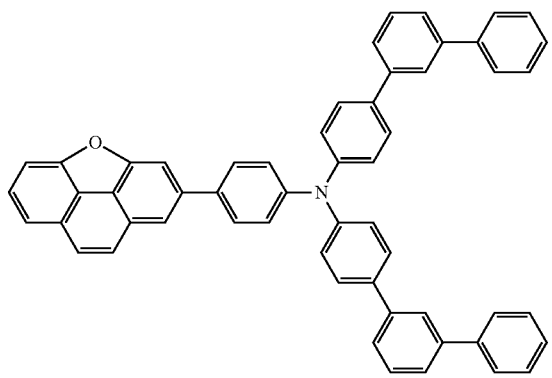
43
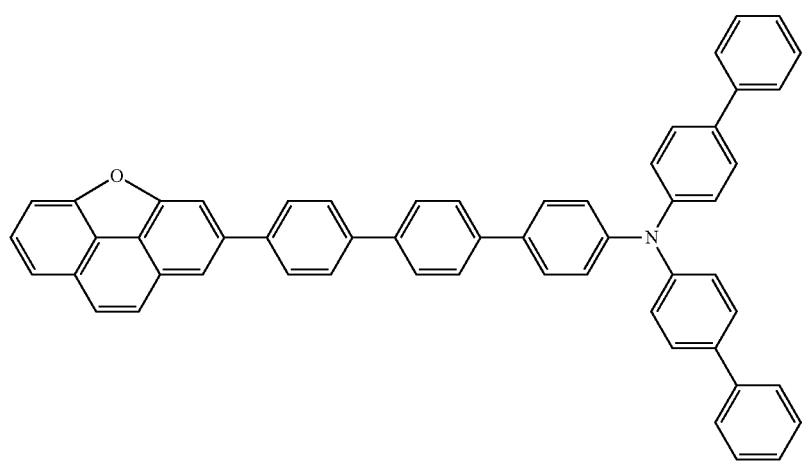
44

-continued
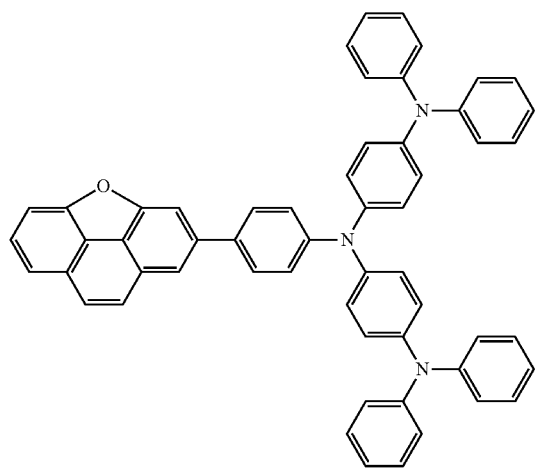
45
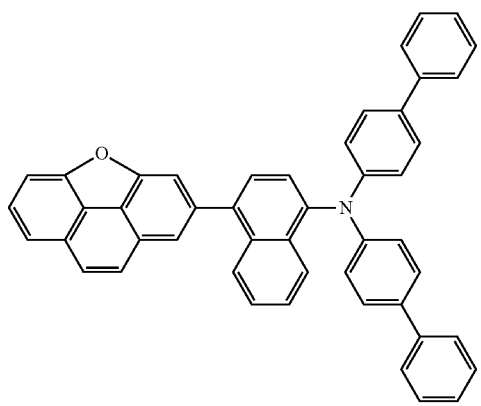
46
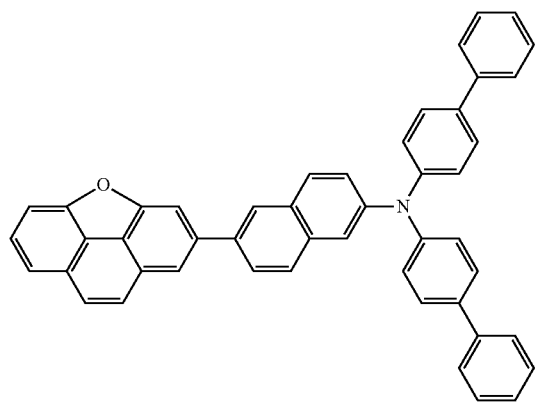
47
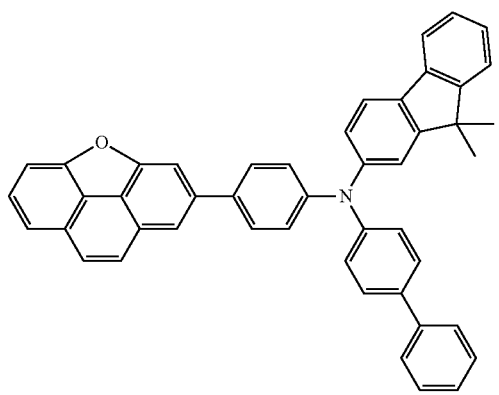
48
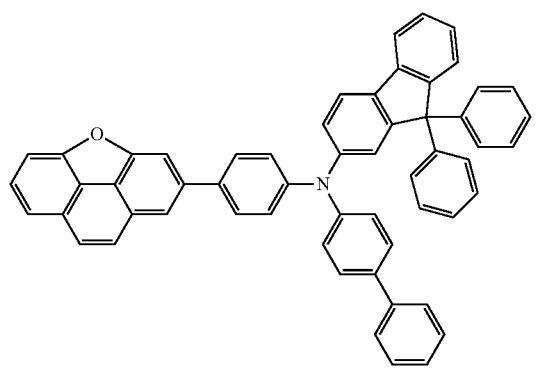
49
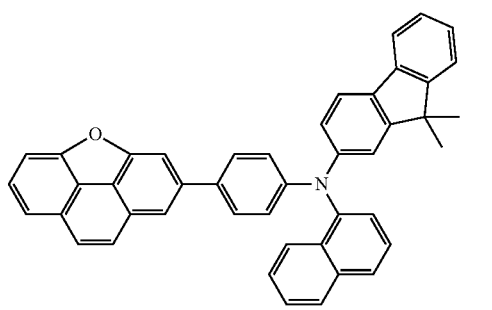
50
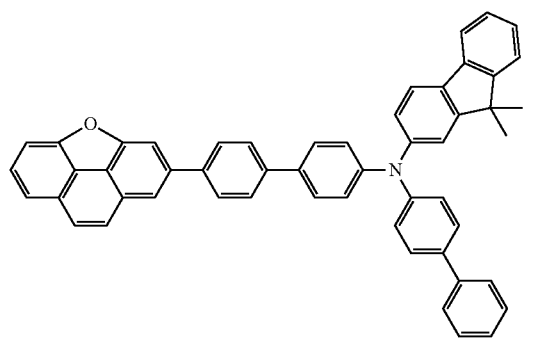
51
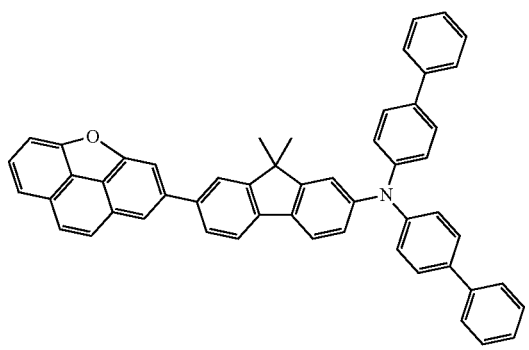
52

-continued
53
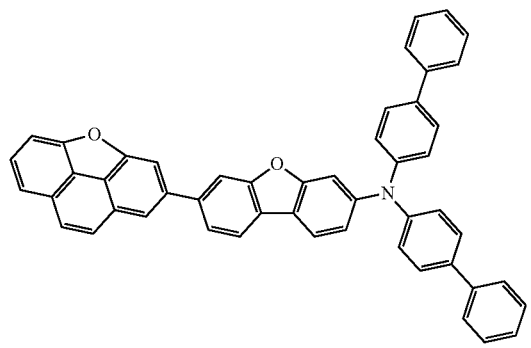
54
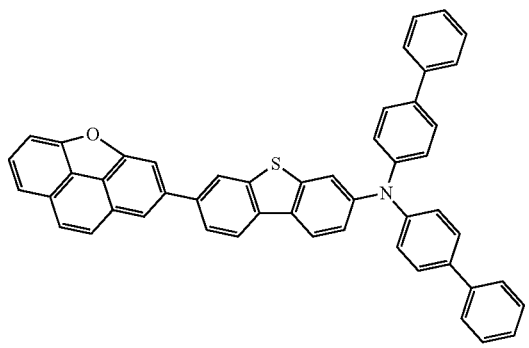
55
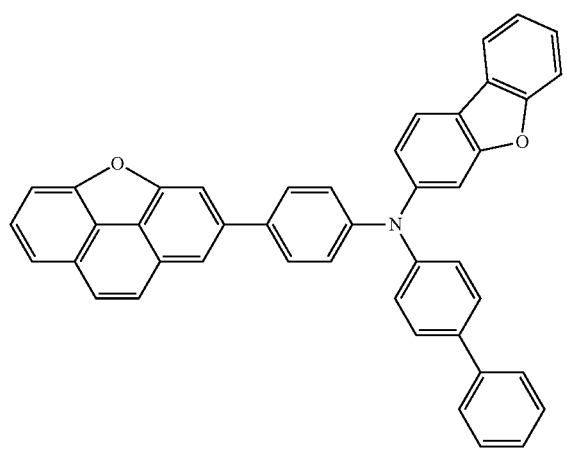
56
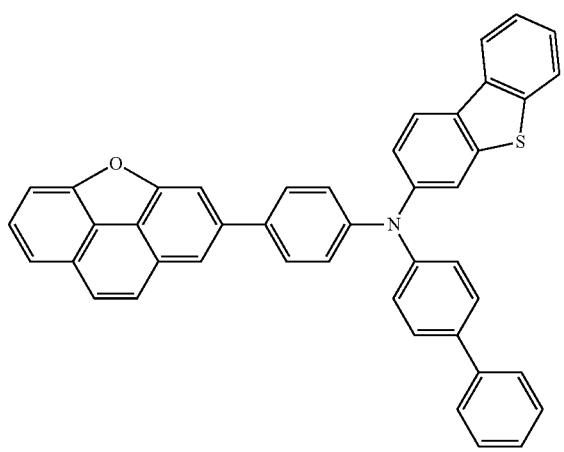
57
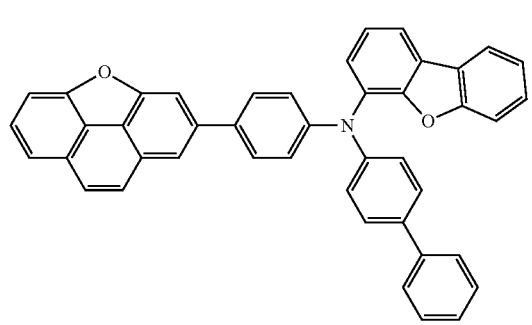
58
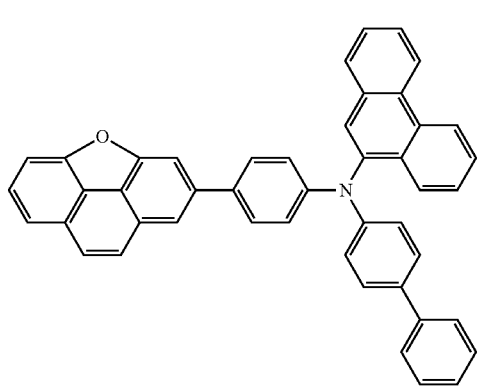
59
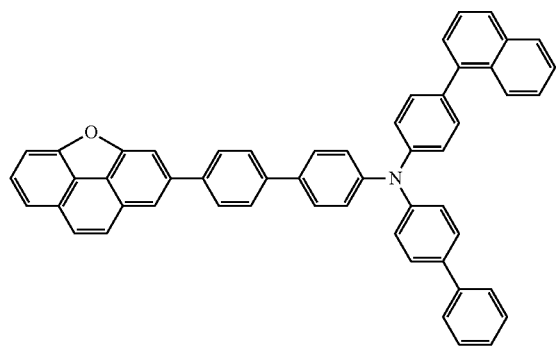
60
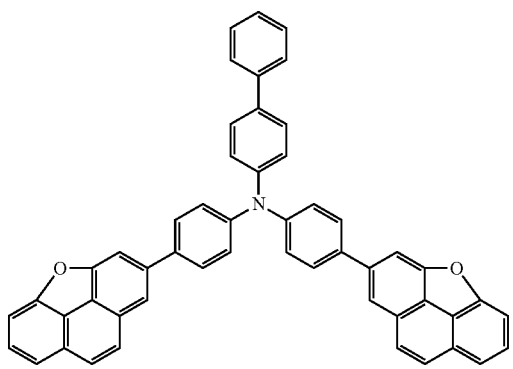

-continued
61 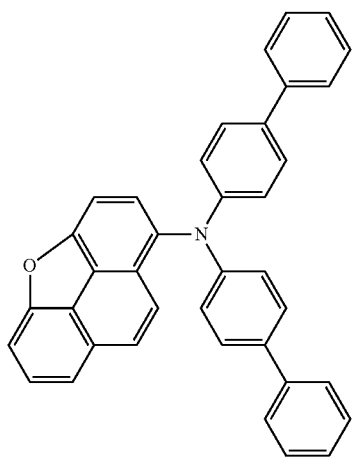
62 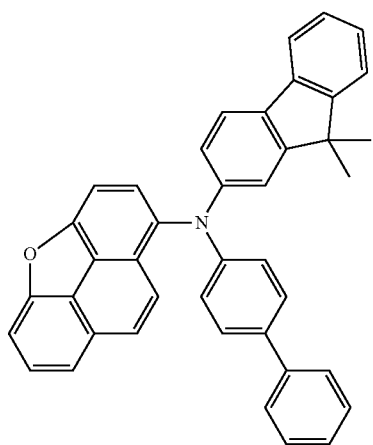
63 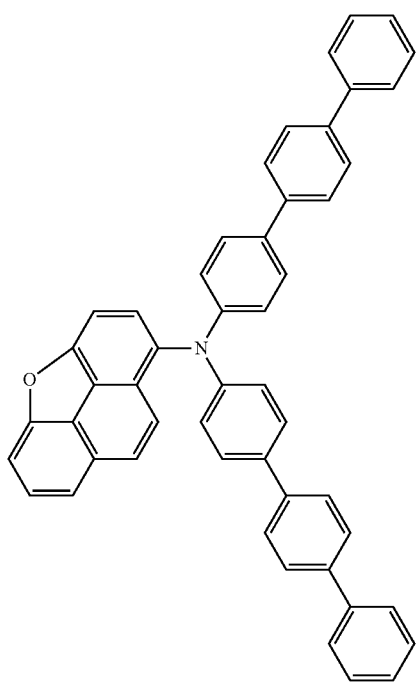
64 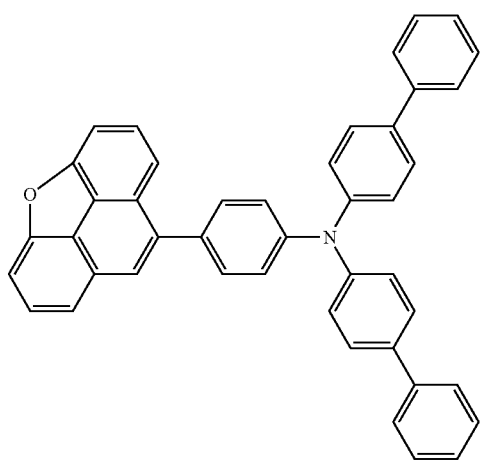
65 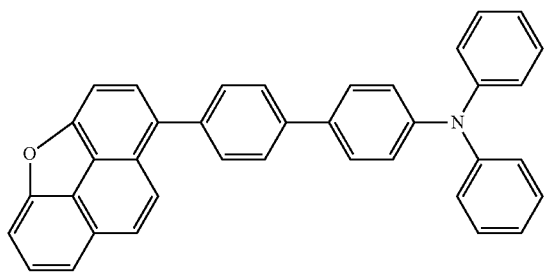
66 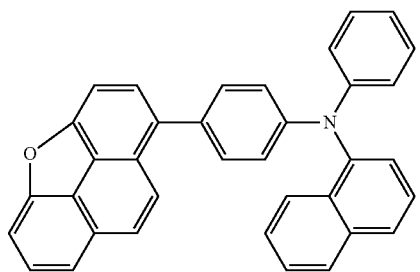

-continued
67
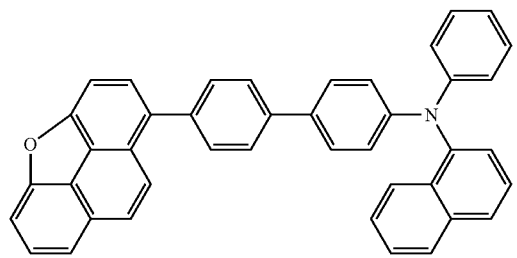
68
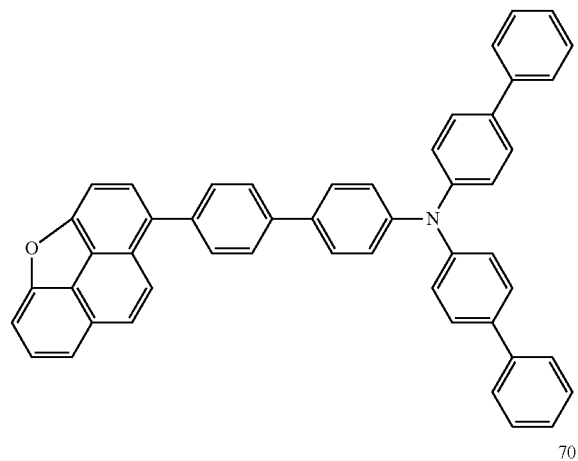
69
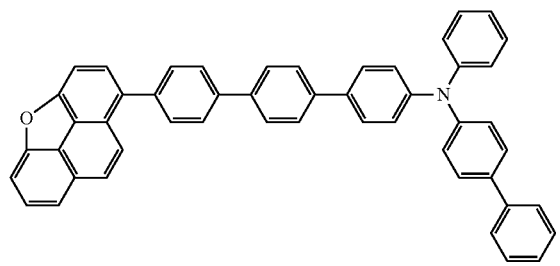
70
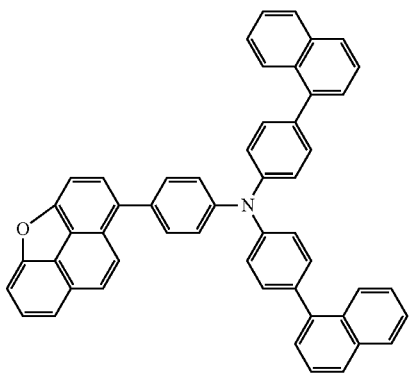
71
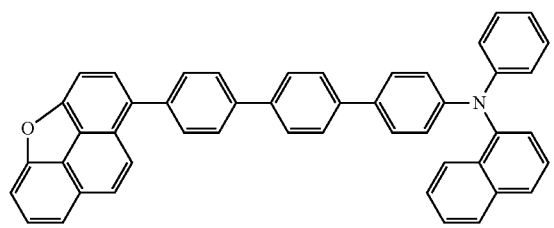
72
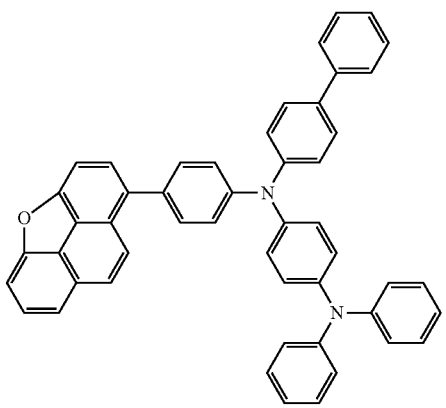
73
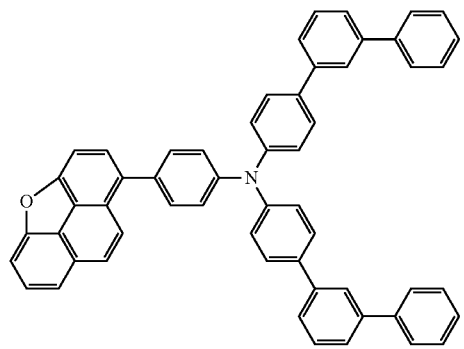
74
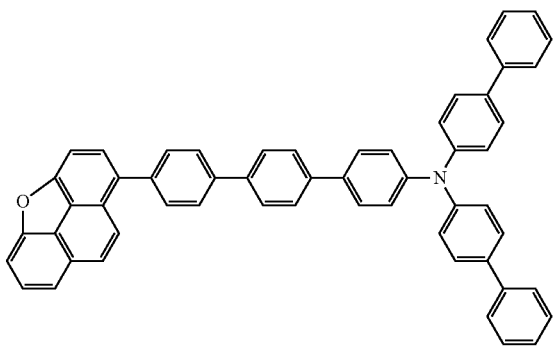

-continued
75
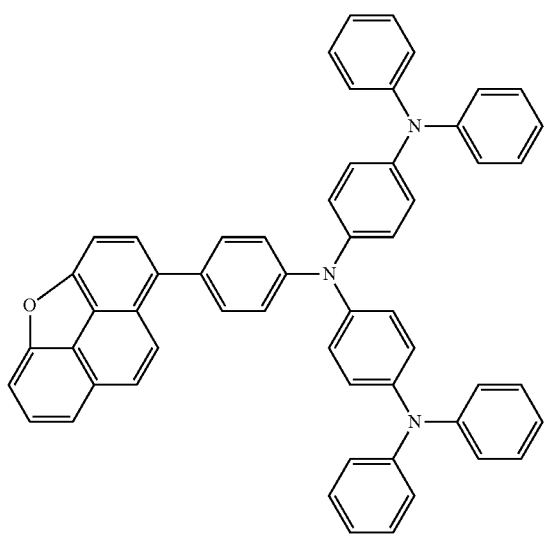
76
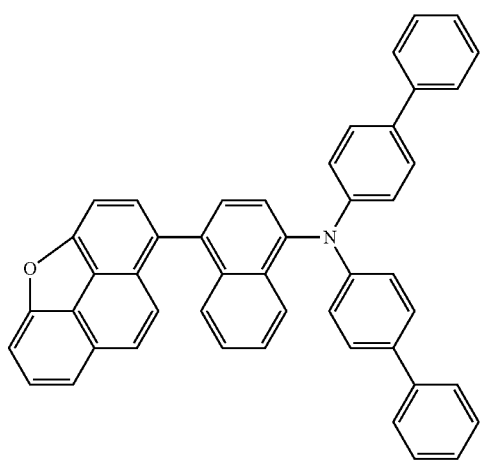
77
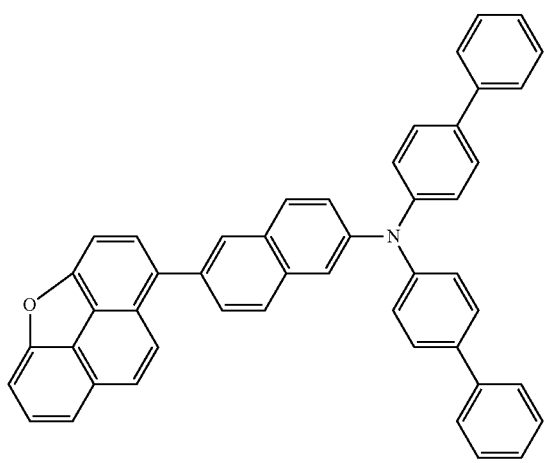
78
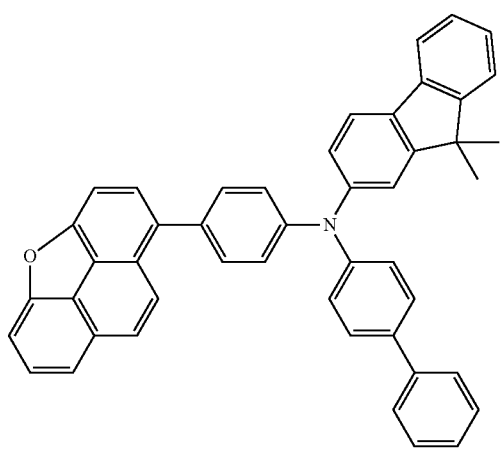
79
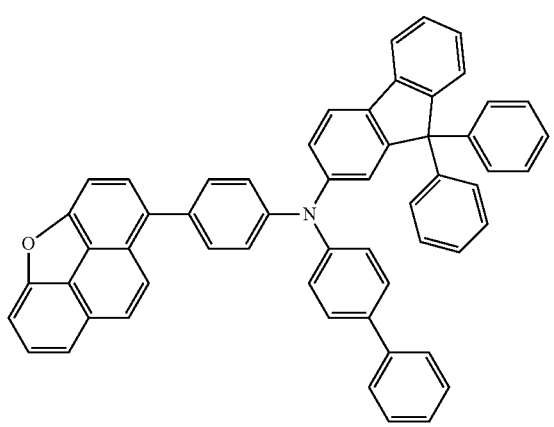
80
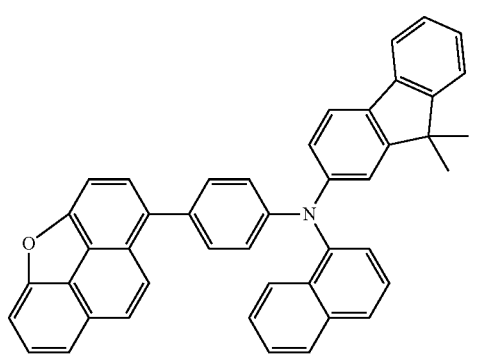

-continued
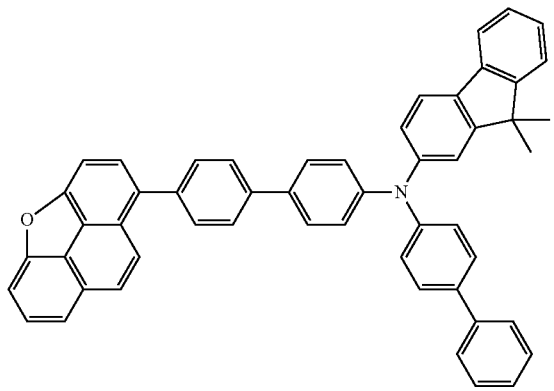
81
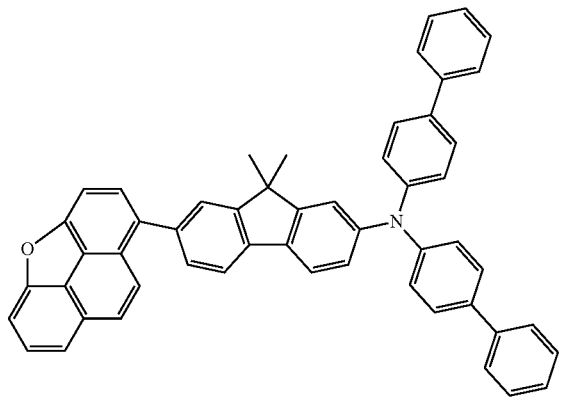
82
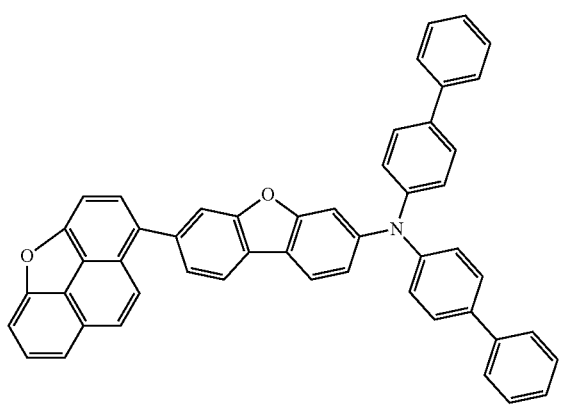
83
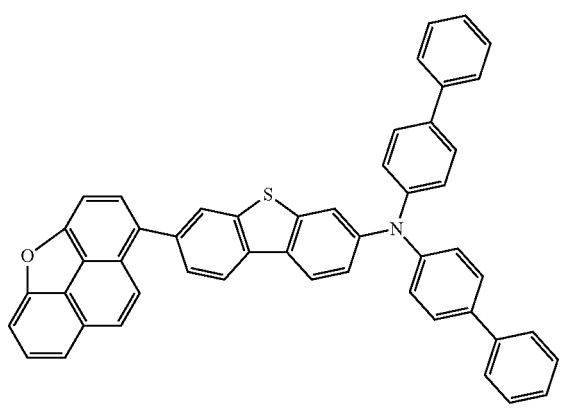
84
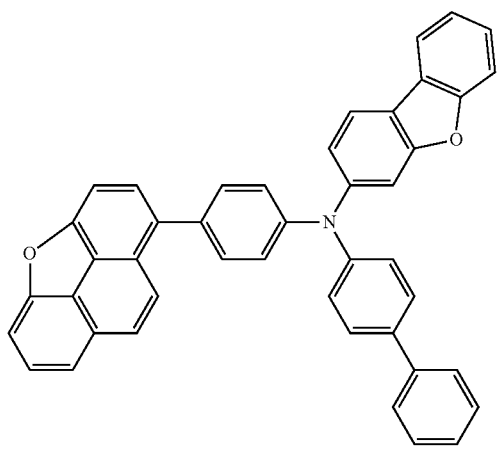
85
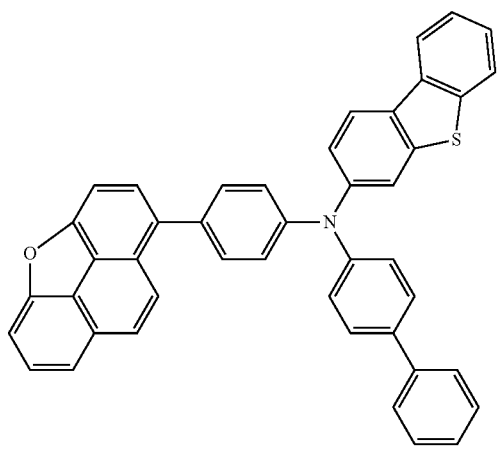
86

87

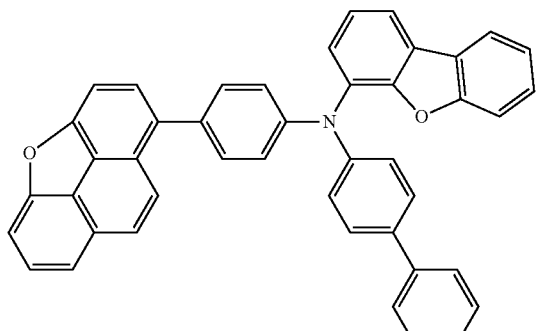

88

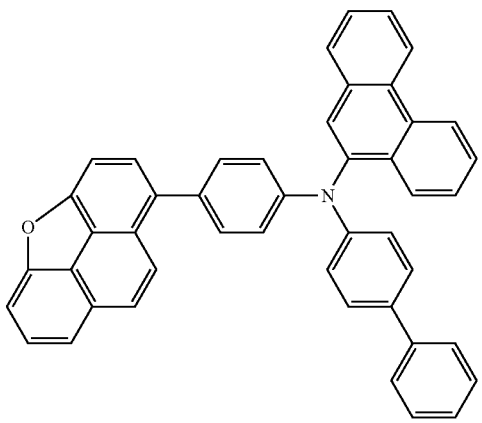

89

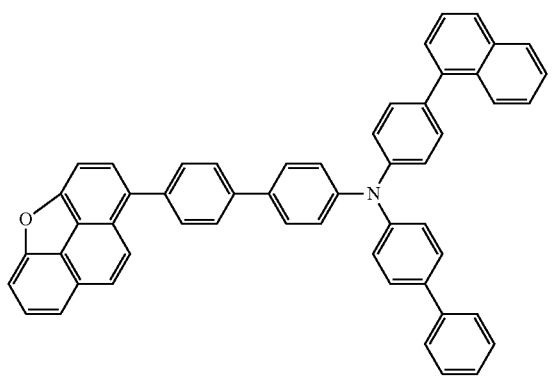

90

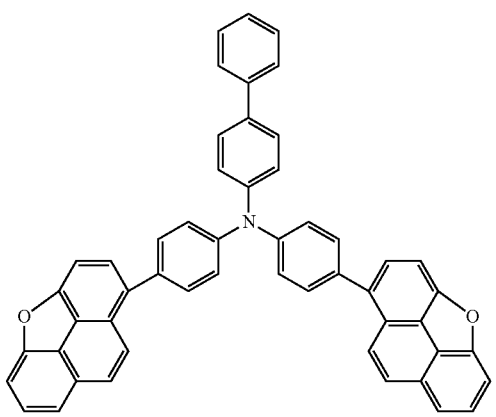

As used herein, the term "organic layer" refers to a single and/or a plurality of layers disposed between the first electrode and the second electrode in the organic light-emitting device. A material included in the "organic layer" is not limited to an organic material.

The FIGURE illustrates a schematic view of an organic light-emitting device 10 according to an embodiment. The organic light-emitting device 10 may include a first electrode 110, an organic layer 150, and a second electrode 190.

Hereinafter, a structure of an organic light-emitting device according to an example embodiment and a method of manufacturing an organic light-emitting device according to an example embodiment will be described in connection with the FIGURE.

In an implementation, a substrate may be additionally disposed under the first electrode 110 or on the second electrode 190 in the organic light-emitting device 10 of the FIGURE. The substrate may be a glass substrate or a transparent plastic substrate, each with excellent mechanical strength, thermal stability, transparency, surface smoothness, ease of handling, and water resistance.

The first electrode 110 may be formed by, e.g., depositing or sputtering a material for forming the first electrode 110 on the substrate. When the first electrode 110 is an anode, the material for forming the first electrode 110 may be selected from materials having a high work function to facilitate hole injection. The first electrode 110 may be a reflective electrode, a semi-transmissive electrode, or a transmissive electrode. The material for forming the first electrode 110 may include an indium tin oxide (ITO), indium zinc oxide (IZO), tin oxide ($SnO_2$), or zinc oxide (ZnO), each having transparency and excellent conductivity. In an implementation, when the first electrode 110 is a semi-transmissive electrode or a reflective electrode, the material for forming the first electrode 110 may include at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including two or more layers. For example, the first electrode 110 may have a triple-layer structure of ITO/Ag/ITO.

The organic layer 150 is disposed on the first electrode 110. The organic layer 150 includes an emission layer.

The organic layer 150 may include a hole transport region that is disposed between the first electrode 110 and the emission layer. The organic layer 150 may include an electron transport region that is disposed between the emission layer and the second electrode 190.

The hole transport region may include at least one of a hole injection layer (HIL), a hole transport layer (HTL), and an electron blocking layer (EBL). the electron transport region may include at least one of a hole blocking layer (HBL), an electron transport layer (ETL), and an electron injection layer (EIL).

The hole transport region may have a single-layer structure formed of a single material, a single-layer structure formed of a plurality of different materials, or a multi-layer structure having a plurality of layers formed of a plurality of different materials.

For example, the hole transport region may have a single-layer structure formed of a plurality of different materials, or a structure of HIL/HTL, a structure of HIL/HTL/buffer layer, a structure of HIL/buffer layer, a structure of HTL/buffer layer, or a structure of HIL/HTL/EBL, wherein layers of each of the structures are sequentially stacked from the first electrode 110 in this stated order.

When the hole transport region includes an HIL, the HIL may be formed on the first electrode 110 by using various suitable methods, such as vacuum deposition, spin coating, casting, a Langmuir-Blodgett (LB) method, ink-jet printing, laser-printing, or laser-induced thermal imaging (LITI).

When the HIL is formed by vacuum deposition, the vacuum deposition may be performed at a deposition temperature in a range of about 100° C. to about 500° C., at a vacuum degree in a range of about $10^{-8}$ torr to about $10^{-3}$ torr, and/or at a deposition rate in a range of about 0.01 Å/sec to about 100 Å/sec, in consideration of a composition of a compound for forming the HIL and a structure of the suitable or desired HIL.

When the HIL is formed by spin coating, the spin coating may be performed at a coating rate in a range of about 2,000 rpm to about 5,000 rpm and at a temperature in a range of about 80° C. to about 200° C., in consideration of a composition of a compound for forming the HIL and a structure of the suitable or desired HIL.

When the hole transport region includes an HTL, the HTL may be formed on the first electrode 110 or on the HIL by using various suitable methods, such as vacuum deposition, spin coating, casting, a LB method, ink-jet printing, laser-printing, or LITI. When the HTL is formed by vacuum deposition or by spin coating, the deposition conditions or the coating conditions may be inferred based on the deposition conditions or the coating conditions for forming the HIL.

The hole transport region may include, e.g., at least one selected from m-MTDATA, TDATA, 2-TNATA, NPB, β-NPB, TPD, Spiro-TPD, Spiro-NPB, α-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), and the compound represented by Formula 1 according to an exemplary embodiment.

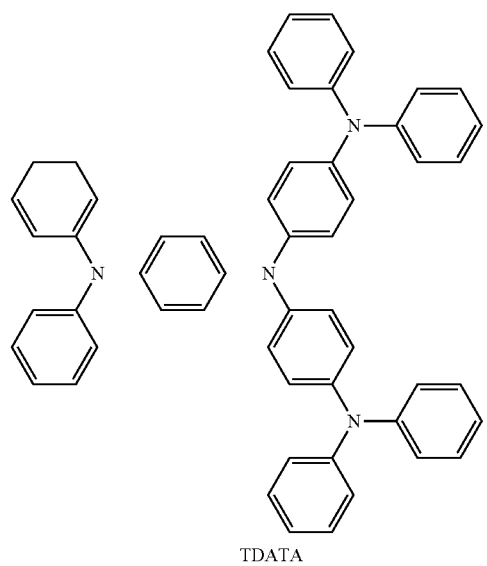

TDATA

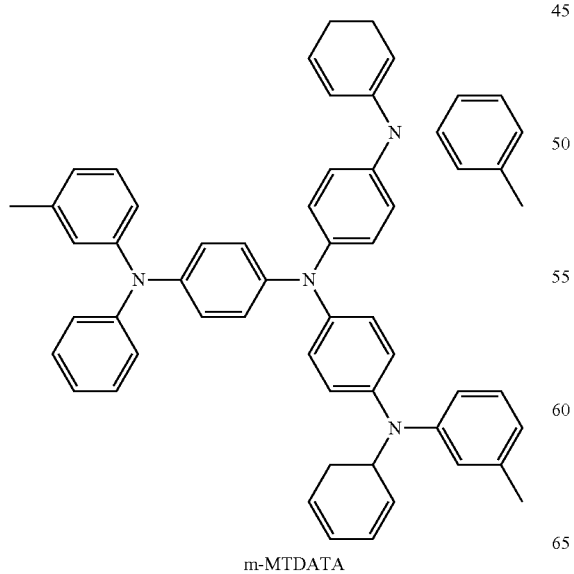

m-MTDATA

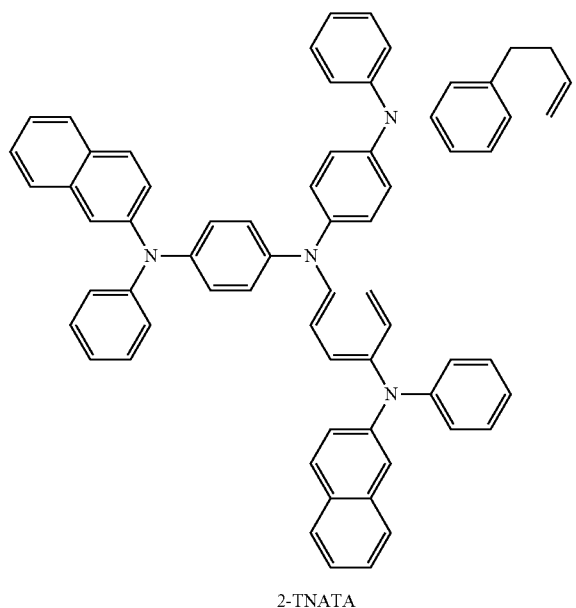

2-TNATA

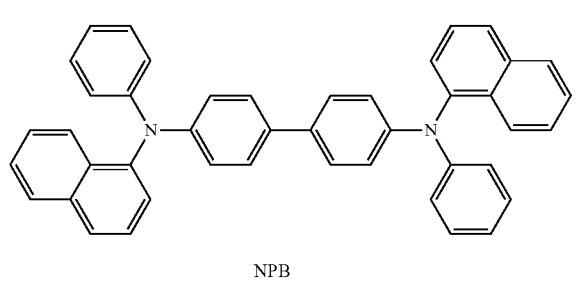

NPB

-continued

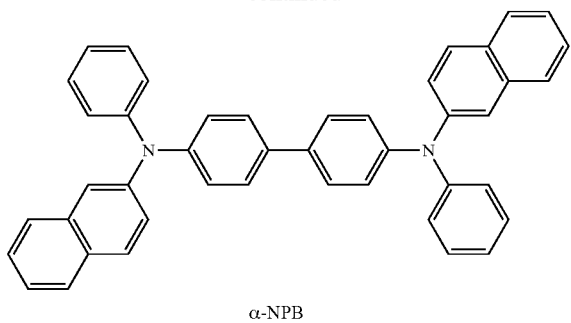

α-NPB

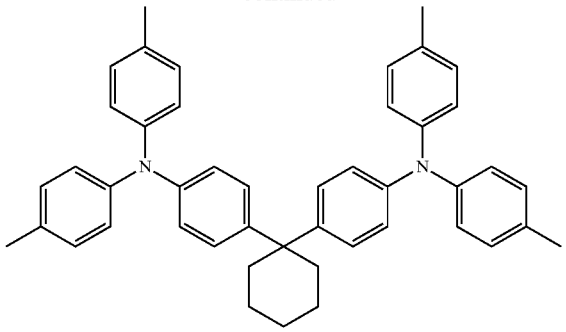

TAPC

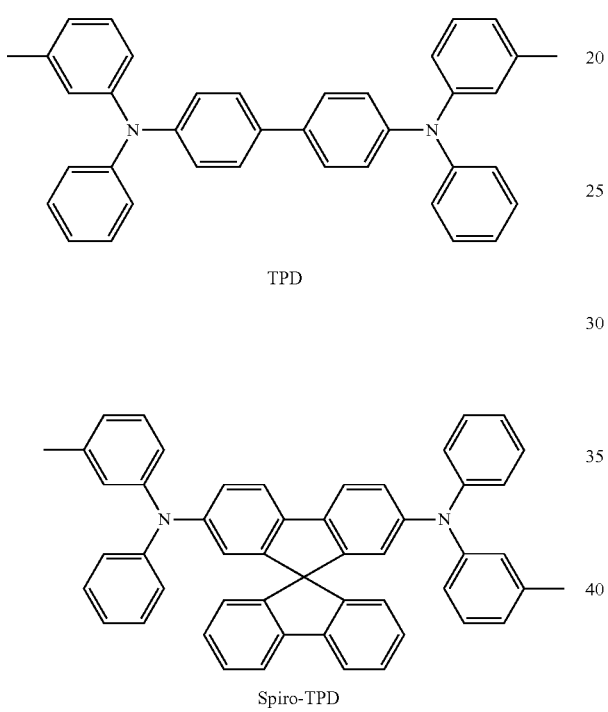

TPD

Spiro-TPD

Spiro-NPB

β-NPB

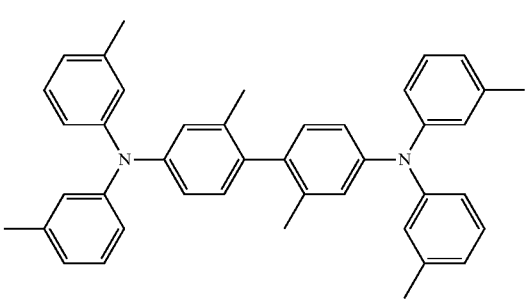

HMTPD

For example, the hole transport layer may include the compound of Formula 1 according to an exemplary embodiment.

A thickness of the hole transport region may be in a range of about 100 Å to about 10,000 Å, e.g., about 100 Å to about 1,000 Å. When the hole transport region includes both an HIL and an HTL, a thickness of the HIL may be in a range of about 100 Å to about 10,000 Å, e.g., about 100 Å to about 1,000 Å, and a thickness of the HTL may be in a range of about 50 Å to about 2,000 Å, e.g., about 100 Å to about 1,500 Å. When thicknesses of the hole transport region, the HIL, and the HTL are within these ranges described above, hole transporting properties may be suitable or satisfactory without a substantial increase in a driving voltage.

The hole transport region may further include a charge-generating material to improve conductive properties in addition to the materials described above. The charge-generating material may be homogeneously or non-homogeneously dispersed throughout the hole transport region.

The charge-generating material may include, e.g., a p-dopant. The p-dopant may be one selected from a quinone derivative, a metal oxide, and a cyano group-containing compound. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 below.

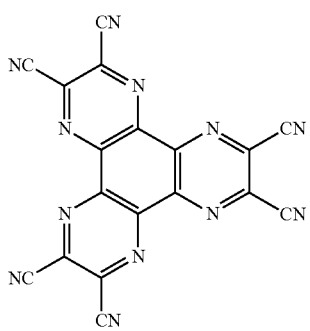

<Compound HT-D1>

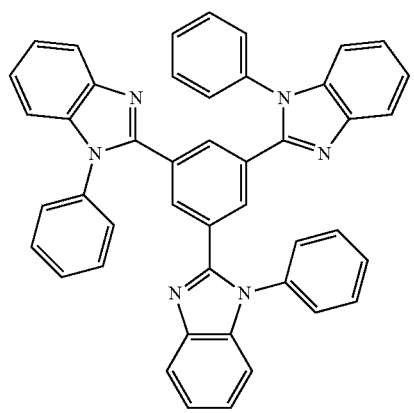

TPBi

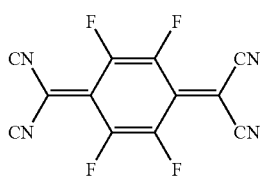

<F4-TCNQ>

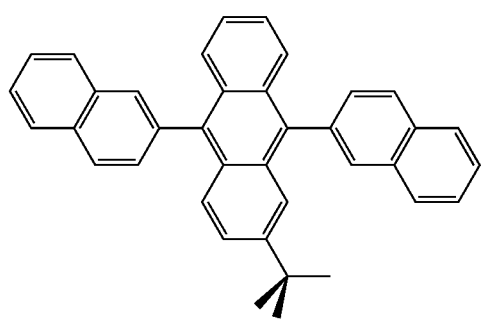

TBADN

The hole transport region may include a buffer layer. The buffer layer may compensate for an optical resonance distance of light according to a wavelength of the light emitted from the emission layer, and thus, may help improve light-emission efficiency. In this regard, a material that is included in the hole transport region may be used as a material that is included in the buffer layer. The EBL may help reduce and/or prevent electrons from being injected from the electron transport region.

The emission layer may be formed on the first electrode 110 or on the hole transport region by using various suitable methods, such as vacuum deposition, spin coating, casting, a LB method, ink-jet printing, laser-printing, or LITI. When the emission layer is formed by vacuum deposition or by spin coating, the deposition conditions or the coating conditions may be inferred based on the deposition conditions or the coating conditions for forming the HIL.

When the organic light-emitting device 10 is a full-color organic light-emitting device, the emission layer may be patterned into a red emission layer, a green emission layer, and a blue emission layer, according to an individual sub-pixel. Alternatively, the emission layer may have a structure of a red emission layer, a green emission layer, and a blue emission layer, each of which layers are sequentially stacked in the stated order. In this regard, a material emitting red light, a material emitting green light, and a material emitting blue light may have a mixed structure without having division of layers, thereby emitting white light.

The emission layer may include a host and a dopant.

The host may include, e.g., at least one selected from of TPBi, TBADN, ADN (also referred to as "DNA"), CBP, CDBP, and TCP:

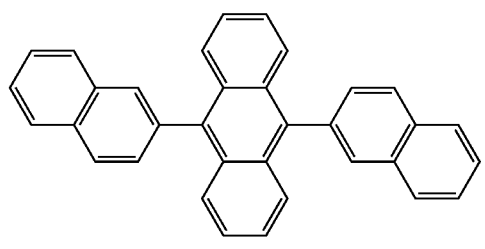

ADN

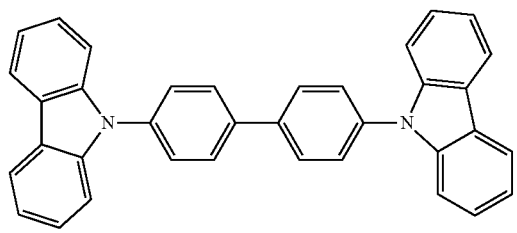

CBP

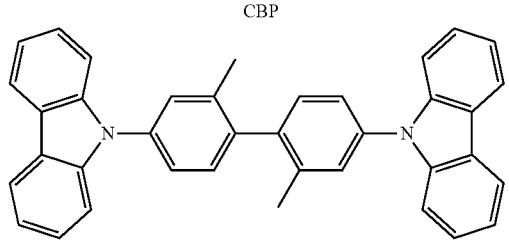

CDBP

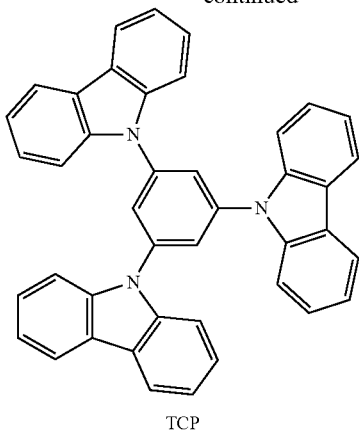

TCP

Alternatively, the host may include a compound represented by Formula 301:

$$Ar_{301}-[(L_{301})_{xb1}-R_{301}]_{xb2}$$ <Formula 301>

In Formula 301, $Ar_{301}$ may be selected from:

a naphthalene, a heptalene, a fluorenene, a Spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may be each independently selected from a hydrogen, $C_1$-$C_{60}$ alkyl group, a $C_2$-$C_{60}$ alkenyl group, a $C_6$-$C_{60}$ aryl group, and a $C_1$-$C_{60}$ heteroaryl group), $L_{301}$ may be selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, $R_{301}$ may be selected from:

a $C_1$-$C_{20}$ alkyl group and a $C_1$-$C_{20}$ alkoxy group, and a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3, and xb2 may be selected from 1, 2, 3, and 4.

For example, in Formula 301,
$L_{301}$ may be selected from:
a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and $R_{301}$ may be selected from:
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by Formula 301A:

<Formula 301A>

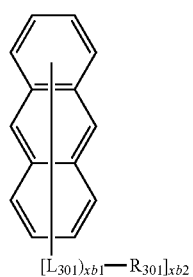

Substituents of Formula 301A may be inferred based on those provided above.

The compound of Formula 301 may include at least one of Compounds H1 to H42.

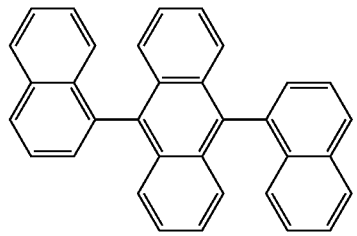

H1

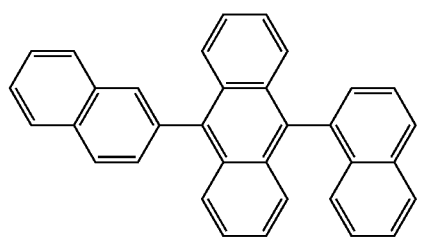

H2

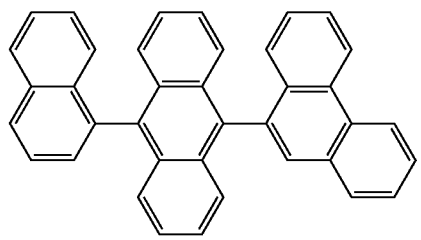

H3

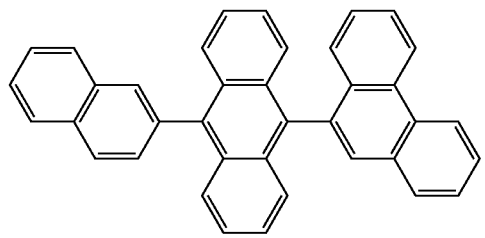

H4

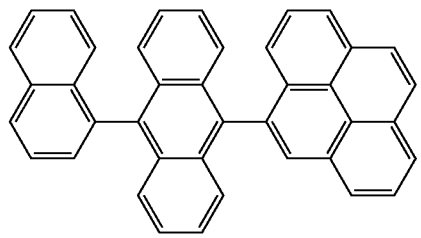

H5

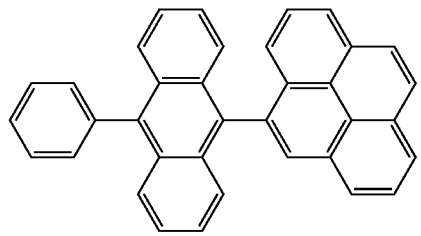

H6

H7
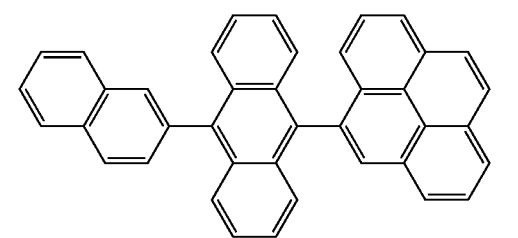
H8
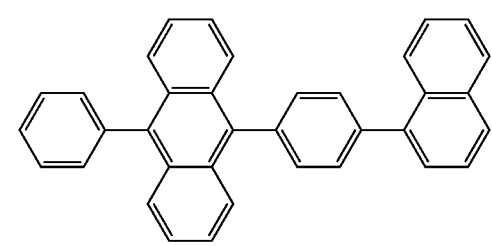
H9
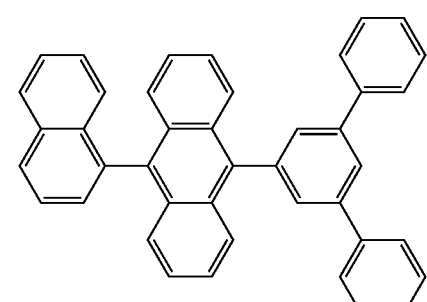
H10
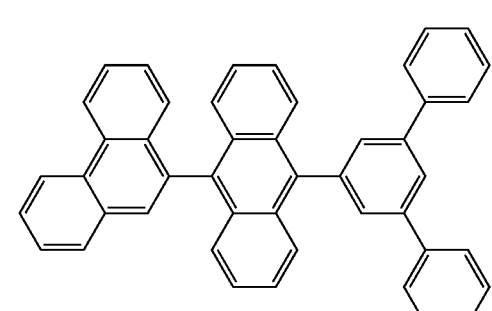
H11
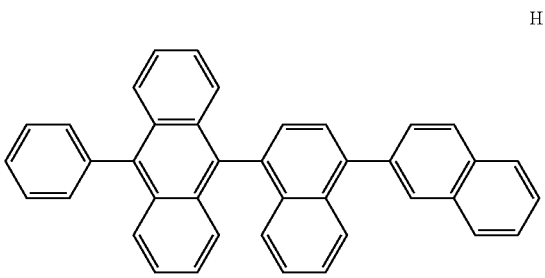
H12
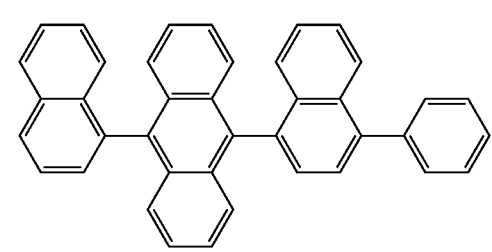
H13
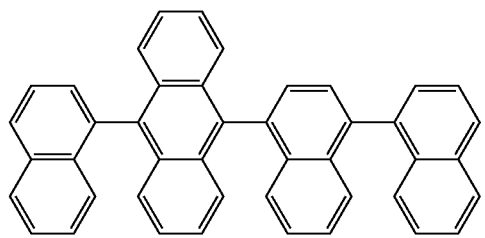
H14
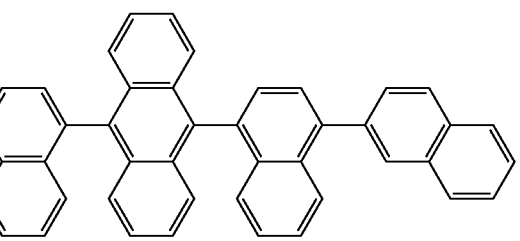
H15
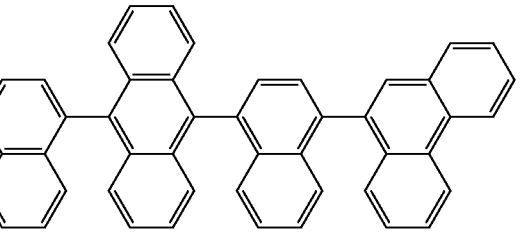
H16
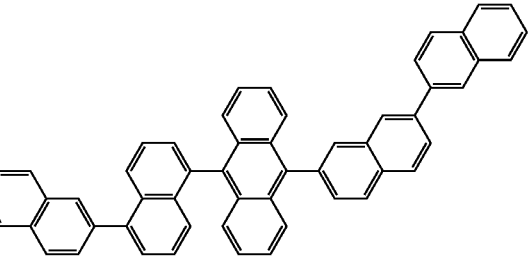
H17
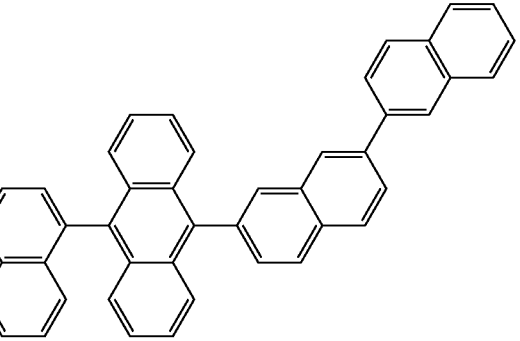

H18
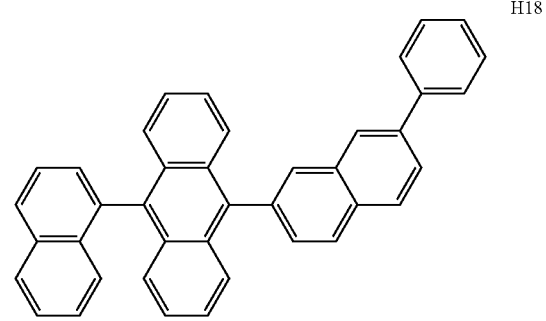
H19
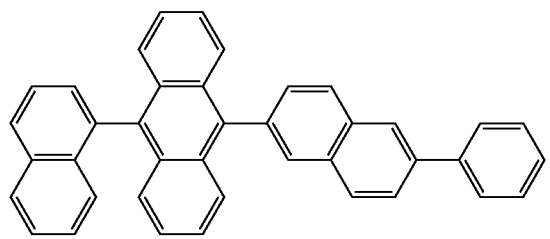
H20
H21
H22
H23
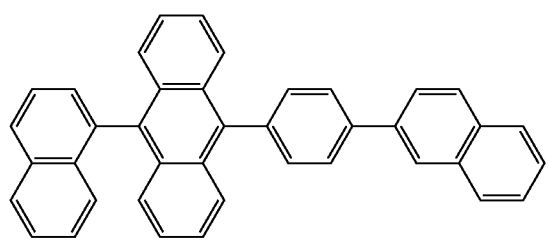
H24
H25
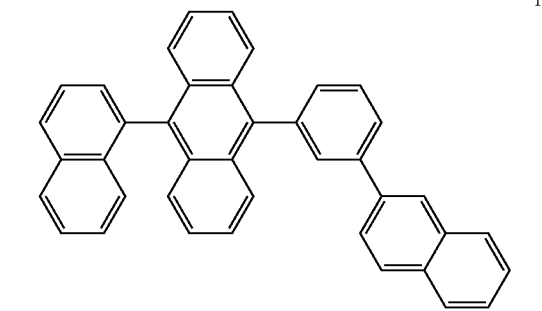
H26
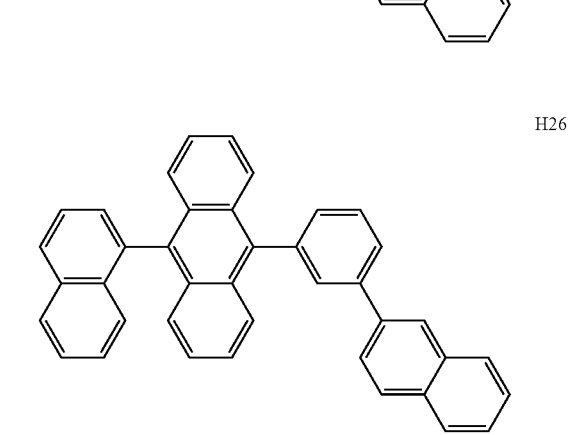
H27
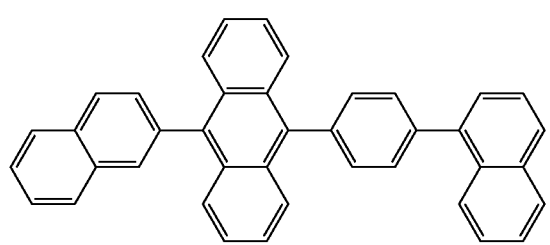

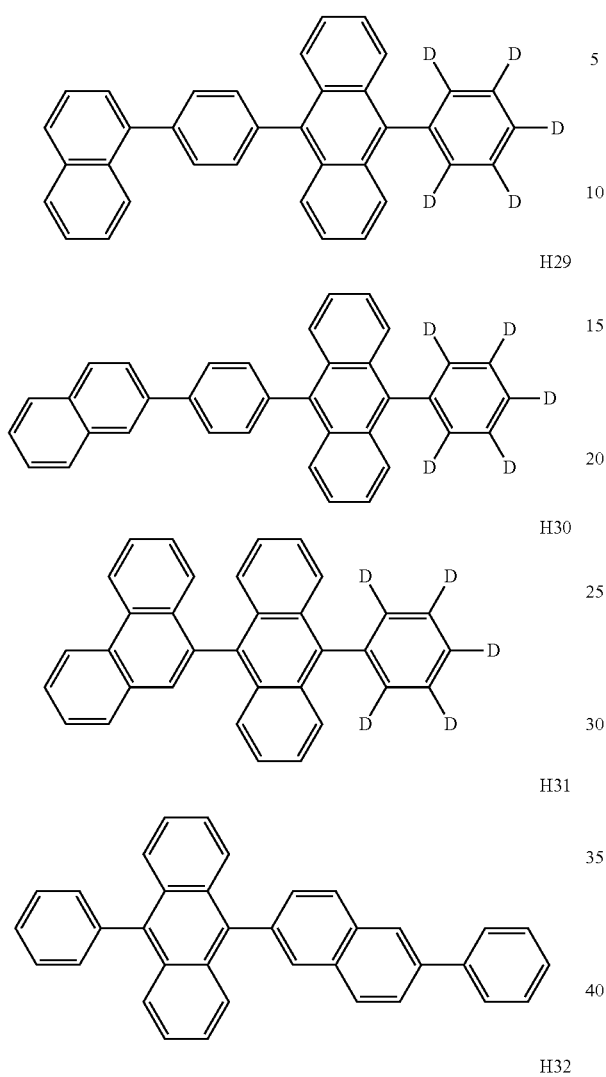
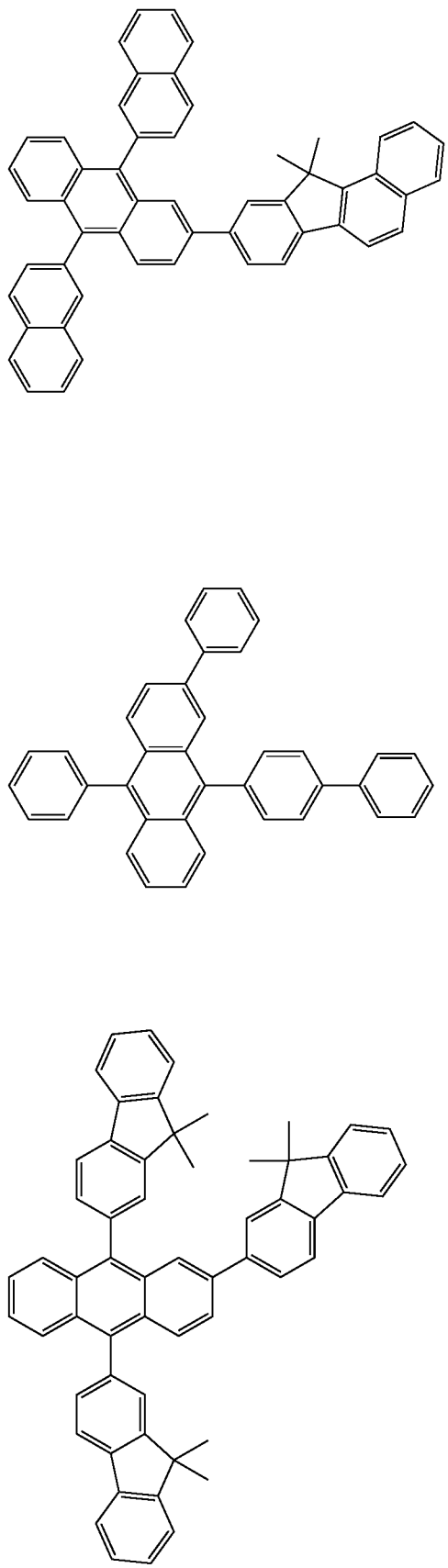

H37
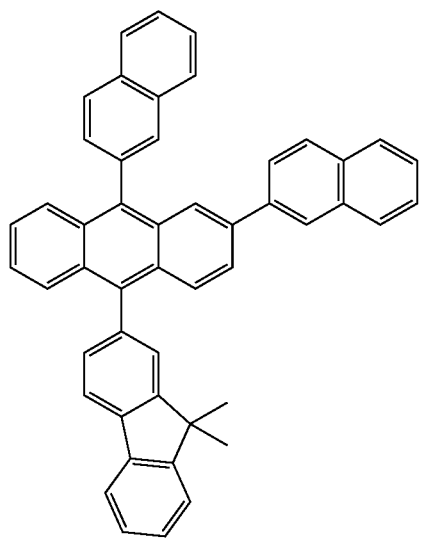
H38
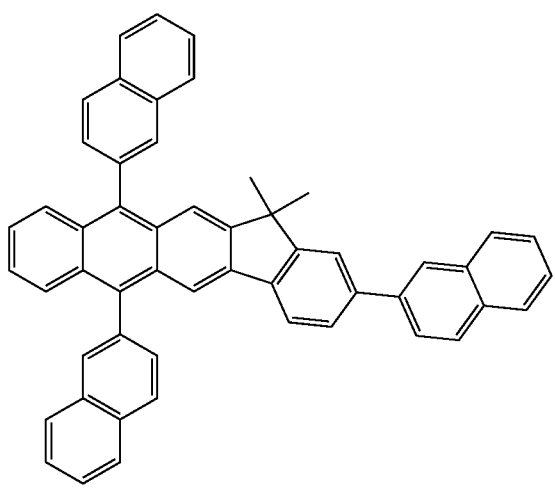
H40
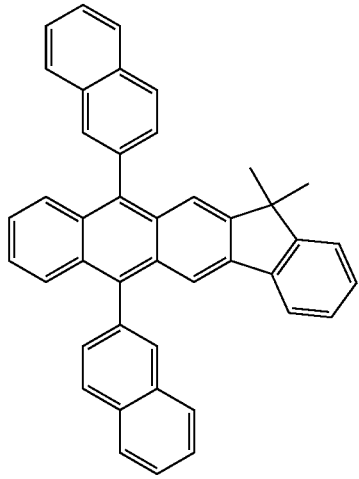
H41
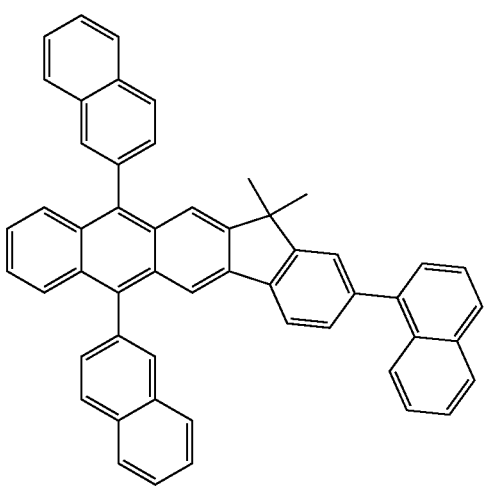
H42
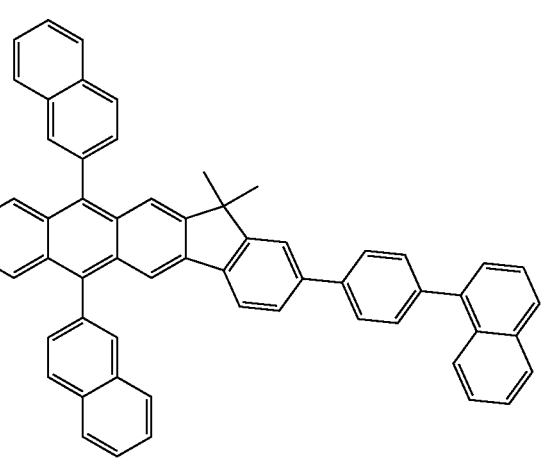
H39

In an implementation, the host may include at least one of Compounds H43 to H49.
H43
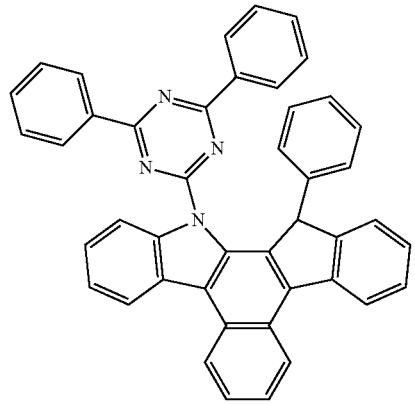
H44
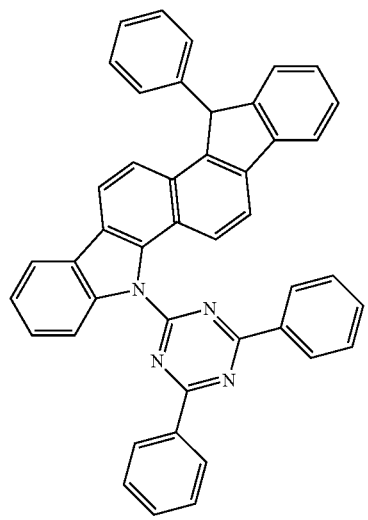
H45
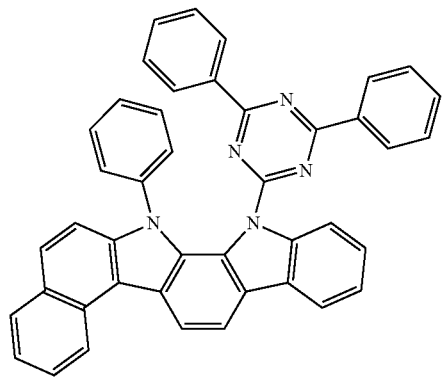
H46
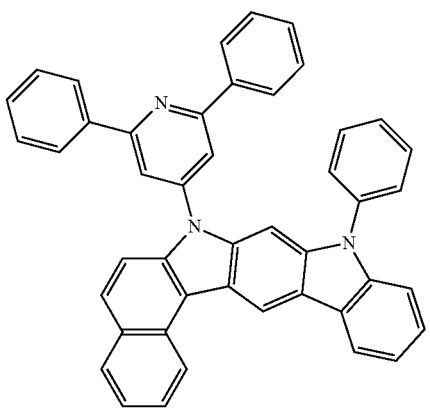
H47
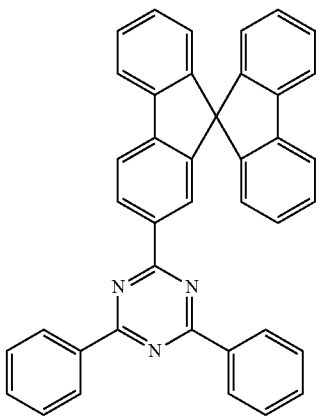
H48
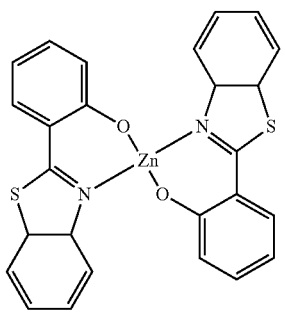
H49
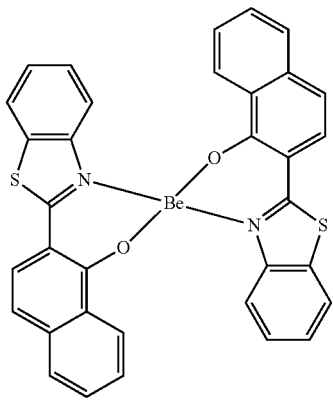

The dopant may include at least one of a fluorescent dopant and a phosphorescent dopant.

The phosphorescent dopant may include an organic metal complex represented by Formula 401:

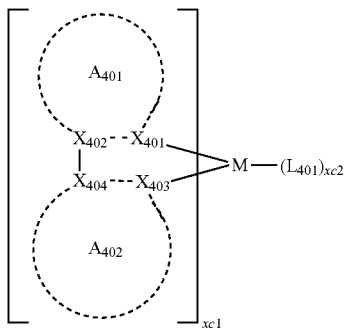

<Formula 401>

In Formula 401,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may each independently be nitrogen or carbon, rings $A_{401}$ and $A_{402}$ may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_2$-$C_{60}$ heteroaryl group, a monovalent non-aromatic condensed polycyclic group(non-aromatic condensed polycyclic group), a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$aryloxy group, a $C_6$-$C_{60}$arylthio group, a $C_2$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ may be an organic ligand, xc1 may be 1, 2, or 3; and xc2 may be 0, 1, 2, or 3.

In an example embodiment, $L_{401}$ may be a monovalent organic ligand, a divalent organic ligand, or a trivalent organic ligand. For example, $L_{401}$ may be selected from a halogen ligand (e.g., Cl or F), a diketone ligand (e.g., acetylacetonate, 1,3-diphenyl-1,3-propanedionate, 2,2,6,6-tetramethyl-3,5-heptanedionate, hexafluoroacetonate, carboxylic acid ligand (e.g., picolinate, dimethyl-3-pyrazolecarboxylate, or benzoate), a carbon monoxide ligand, an isonitrile ligand, a cyano ligand, and a phosphorus ligand (e.g., phosphine or phosphite).

When $A_{401}$ in Formula 401 has 2 or more substituents, 2 or more substituents of $A_{401}$ may be bonded to each other to form a saturated ring or an unsaturated ring.

When $A_{402}$ in Formula 401 has 2 or more substituents, 2 or more substituents of $A_{402}$ may be bonded to each other to form a saturated ring or an unsaturated ring.

When xc1 in Formula 401 is 2 or more, a plurality of ligands

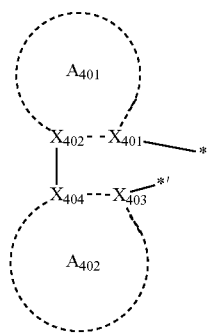

in Formula 401 may be identical to or different from each other. When xc1 in Formula 401 is 2 or more, $A_{401}$ and $A_{402}$ may be each independently bonded to $A_{401}$ and $A_{402}$ of other neighboring ligads, directly or via a linking group (e.g., a $C_1$-$C_5$ alkylene group, —N(R')— (wherein R' may be a $C_1$-$C_{10}$ alkyl group or a $C_6$-$C_{20}$ aryl group), or —C(=O)—).

The phosphorescent dopant may include at least one of Compounds PD1 to PD74.

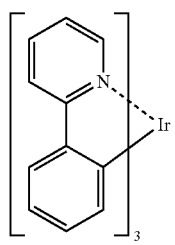

PD1

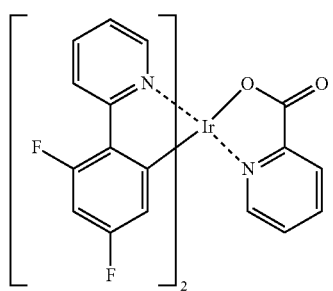

PD2

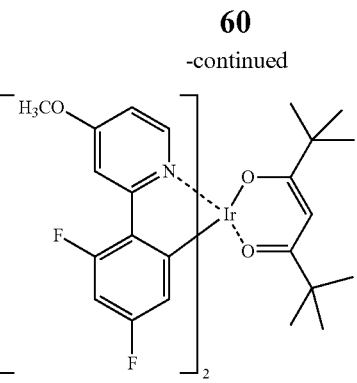

PD3

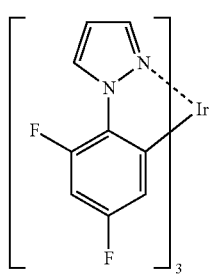

PD4

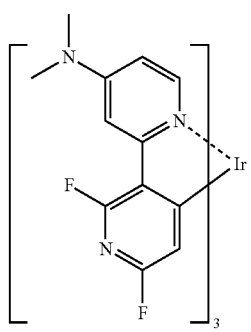

PD5

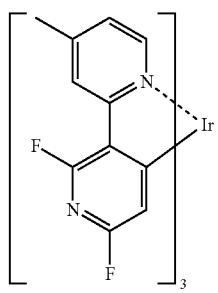

PD6

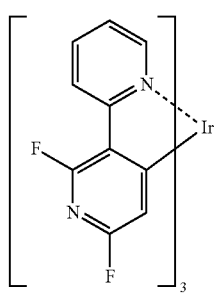

PD7

-continued
PD8
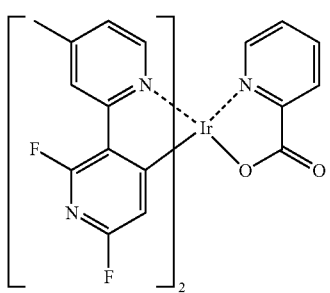
PD9
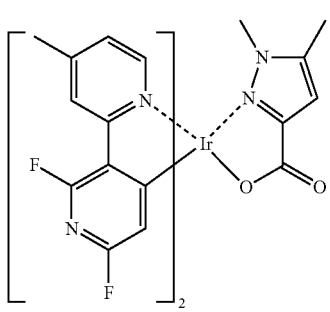
PD10
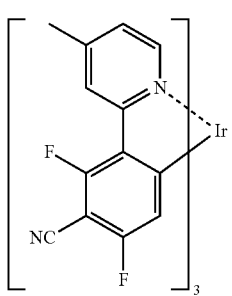
PD11
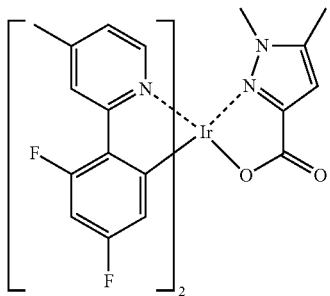
PD12
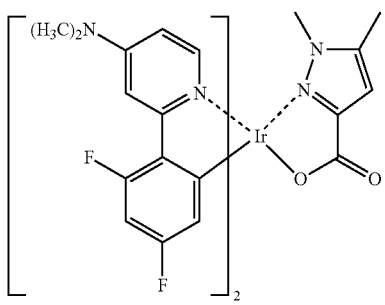
-continued
PD13
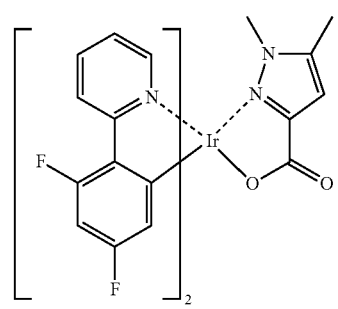
PD14
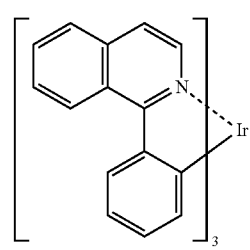
PD15
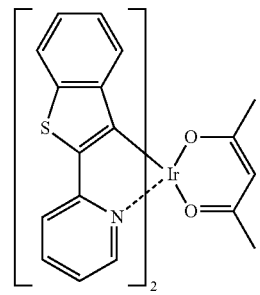
PD16
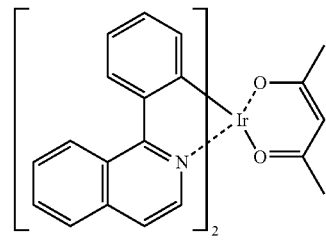
PD17
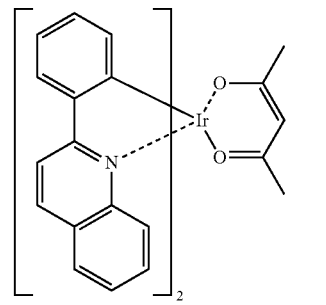

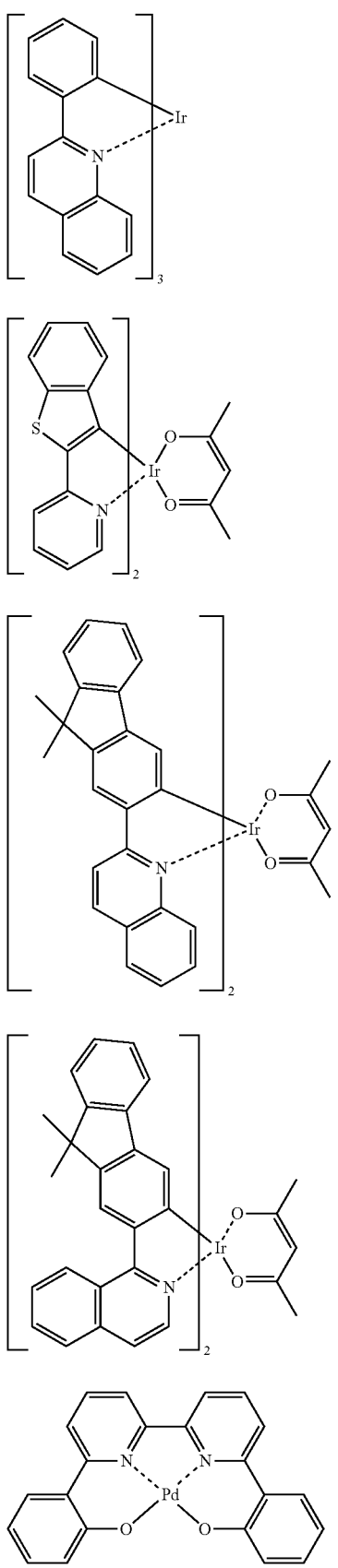
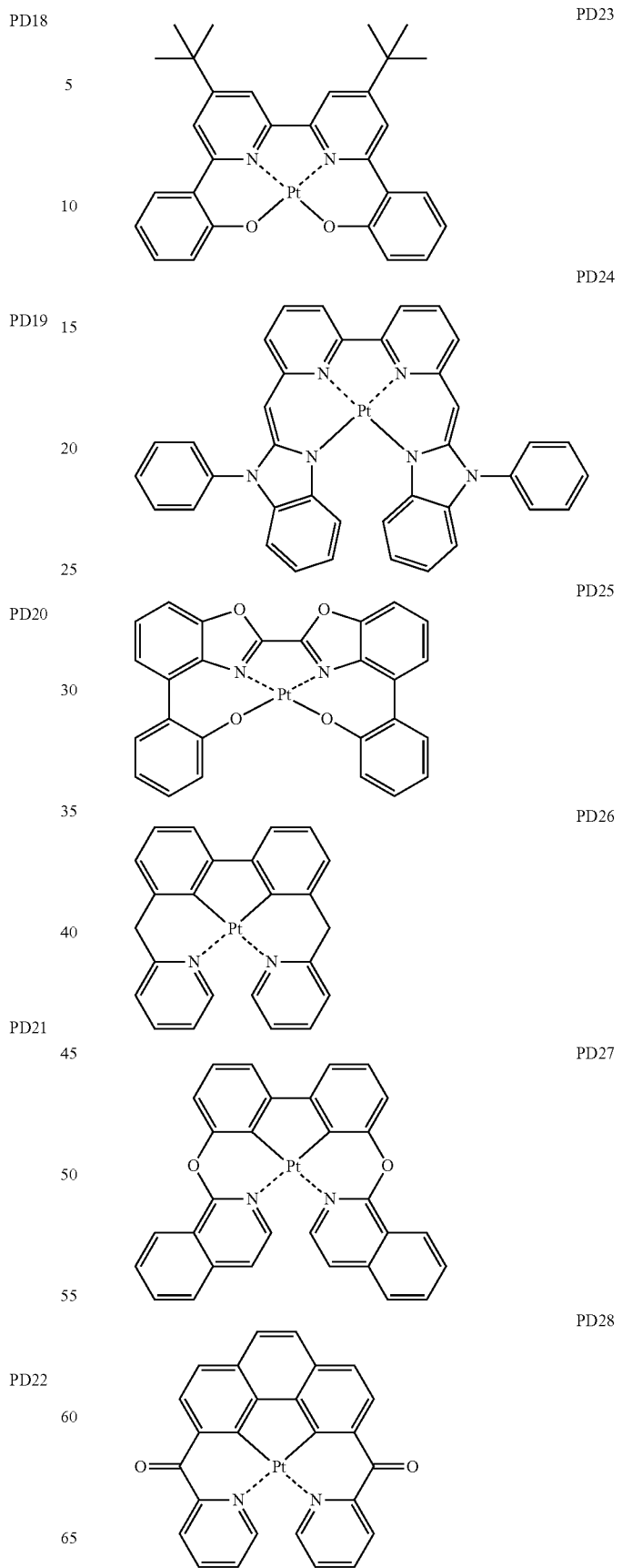

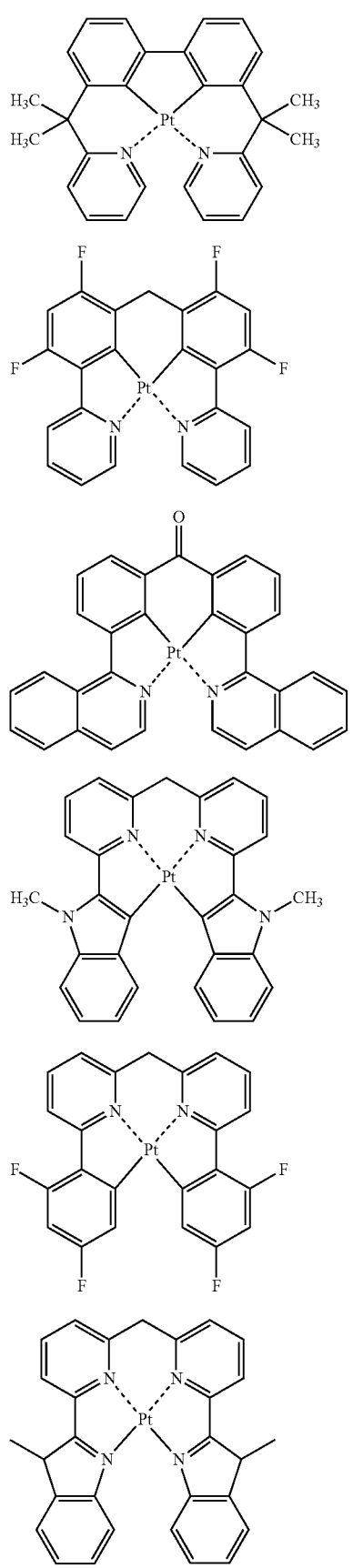
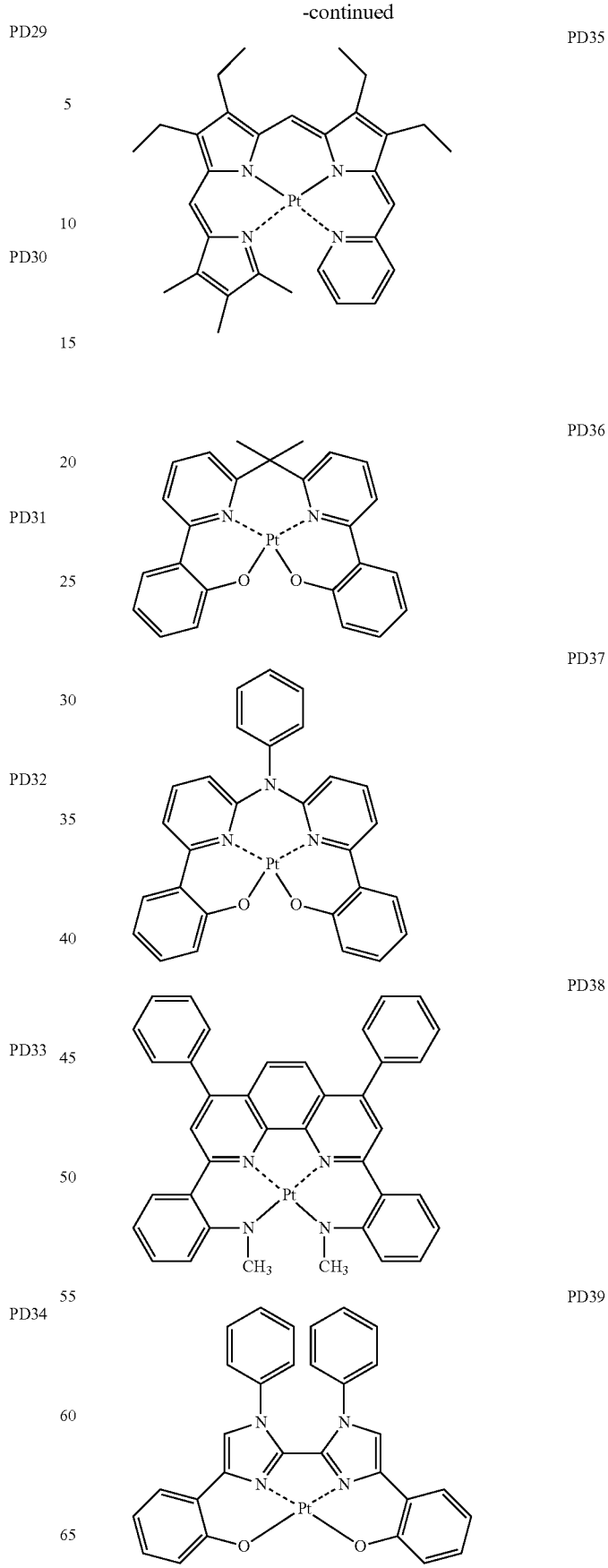

PD40 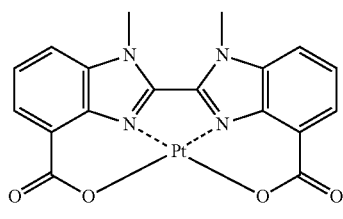
PD45 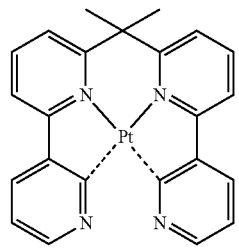
PD41 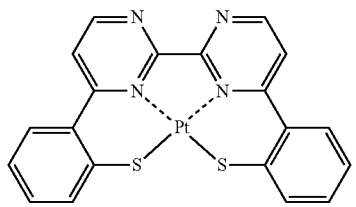
PD46 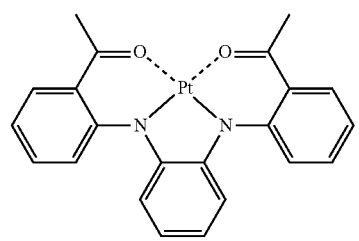
PD42 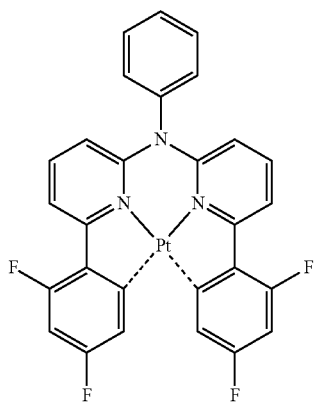
PD47 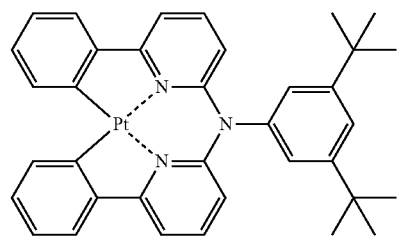
PD48 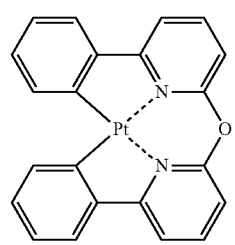
PD43 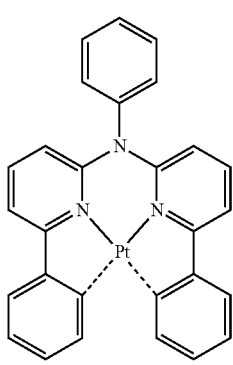
PD49 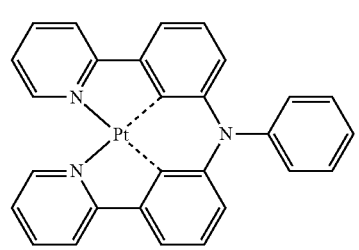
PD44 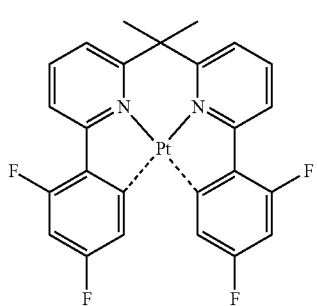
PD50 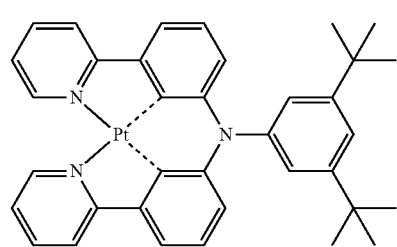

-continued
PD51
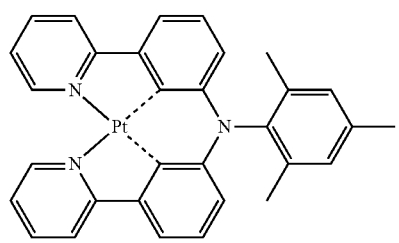
PD52
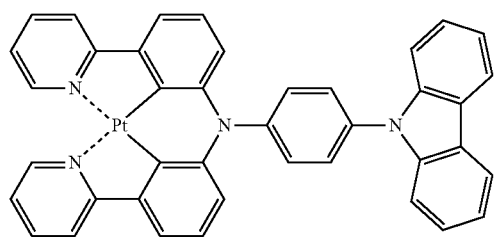
PD53
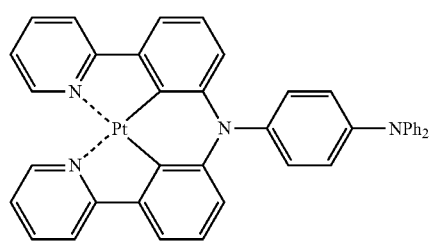
PD54
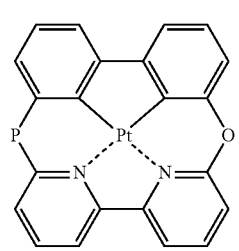
PD55
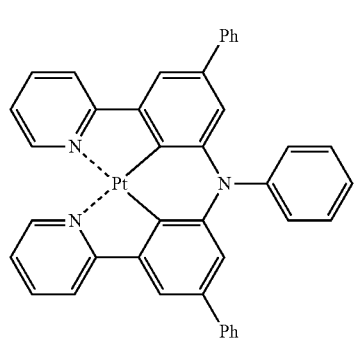
PD56
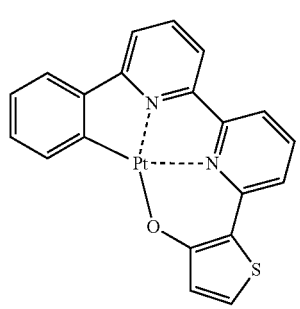
-continued
PD57
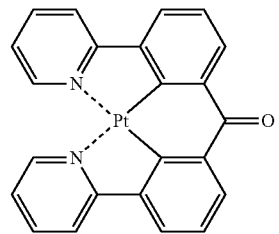
PD58
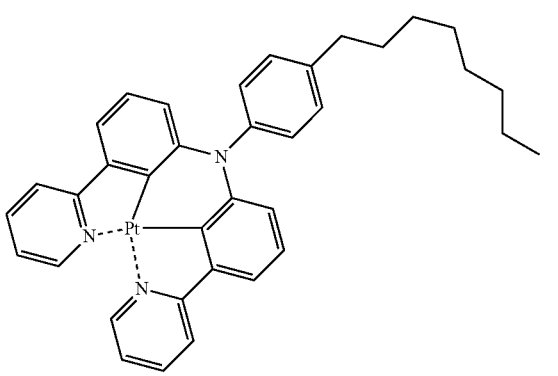
PD59
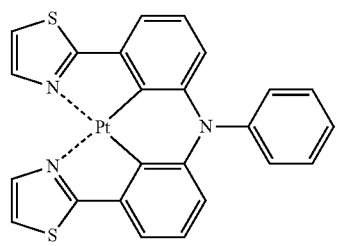
PD60
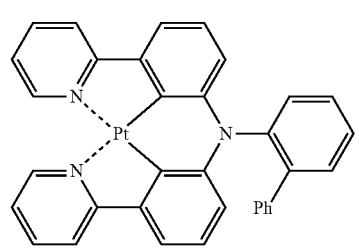
PD61
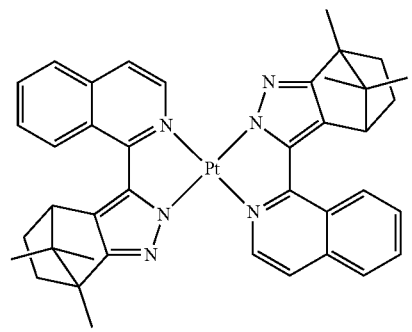

PD62 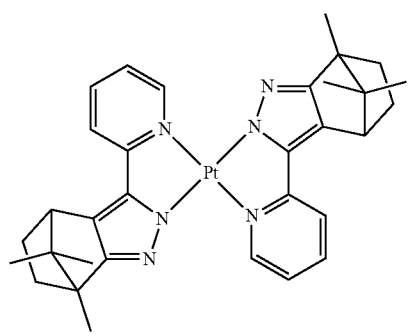
PD63 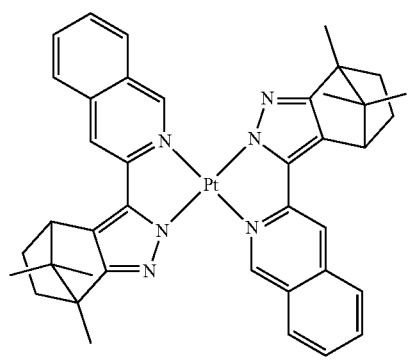
PD64 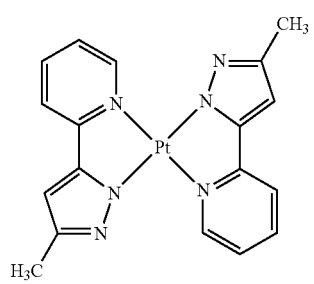
PD65 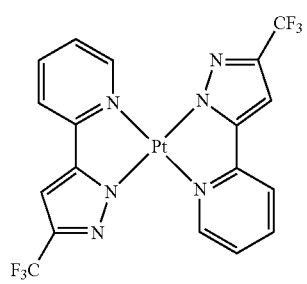
PD66 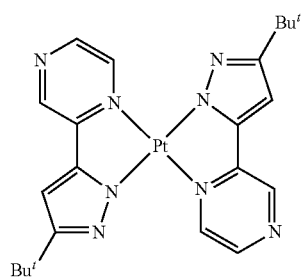
PD67 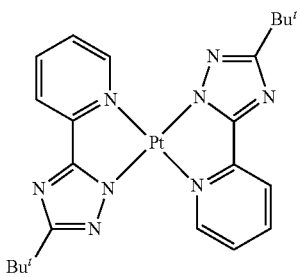
PD68 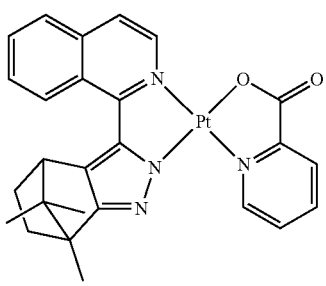
PD69 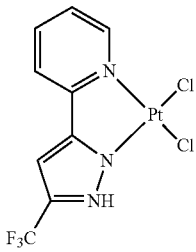
PD70 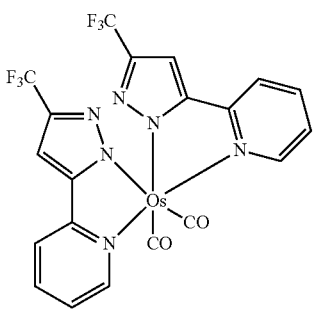
PD71 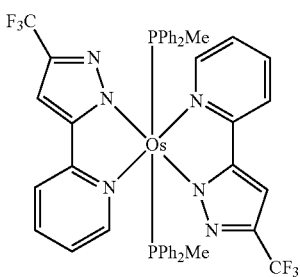

PD72
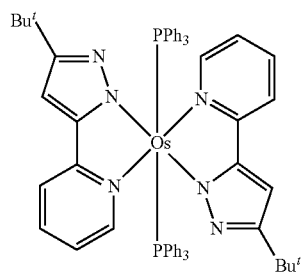
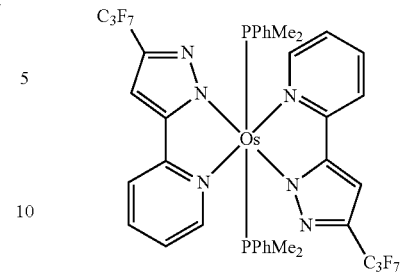
In an implementation, the phosphorescent dopant may include PtOEP:
PD73
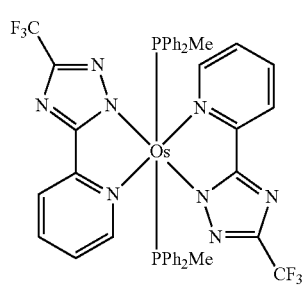
PtOEP
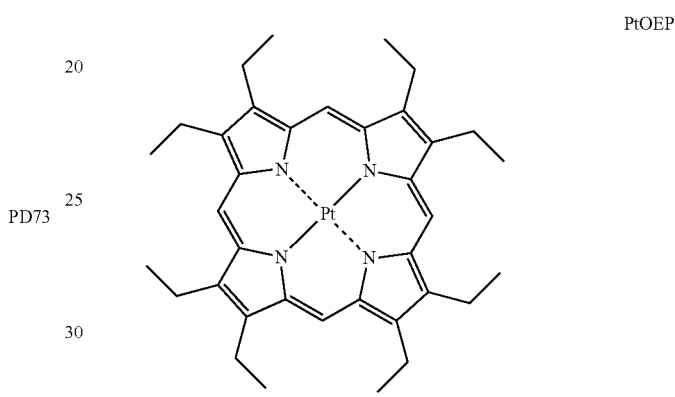
The fluorescent dopant may include at least one of DPAVBi, BDAVBi, TBPe, DCM, DCJTB, Coumarin 6, and C545T:
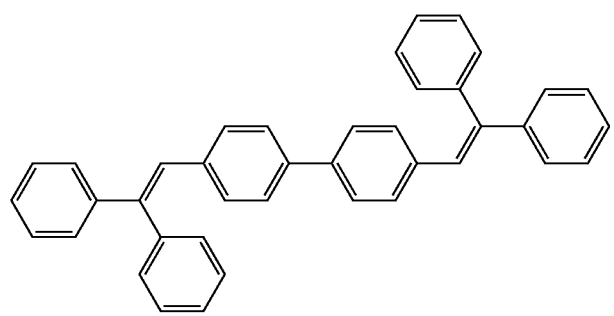
DPVBi
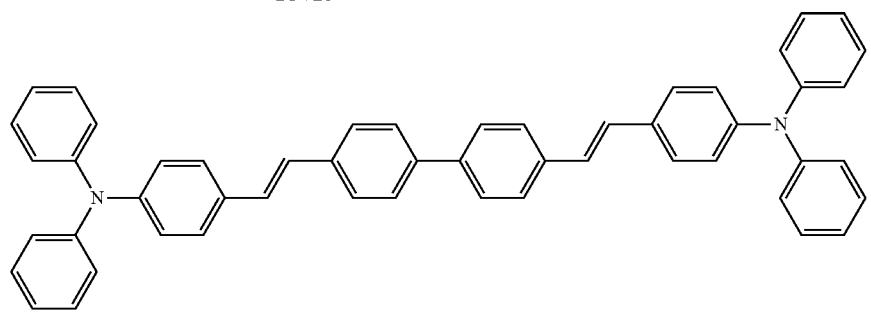
DPAVBi

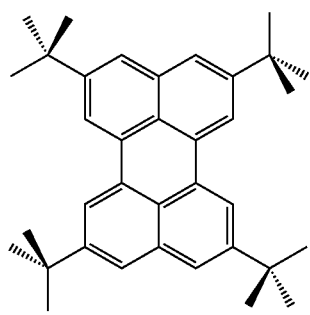

TBPe

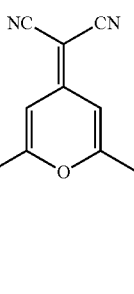

DCM

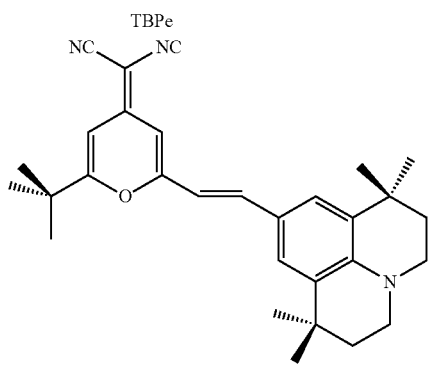

DCJTB

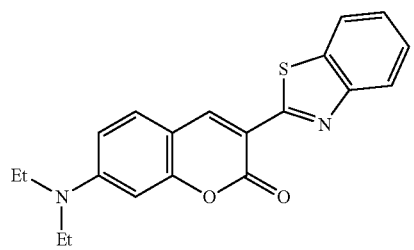

Coumarin 6

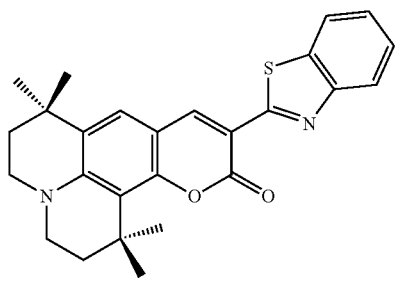

C545T

In an implementation, the fluorescent dopant may include a compound represented by Formula 501:

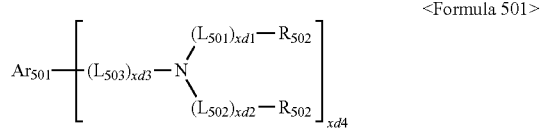

<Formula 501>

In Formula 501, $Ar_{501}$ may be selected from:

a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), $L_{501}$ to $L_{503}$ may each independently be the same as defined in connection with $L_{301}$ in the present specification, $R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3, and xb4 may be selected from 1, 2, 3, and 4.

The fluorescent dopant may include at least one of Compounds FD1 to FD8:

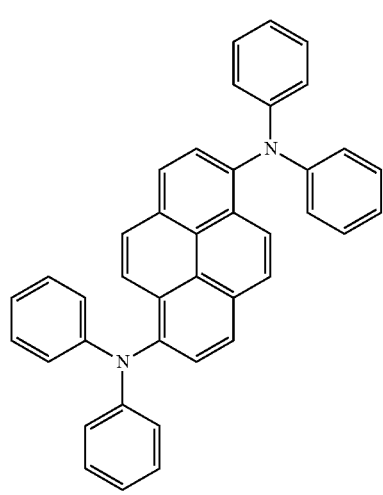

FD1

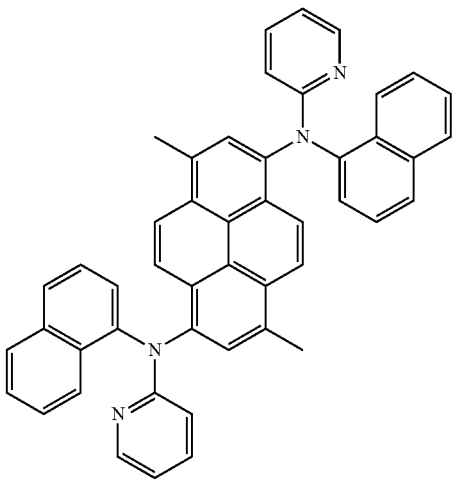

FD2

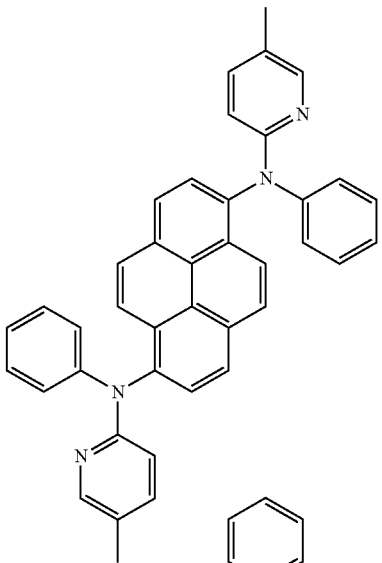

FD3

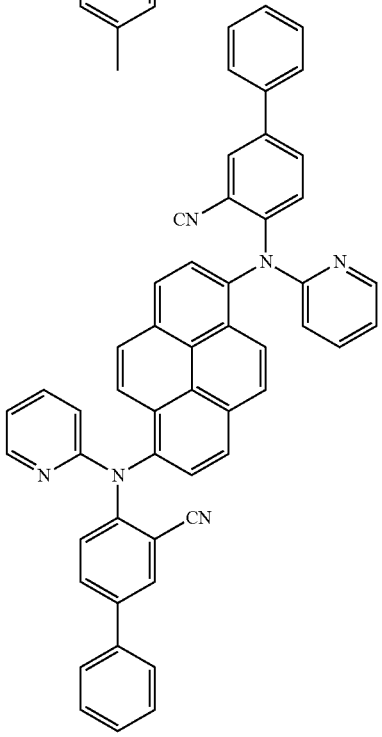

FD4

FD5

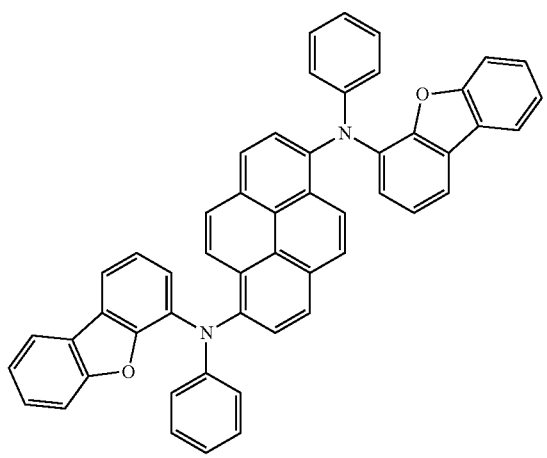

FD6

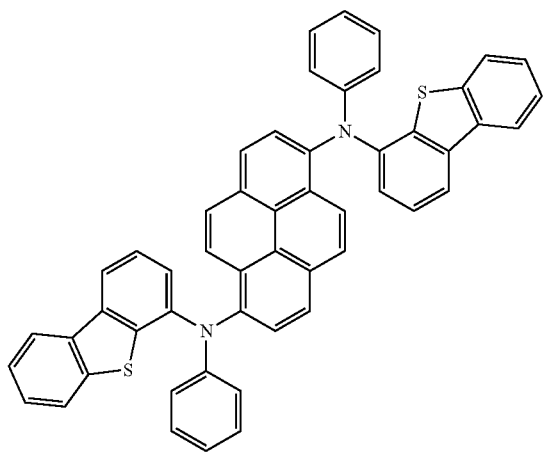

FD7

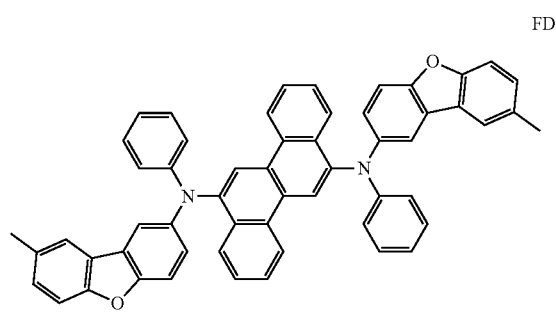

FD8

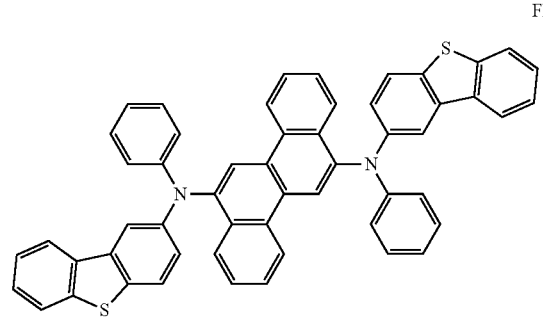

An amount of the dopant included in the emission layer may be from about 0.01 to about 15 parts by weight, based on 100 parts by weight of the host.

A thickness of the emission layer may be from about 100 Å to about 1,000 Å, e.g., about 200 Å to about 600 Å. When the thickness of the emission layer is within these ranges, excellent emission characteristics may be obtained without a substantial increase in driving voltage.

Next, the electron transport region may be disposed on the emission layer.

The electron transport region may include at least one of an HBL, an ETL, and an EIL.

When the electron transport region includes the HBL, the HBL may be formed on the emission layer by using various suitable methods, such as vacuum deposition, spin coating, casting, a LB method, ink-jet printing, laser-printing, or LITI. When the HBL is formed by vacuum deposition or by spin coating, the deposition conditions or the coating conditions may be inferred based on the deposition conditions or the coating conditions for forming the HIL.

The HBL may include, e.g., at least one of BCP and Bphen.

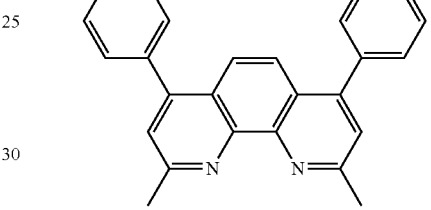

BCP

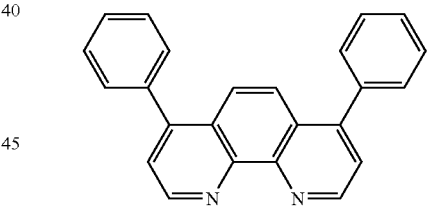

Bphen

A thickness of the HBL may be from about 20 Å to about 1,000 Å, e.g., about 30 Å to about 300 Å. When the thickness of the HBL is within these ranges, excellent hole blocking characteristics may be obtained without a substantial increase in driving voltage.

The electron transport region may have a structure of ETL/EIL or a structure of HBL/ETL/EIL, each of which layers are sequentially stacked in the stated order from the emission layer.

In an exemplary embodiment, the organic layer 150 may include the electron transport region that is disposed between the emission layer and the second electrode 190, and the electron transport region may include an ETL. In an implementation, the ETL may consist of a plurality of layers. For example, the electron transport region may include a first ETL and a second ETL.

The ETL may include at least one of BCP, Bphen, Alq$_3$, Balq, TAZ, and NTAZ:

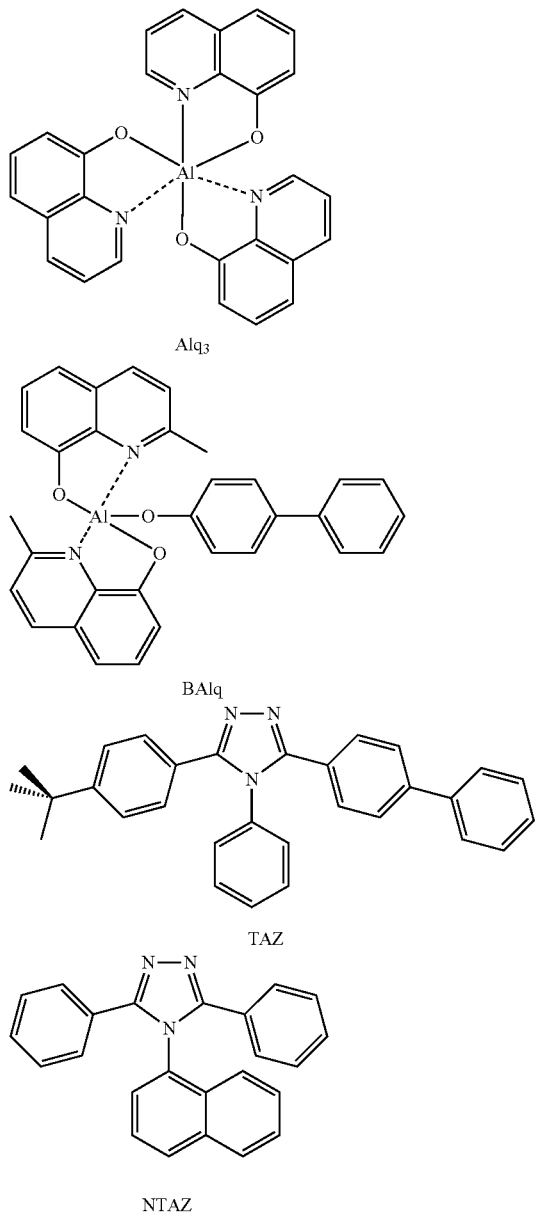

Alq$_3$

BAlq

TAZ

NTAZ

Alternatively, the ETL may include at least one of a compound represented by Formula 601 and a compound represented by Formula 602:

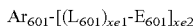 <Formula 601>

In Formula 601,

Ar$_{601}$ may be selected from:

a naphthalene, a heptalene, a fluorene, a Spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_3$-C$_{10}$ heterocycloalkyl group, a C$_3$-C$_{10}$ cycloalkenyl group, a C$_3$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, a monovalent non-aromatic condensed heteropolycyclic group, and —Si(Q$_{301}$)(Q$_{302}$)(Q$_{303}$) (wherein Q$_{301}$ to Q$_{303}$ may be each independently selected from a hydrogen, a C$_1$-C$_{60}$ alkyl group, a C$_2$-C$_{60}$ alkenyl group, a C$_6$-C$_{60}$ aryl group, and a C$_2$-C$_{60}$ heteroaryl group);

L$_{601}$ may be the same as defined in connection with L$_{301}$;

E$_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3, and xe2 may be selected from 1, 2, 3, and 4.

<Formula 602>

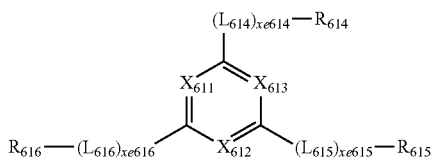

In Formula 602, $X_{611}$ may be N or C-$(L_{611})_{xe611}$-$R_{611}$, $X_{612}$ may be N or C-$(L_{612})_{xe612}$-$R_{612}$, and $X_{613}$ may be N or C-$(L_{613})_{xe613}$-$R_{613}$, where at least one of $X_{611}$ to $X_{613}$ may be N, $L_{611}$ to $L_{616}$ may each independently be the same as defined in connection with $L_{301}$, $R_{611}$ to $R_{616}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xe611 to xe616 may each independently be selected from 0, 1, 2, and 3.

The compound of Formula 601 and the compound of Formula 602 may be selected from Compounds ET 1 to ET 15:

ET1

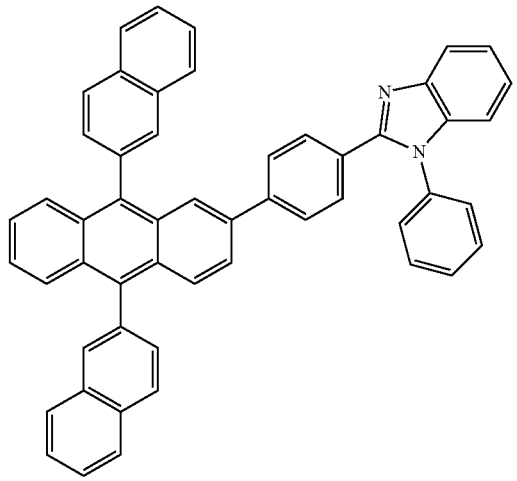

ET2

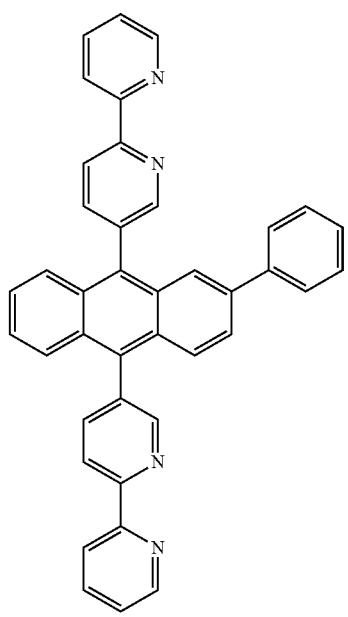

ET3
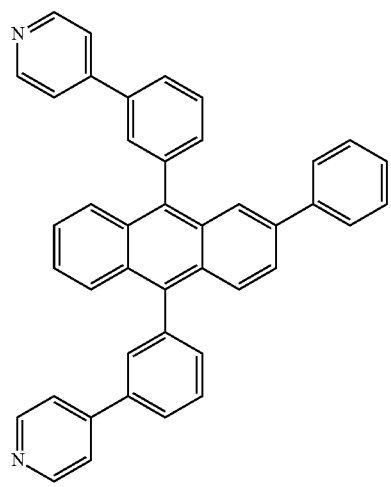
ET7
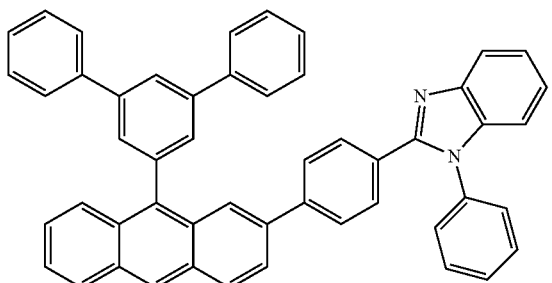
ET4
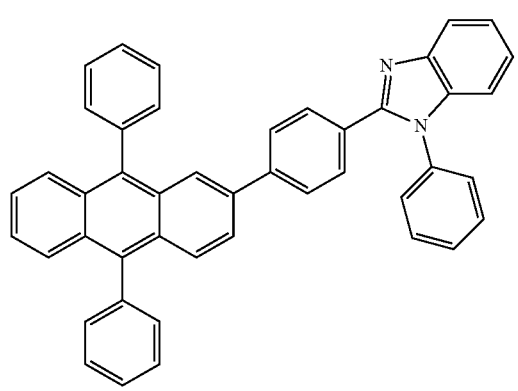
ET8
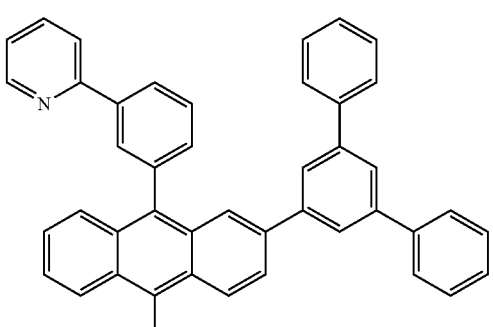
ET5
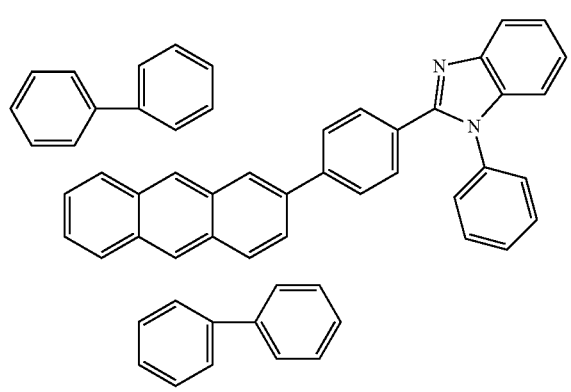
ET6
ET9
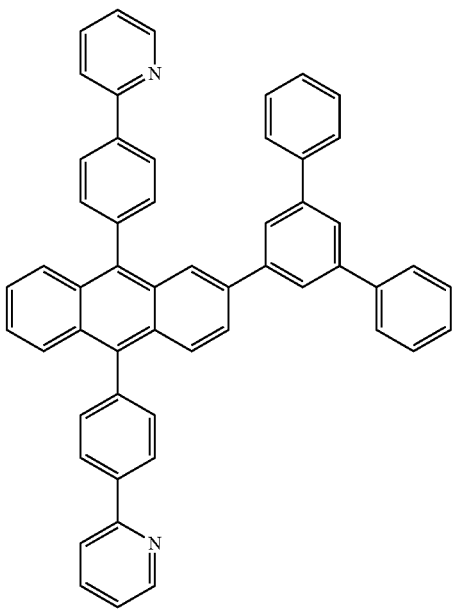

ET10

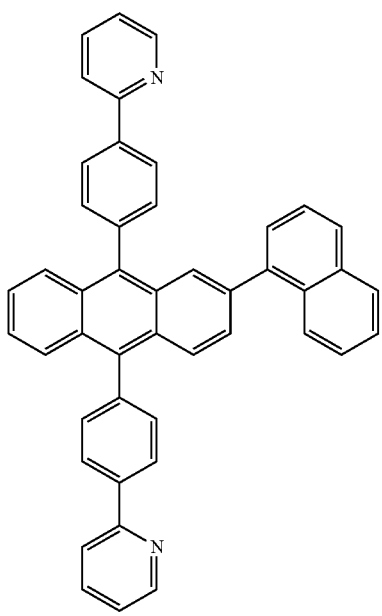

ET11

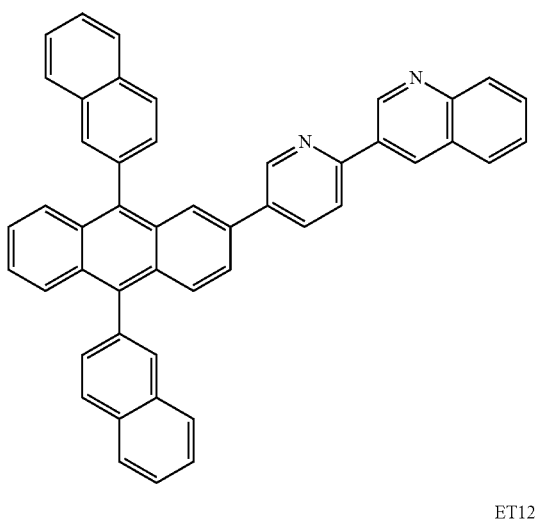

ET12

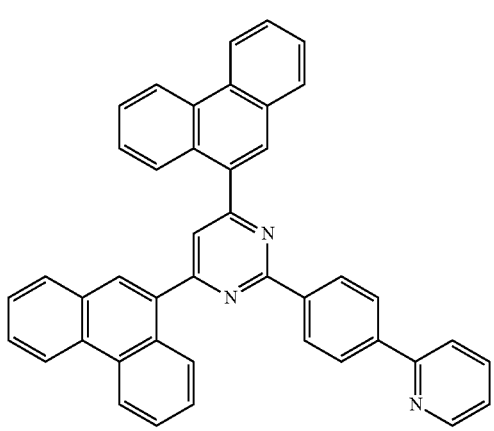

ET13

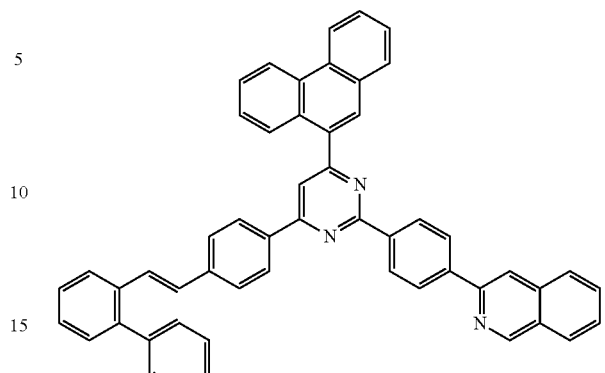

ET14

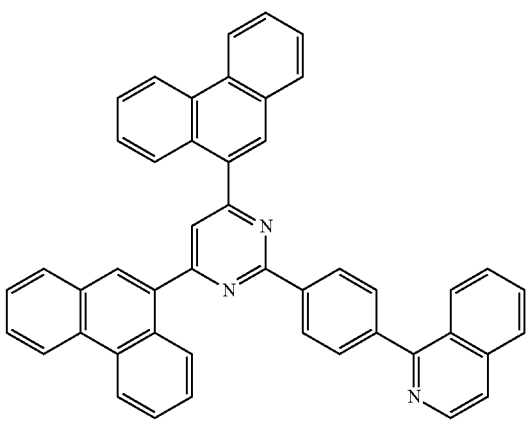

ET15

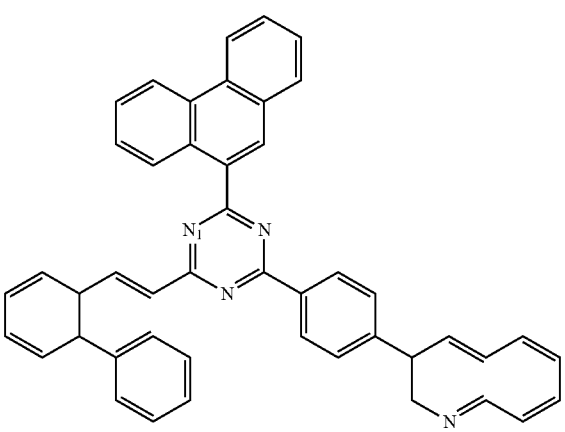

A thickness of the ETL may be from about 100 Å to about 1,000 Å, e.g., about 150 Å to about 500 Å. When the thickness of the ETL is within these ranges, excellent electron transporting characteristics may be obtained without a substantial increase in driving voltage.

The ETL may further include, in addition to the materials described above, a metal-containing material.

The metal-containing material may include a Li complex. The Li complex may include, e.g., Compound ET-D1 (e.g., lithium quinolate (LiQ)) or ET-D2.

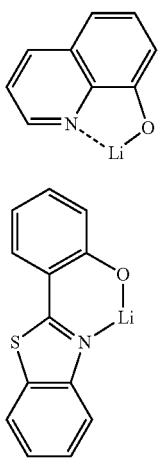

ET-D1

ET-D2

The electron transport region may include an EIL that facilitates electron injection from the second electrode 190.

The EIL may be formed on the ETL by using various suitable methods, such as vacuum deposition, spin coating, casting, a LB method, ink-jet printing, laser-printing, or LITI. When the EIL is formed by vacuum deposition or by spin coating, the deposition conditions or the coating conditions may be inferred based on the deposition conditions or the coating conditions for forming the HIL.

The EIL may include at least one selected from LiF, NaCl, CsF, $Li_2O$, BaO, and LiQ.

A thickness of the EIL may be from about 1 Å to about 100 Å, e.g., about 3 Å to about 90 Å. When the thickness of the EIL is within these ranges, suitable or satisfactory electron injecting characteristics may be obtained without a substantial increase in driving voltage.

The second electrode 190 may be disposed on the organic layer 150. The second electrode 190 may be a cathode, which is an electron injection electrode. Here, a material for forming the second electrode 190 may be a material having a low work function, such as a metal, an alloy, an electrically conductive compound, or a mixture thereof. Examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In an implementation, the material for forming the second electrode 190 may include ITO or IZO. The second electrode 190 may be a reflective electrode, a semi-transmissive electrode, or a transmissive electrode.

In an implementation, the organic layer 150 of the organic light-emitting device 10 may be formed by a deposition method using compounds according to an exemplary embodiment, or by a wet coating method using compounds that are prepared in solutions according to an exemplary embodiment.

The organic light-emitting device 10 according to an exemplary embodiment may be included in various types of flat panel display apparatus, such as a passive matrix OLED display apparatus and an active matrix OLED display apparatus. For example, when the organic light-emitting device 10 is equipped with the active matrix OLED display apparatus, the first electrode may be disposed on a side of the substrate, and as a pixel electrode, the first electrode may be electrically coupled to source and drain electrodes of a thin film transistor. In addition, the organic light-emitting device 10 may be equipped with a flat panel display apparatus that can display screens at both sides.

Hereinbefore, the organic light-emitting device 10 has been described in connection with the FIGURE.

Hereinafter, representative substituents among all of the substituents used in the present specification may be defined as follows (carbon numbers limiting the substituents are non-limiting and do not limit characteristics of the substituents, and substituents that are not described in the present specification are not included if found in general definitions of the substituents).

A $C_1$-$C_{60}$ alkyl group as used herein refers to a linear or branched aliphatic hydrocarbon monovalent group having 1 to 60 carbon atoms, and detailed examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group), and detailed examples thereof include a methoxy group, an ethoxy group, and an isopropyloxy group.

A $C_2$-$C_{60}$ alkenyl group as used herein refers to a hydrocarbon group formed by substituting at least one carbon double bond in a middle chain or terminal end of the $C_2$-$C_{60}$ alkyl group, and detailed examples thereof include an ethenyl group, a prophenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by substituting at least one carbon triple bond in a middle chain or terminal end of the $C_2$-Cal alkyl group, and detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms, and detailed examples thereof include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms, and detailed examples thereof include a tetrahydrofuranyl group and a tetrahydrothiophenyl group. A $C_2$-$C_{10}$ heterocycloalkylene group as used herein refers to a divalent group having the same structure as the $C_2$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof and does not have aromaticity, and detailed examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_2$-$C_{10}$ heterocycloalkenyl group as used herein refers to a monovalent monocyclic group that has at least one heteroatom selected from N, O, P, and S as a ring-forming atom, 1 to 10 carbon atoms, and at least one double bond in its ring. Detailed examples of the $C_2$-$C_{10}$ heterocycloalkenyl group include a 2,3-hydrofuranyl group and a 2,3-hydrothiophenyl group. A $C_2$-$C_{10}$ heterocycloalkenylene group as used herein refers to a divalent group having the same structure as the $C_2$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, these rings may be fused to each other.

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, these rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) as used herein refers to a monovalent group that has two or more rings condensed to each other, has carbon atoms only as a ring-forming atom, and has non-aromaticity in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group (e.g., a group having 2 to 60 carbon atoms) as used herein refers to a monovalent group that has two or more rings condensed to each other, has heteroatoms as a ring-forming atom selected from N, O, P, and S, in addition to C, and has non-aromaticity in the entire molecular structure. A detailed example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ hetero-cycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one of substituents of the $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{ti}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The term "Ph" as used herein refers to a phenyl group, the term "Me" as used herein refers to a methyl group, the term "Et" as used herein refers to an ethyl group, and the term "ter-Bu" or "Bu$^t$" as used herein refers to a tert-butyl group.

Hereinafter an organic light-emitting device according to an embodiment will be described in detail with reference to Synthesis Examples and Examples.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

Synthesis Example 1: Synthesis of Compound 4

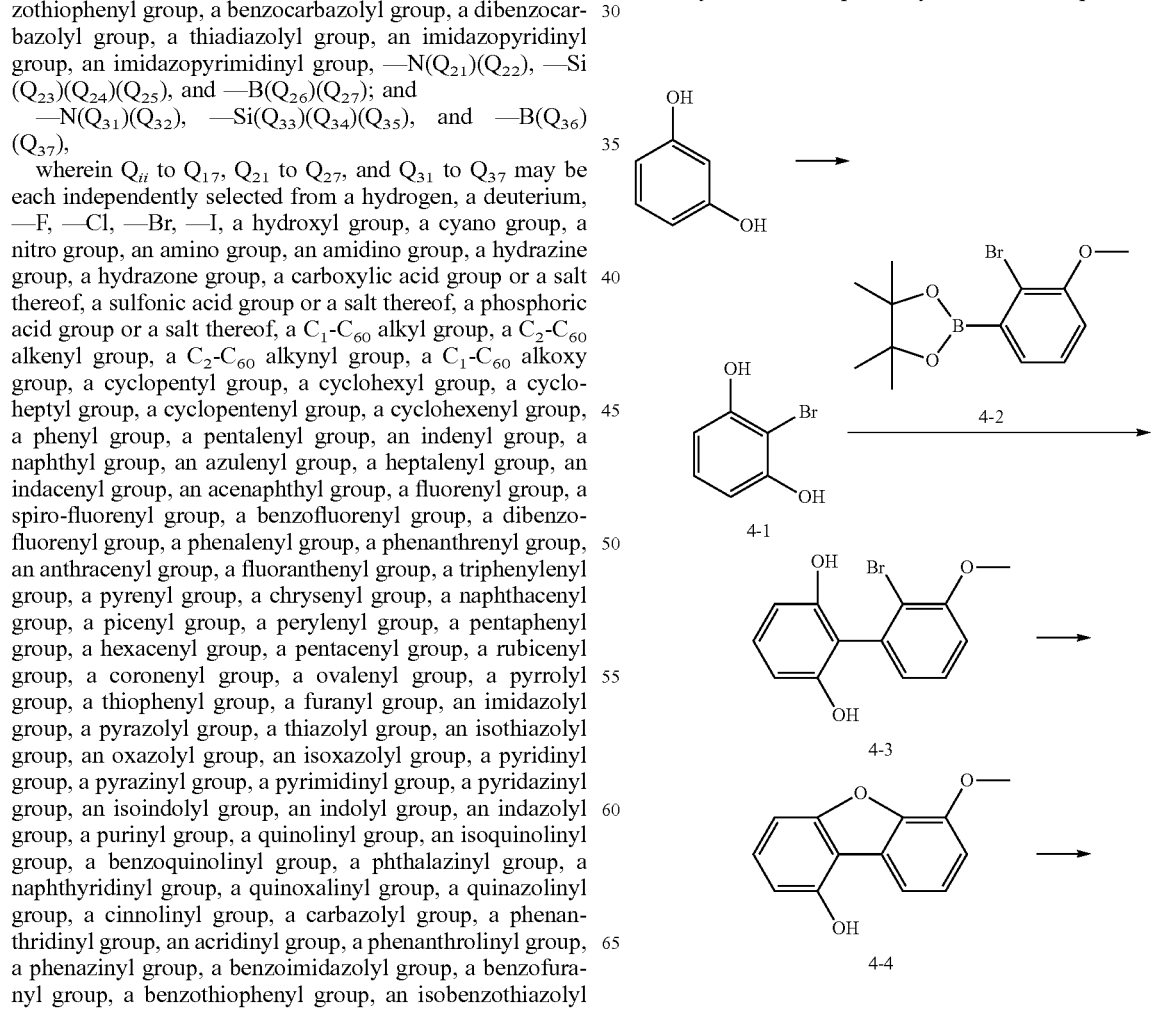

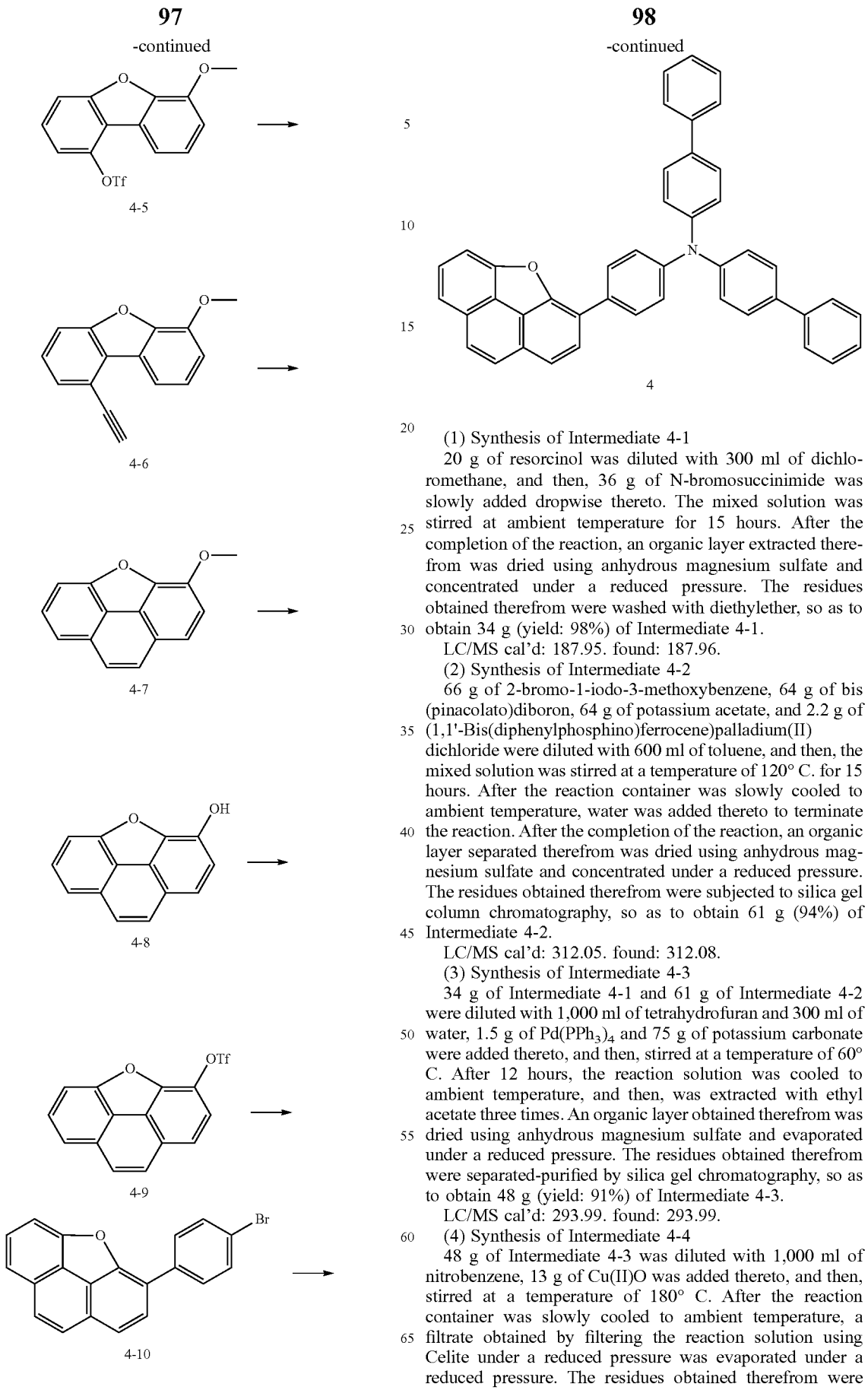

(1) Synthesis of Intermediate 4-1

20 g of resorcinol was diluted with 300 ml of dichloromethane, and then, 36 g of N-bromosuccinimide was slowly added dropwise thereto. The mixed solution was stirred at ambient temperature for 15 hours. After the completion of the reaction, an organic layer extracted therefrom was dried using anhydrous magnesium sulfate and concentrated under a reduced pressure. The residues obtained therefrom were washed with diethylether, so as to obtain 34 g (yield: 98%) of Intermediate 4-1.

LC/MS cal'd: 187.95. found: 187.96.

(2) Synthesis of Intermediate 4-2

66 g of 2-bromo-1-iodo-3-methoxybenzene, 64 g of bis(pinacolato)diboron, 64 g of potassium acetate, and 2.2 g of (1,1'-Bis(diphenylphosphino)ferrocene)palladium(II) dichloride were diluted with 600 ml of toluene, and then, the mixed solution was stirred at a temperature of 120° C. for 15 hours. After the reaction container was slowly cooled to ambient temperature, water was added thereto to terminate the reaction. After the completion of the reaction, an organic layer separated therefrom was dried using anhydrous magnesium sulfate and concentrated under a reduced pressure. The residues obtained therefrom were subjected to silica gel column chromatography, so as to obtain 61 g (94%) of Intermediate 4-2.

LC/MS cal'd: 312.05. found: 312.08.

(3) Synthesis of Intermediate 4-3

34 g of Intermediate 4-1 and 61 g of Intermediate 4-2 were diluted with 1,000 ml of tetrahydrofuran and 300 ml of water, 1.5 g of Pd(PPh$_3$)$_4$ and 75 g of potassium carbonate were added thereto, and then, stirred at a temperature of 60° C. After 12 hours, the reaction solution was cooled to ambient temperature, and then, was extracted with ethyl acetate three times. An organic layer obtained therefrom was dried using anhydrous magnesium sulfate and evaporated under a reduced pressure. The residues obtained therefrom were separated-purified by silica gel chromatography, so as to obtain 48 g (yield: 91%) of Intermediate 4-3.

LC/MS cal'd: 293.99. found: 293.99.

(4) Synthesis of Intermediate 4-4

48 g of Intermediate 4-3 was diluted with 1,000 ml of nitrobenzene, 13 g of Cu(II)O was added thereto, and then, stirred at a temperature of 180° C. After the reaction container was slowly cooled to ambient temperature, a filtrate obtained by filtering the reaction solution using Celite under a reduced pressure was evaporated under a reduced pressure. The residues obtained therefrom were separated-purified by silica gel chromatography, so as to obtain 34 g (yield: 98%) of Intermediate 4-4.

LC/MS cal'd: 214.06. found: 214.08.

(5) Synthesis of Intermediate 4-5

34 g of Intermediate 4-4 was diluted with 600 ml of dichloromethane, and then, 31 ml of triethylamine was slowly added dropwise thereto. Continuously, 48 g of anhydrous trifluoroacetic acid was slowly added dropwise thereto at a temperature of 0° C. After the mixed solution was stirred at ambient temperature for 3 hours, water was added thereto to terminate the reaction. After the completion of the reaction, an organic layer separated therefrom was dried using anhydrous magnesium sulfate and concentrated under a reduced pressure. The residues obtained therefrom were subjected to silica gel chromatography, so as to obtain 53 g (96%) of Intermediate 4-5.

LC/MS cal'd: 346.01. found: 346.03.

(6) Synthesis of Intermediate 4-6

53 g of Intermediate 4-5 was diluted with 500 ml of tetrahydrofuran, and 30 g of ethynyltrimethylsilane, 64 ml of triethylamine, 3.1 g of bis(triphenylphosphine)palladium(II) dichloride, and 1.5 g of CuI were sequentially added thereto. The mixed solution was stirred at a temperature of 60° C. for 6 hours. After the reaction container was cooled to a temperature of 0° C., 60 ml of conc. hydrochloric acid was slowly added dropwise thereto. After the mixed solution was stirred at ambient temperature for 1 hour, the mixed solution was diluted with water. After the mixed solution was stirred at ambient temperature for 3 hours, water was added thereto to terminate the reaction. An organic layer obtained therefrom was dried using anhydrous magnesium sulfate and concentrated under a reduced pressure. The residues obtained therefrom were subjected to silica gel chromatography, so as to obtain 30 g (yield: 87%) of Intermediate 4-6.

LC/MS cal'd: 222.07. found: 222.07.

(7) Synthesis of Intermediate 4-7

30 g of Intermediate 4-6 was diluted with 300 ml of toluene, and 1.8 g of PtCl$_2$ was added thereto. The mixed solution was stirred at a temperature of 80° C. for 15 hours, and then, cooled to ambient temperature. Water was added thereto to terminate the reaction. An organic layer obtained therefrom was dried using anhydrous magnesium sulfate and concentrated under a reduced pressure. The residues obtained therefrom were subjected to silica gel chromatography, so as to obtain 28 g (yield: 93%) of Intermediate 4-6.

LC/MS cal'd: 222.07. found: 222.08.

(8) Synthesis of Intermediate 4-8

28 g of Intermediate 4-7 was diluted with 500 ml of dichloromethane, and then, 18 ml of tribromoboron was slowly added dropwise thereto. After 3 hours, a saturated sodium bicarbonate solvent was added thereto to terminate the reaction at a temperature of 0° C., thereby separating layers. An organic layer obtained therefrom was dried using anhydrous magnesium sulfate and concentrated under a reduced pressure. The residues obtained therefrom were subjected to silica gel chromatography, so as to obtain 23 g (yield: 89%) of Intermediate 4-8.

LC/MS cal'd: 208.05. found: 208.08.

(9) Synthesis of Intermediate 4-9

36 g (yield: 96%) of Intermediate 4-9 was obtained in the same manner as in Synthesis of Intermediate 4-5, except that 23 g of Intermediate 4-8 was used.

LC/MS cal'd: 340.00. found: 340.01.

(10) Synthesis of Intermediate 4-10

2.7 g (yield: 82%) of Intermediate 4-10 was obtained in the same manner as in Synthesis of Intermediate 4-3, except that 4 g of Intermediate 4-9 and 2.4 g of (4-bromophenyl)boronic acid were used.

LC/MS cal'd: 281.85. found: 281.86.

(11) Synthesis of Compound 4

2.7 g of Intermediate 4-10, 2.5 g of di([1,1'-biphenyl]-4-yl)amine, 0.35 g of Pd$_2$(dba)$_3$, 0.12 ml of PtBu$_3$, and 2.6 g of KOtBu were dissolved in 50 ml of toluene, and then, the mixed solution was stirred at a temperature of 85° C. for 2 hours. Water was added thereto to terminate the reaction at ambient temperature, and then, the reaction solution was extracted with ethyl acetate three times. An organic layer obtained therefrom was dried using anhydrous magnesium sulfate and evaporated under a reduced pressure. The residues were separated-purified by silica gel chromatography, so as to obtain 3.8 g (yield: 83%) of Compound 4.

LC/MS cal'd: 587.22. found: 587.24.

Synthesis Example 2: Synthesis of Compound 21

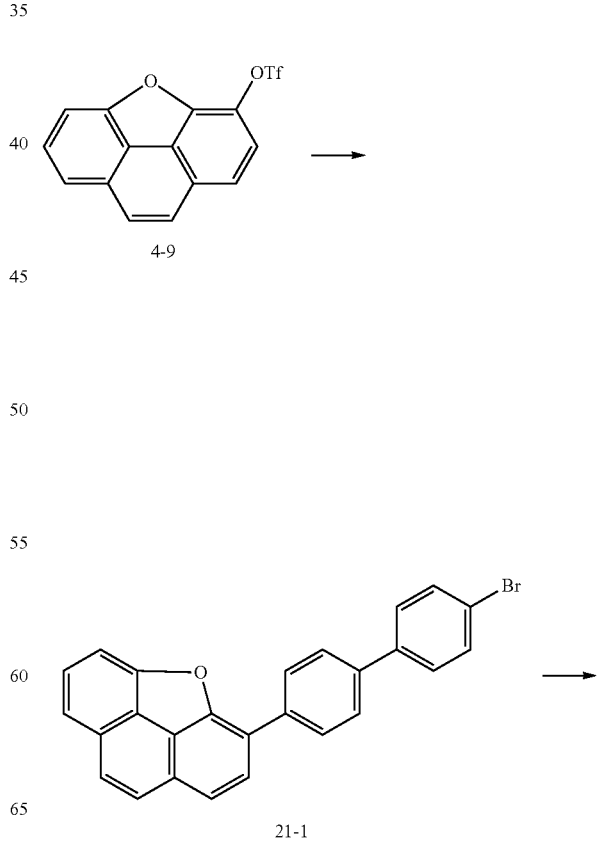

g of Intermediate 4-10 and 3.4 g of N-([1,1'-biphenyl]-4-yl)dibenzo[b,d]furan-3-amine were used.

LC/MS cal'd: 601.20. found: 601.21.

Synthesis Example 4: Synthesis of Compound 33

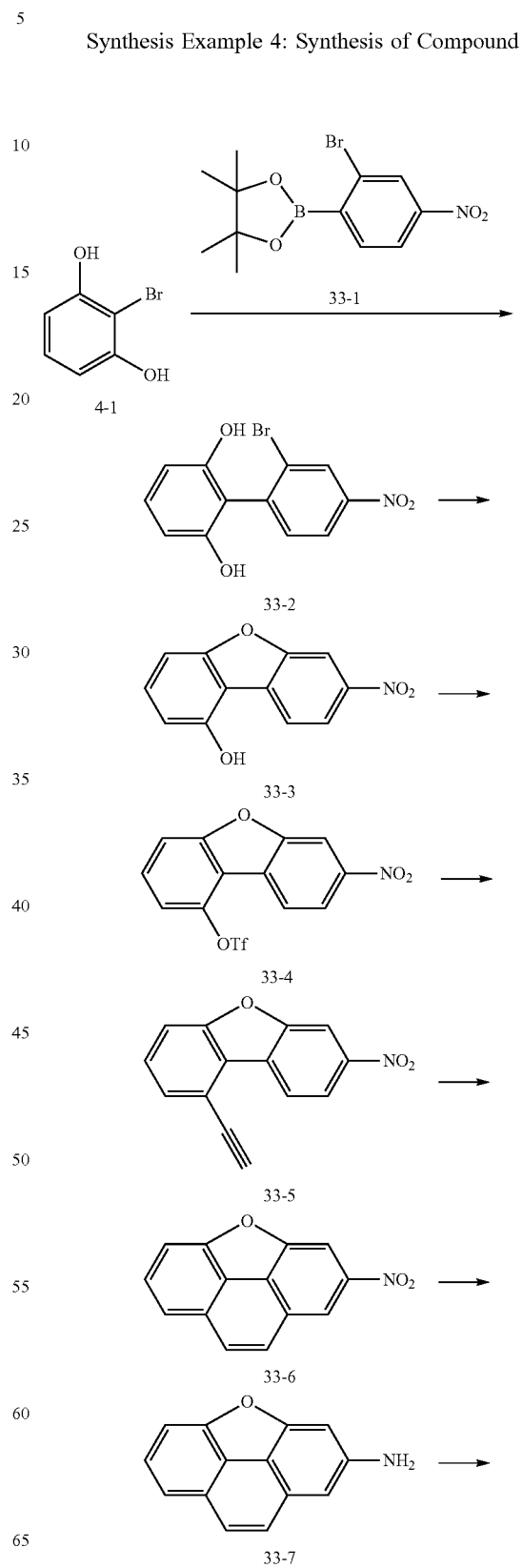

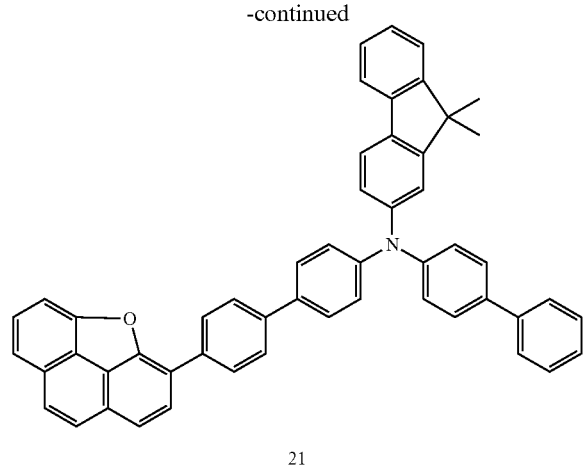

21

(1) Synthesis of Intermediate 21-1

3.8 g (yield: 78%) of Intermediate 21-1 was obtained in the same manner as in Synthesis of Intermediate 4-10, except that 4 g of Intermediate 4-9 and 5 g of (4'-bromo-[1,1'-biphenyl]-4-yl)boronic acid were used.

LC/MS cal'd: 422.03. found: 422.03.

(2) Synthesis of Compound 21

5.2 g (yield: 82%) of Compound 21 was obtained in the same manner as in Synthesis of Compound 4, except that 3.8 g of Intermediate 21-1 and 3.4 g of N-([1,1'-biphenyl]-4-yl)-9,9-dimethyl-9H-fluoren-2-amine were used LC/MS cal'd: 703.29. found: 703.31.

Synthesis Example 3: Synthesis of Compound 25

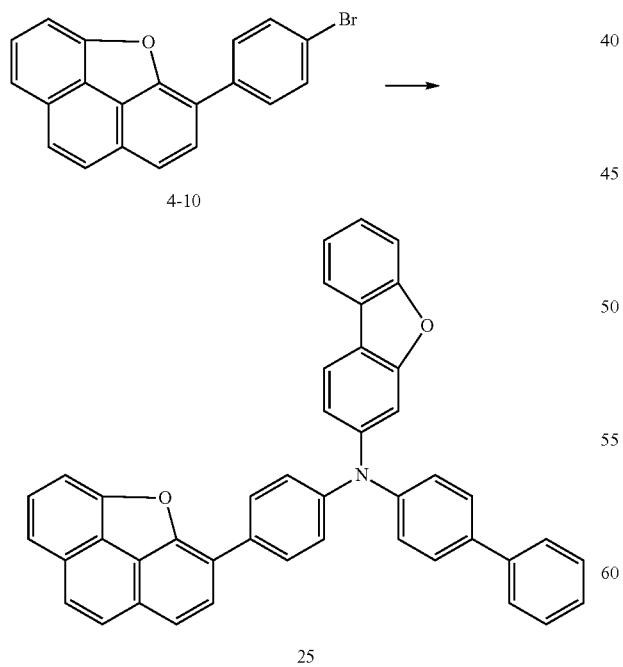

4.6 g (yield: 77%) of Compound 25 was obtained in the same manner as in Synthesis of Compound 4, except that 3.5

-continued

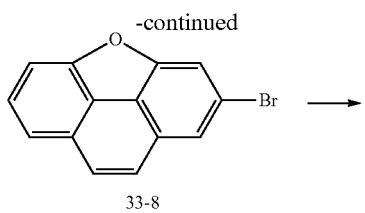

33-8

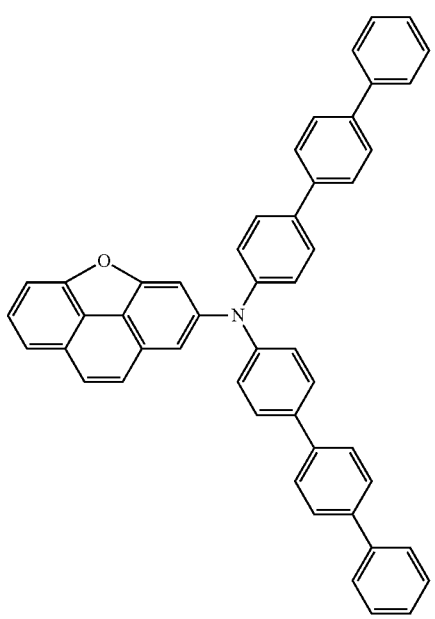

33

(1) Synthesis of Intermediate 33-1

28 g (yield: 94%) of Intermediate 33-1 was obtained in the same manner as in Synthesis of Intermediate 4-2, except that 30 g of 2-bromo-1-iodo-4-nitrobenzene was used.

LC/MS cal'd: 327.03. found: 327.06.

(2) Synthesis of Intermediate 33-2

21 g (yield: 76%) of Intermediate 33-2 was obtained in the same manner as in Synthesis of Intermediate 4-3, except that 16 g of Intermediate 4-1 and 28 g of Intermediate 33-1 were used.

LC/MS cal'd: 308.96. found: 308.98.

(3) Synthesis of Intermediate 33-3

16 g (yield: 99%) of Intermediate 33-3 was obtained in the same manner as in Synthesis of Intermediate 4-4, except that 21 g of Intermediate 33-2 was used.

LC/MS cal'd: 229.04. found: 229.06.

(4) Synthesis of Intermediate 33-4

25 g (yield: 98%) of Intermediate 33-4 was obtained in the same manner as in Synthesis of Intermediate 4-5, except that 16 g of Intermediate 33-2 was used.

LC/MS cal'd: 360.99. found: 360.99.

(5) Synthesis of Intermediate 33-5

16 g (yield: 98%) of Intermediate 33-5 was obtained in the same manner as in Synthesis of Intermediate 4-6, except that 25 g of Intermediate 33-4 was used LC/MS cal'd: 237.04. found: 237.07.

(6) Synthesis of Intermediate 33-6

15 g (94%) of Intermediate 33-6 was obtained in the same manner as in Synthesis of Intermediate 4-7, except that 16 g of Intermediate 33-5 was used.

LC/MS cal'd: 237.04. found: 237.06.

(7) Synthesis of Intermediate 33-7

15 g of Intermediate 33-6 was diluted with 150 ml of dichloromethane and 300 ml of ethanol, and then, 17 g of iron and 26 ml of conc. HCl were added thereto. The mixed solution was refluxed and stirred for 6 hours while maintaining the reaction temperature. After the reaction solution was cooled to ambient temperature, the reaction solution was filtered using Celite under a reduced pressure and evaporated under a reduced pressure. The residues were separated-purified by silica gel chromatography, so as to obtain 12.5 g (yield: 96%) of Intermediate 33-7.

LC/MS cal'd: 207.08. found: 207.09.

(8) Synthesis of Intermediate 33-8

12.5 g of Intermediate 33-7 was diluted with 300 ml of acetonitrile, and then, 10 ml of conc. HCl was slowly added dropwise thereto at a temperature of 0° C. The mixed solution was stirred at a temperature of 0° C. for 30 minutes, and 12.5 g of sodium nitrite was added thereto. After the reaction temperature was slowly raised to ambient temperature, the reaction solution was stirred for 1 hour, and 22 g of Cu(II)Br was additionally added thereto. The reaction solution was stirred again for 8 hours, and then, neutralized by using a saturated sodium bicarbonate solution. The neutralized reaction solution was extracted with ethyl acetate three times, and evaporated under a reduced pressure. The residues obtained therefrom were subjected to silica gel chromatography, so as to obtain 12.5 g (yield: 76%) of Intermediate 33-8.

LC/MS cal'd: 269.97. found: 269.97.

(9) Synthesis of Compound 33

5 g (yield: 76%) of Compound 33 was obtained in the same manner as in Synthesis of Compound 4, except that 2.7 g of Intermediate 33-8 and 4.8 g of di([1,1': 4',1"-terphenyl]-4-yl)amine were used.

LC/MS cal'd: 663.26. found: 663.26.

Synthesis Example 5: Synthesis of Compound 40

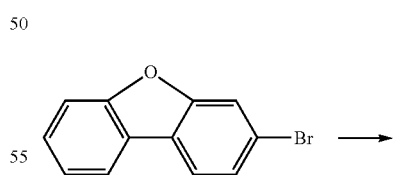

40-8

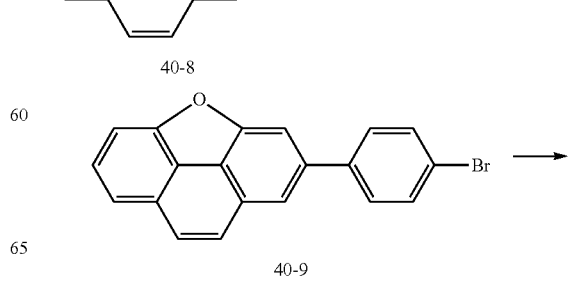

40-9

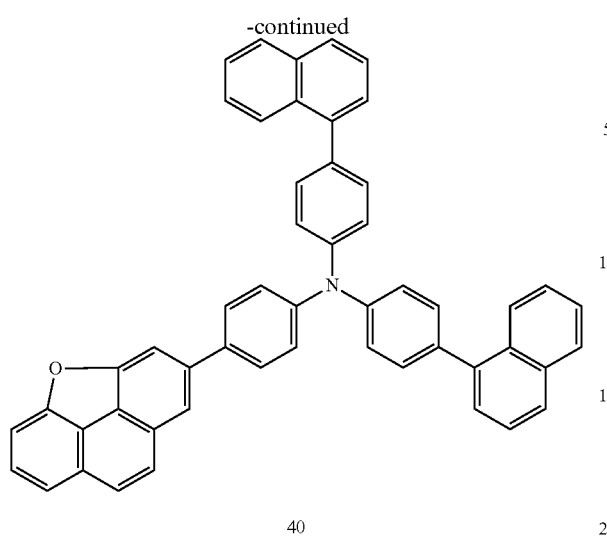

40

(1) Synthesis of Intermediate 40-9

4.8 g (yield: 92%) of Intermediate 40-9 was obtained in the same manner as in Synthesis of Intermediate 4-10, except that 4 g of Intermediate 40-8 was used.

LC/MS cal'd: 346.00. found: 346.02.

(2) Synthesis of Compound 40

6.9 g (yield: 73%) of Compound 40 was obtained in the same manner as in Synthesis of Compound 4, except that 4.8 g of Intermediate 40-9 and 5.8 g of bis(4-(naphthalen-1-yl)phenyl)amine were used.

LC/MS cal'd: 687.26. found: 687.29.

Synthesis Example 6: Synthesis of Compound 49

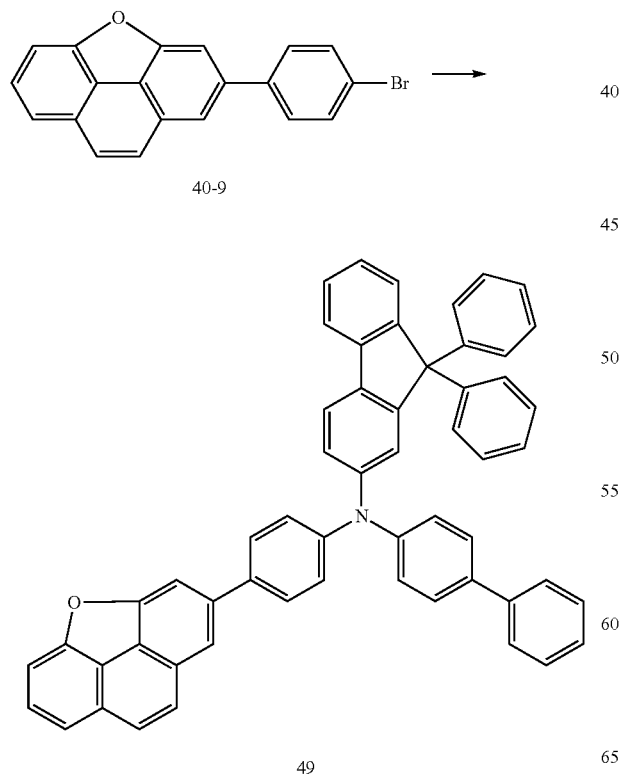

6 g (yield: 81%) of Compound 49 was obtained in the same manner as in Synthesis of Compound 4, except that 3.4 g of Intermediate 40-9 and 4.9 g of N-([1,1'-biphenyl]-4-yl)-9,9-diphenyl-9H-fluoren-2-amine were used.

LC/MS cal'd: 751.29. found: 751.29.

Synthesis Example 7: Synthesis of Compound 64

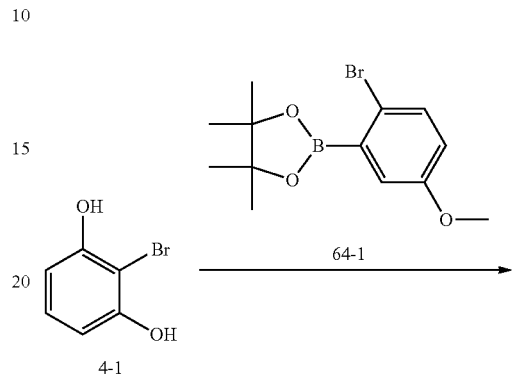

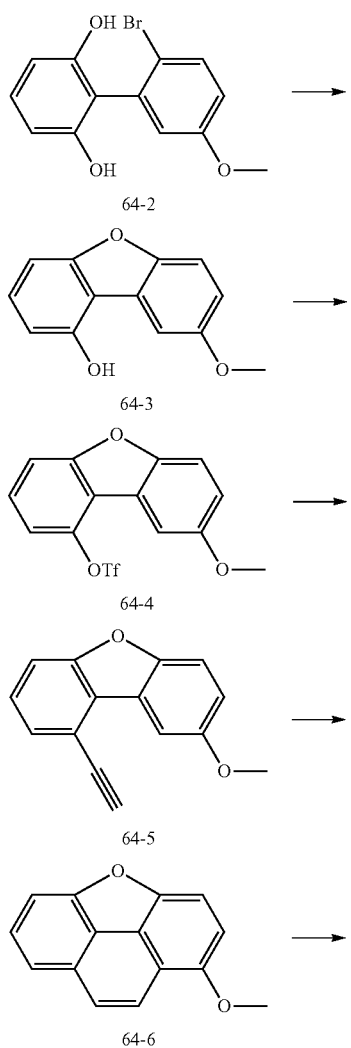

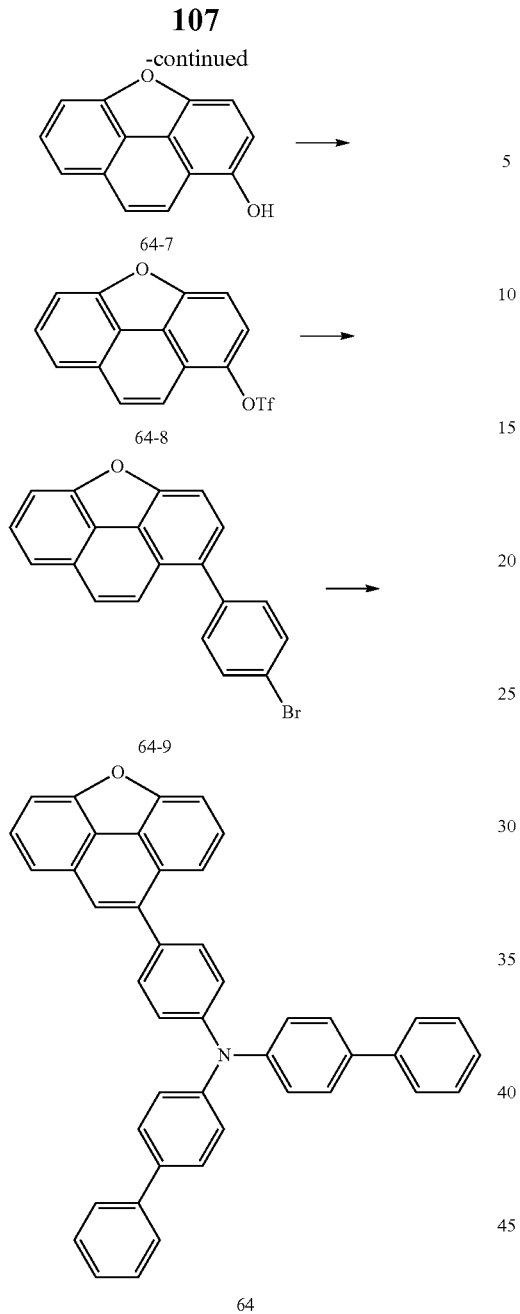

(4) Synthesis of Intermediate 64-4

21 g (yield: 88%) of Intermediate 64-4 was obtained in the same manner as in Synthesis of Intermediate 4-5, except that 15 g of Intermediate 64-3 was used.

LC/MS cal'd: 346.01. found: 346.04.

(5) Synthesis of Intermediate 64-5

18 g (yield: 81%) of Intermediate 64-5 was obtained in the same manner as in Synthesis of Intermediate 4-6, except that 21 g of Intermediate 64-4 was used.

LC/MS cal'd: 222.07. found: 222.07.

(6) Synthesis of Intermediate 64-6

15 g (yield: 86%) of Intermediate 64-6 was obtained in the same manner as in Synthesis of Intermediate 4-7, except that 18 g of Intermediate 64-5 was used.

LC/MS cal'd: 222.07. found: 222.09.

(7) Synthesis of Intermediate 64-7

11 g (yield: 78%) of Intermediate 64-7 was obtained in the same manner as in Synthesis of Intermediate 4-8, except that 15 g of Intermediate 64-6 was used.

LC/MS cal'd: 208.05. found: 208.07.

(8) Synthesis of Intermediate 64-8

17 g (yield: 93%) of Intermediate 64-8 was obtained in the same manner as in Synthesis of Intermediate 4-9, except that 11 g of Intermediate 64-7 was used.

LC/MS cal'd: 340.00. found: 340.00.

(9) Synthesis of Intermediate 64-9

13 g (yield: 78%) of Intermediate 64-9 was obtained in the same manner as in Synthesis of Intermediate 4-10, except that 17 g of Intermediate 64-8 was used.

LC/MS cal'd: 346.00. found: 346.00.

(10) Synthesis of Compound 64

4.5 g (yield: 77%) of Compound 64 was obtained in the same manner as in Synthesis of Compound 4, except that 3.4 g of Intermediate 64-9 was used.

LC/MS cal'd: 587.22. found: 587.72.

Synthesis Example 8: Synthesis of Compound 82

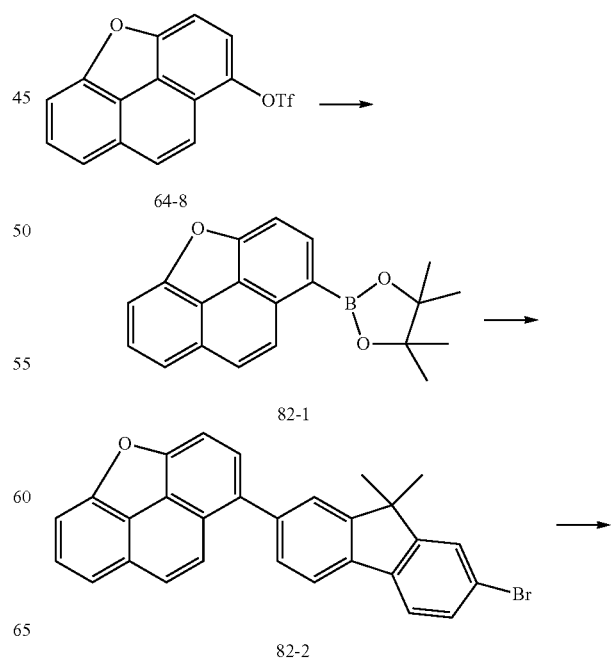

(1) Synthesis of Intermediate 64-1

28 g (yield: 90%) of Intermediate 64-1 was obtained in the same manner as in Synthesis of Intermediate 4-2, except that 31 g of 1-bromo-2-iodo-4-methoxybenzene was used.

LC/MS cal'd: 312.05. found: 312.09.

(2) Synthesis of Intermediate 64-2

23 g (yield: 87%) of Intermediate 64-2 was obtained in the same manner as in Synthesis of Intermediate 4-3, except that 28 g of Intermediate 64-1 was used.

LC/MS cal'd: 293.99. found: 293.99.

(3) Synthesis of Intermediate 64-3

15 g (yield: 89%) of Intermediate 64-3 was obtained in the same manner as in Synthesis of Intermediate 4-4, except that 23 g of Intermediate 64-2 was used.

LC/MS cal'd: 214.06. found: 214.08.

-continued

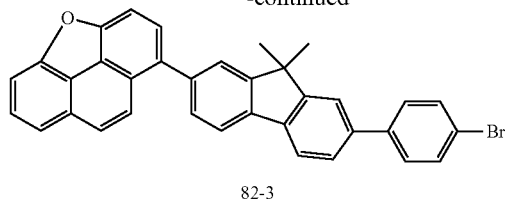

82-3

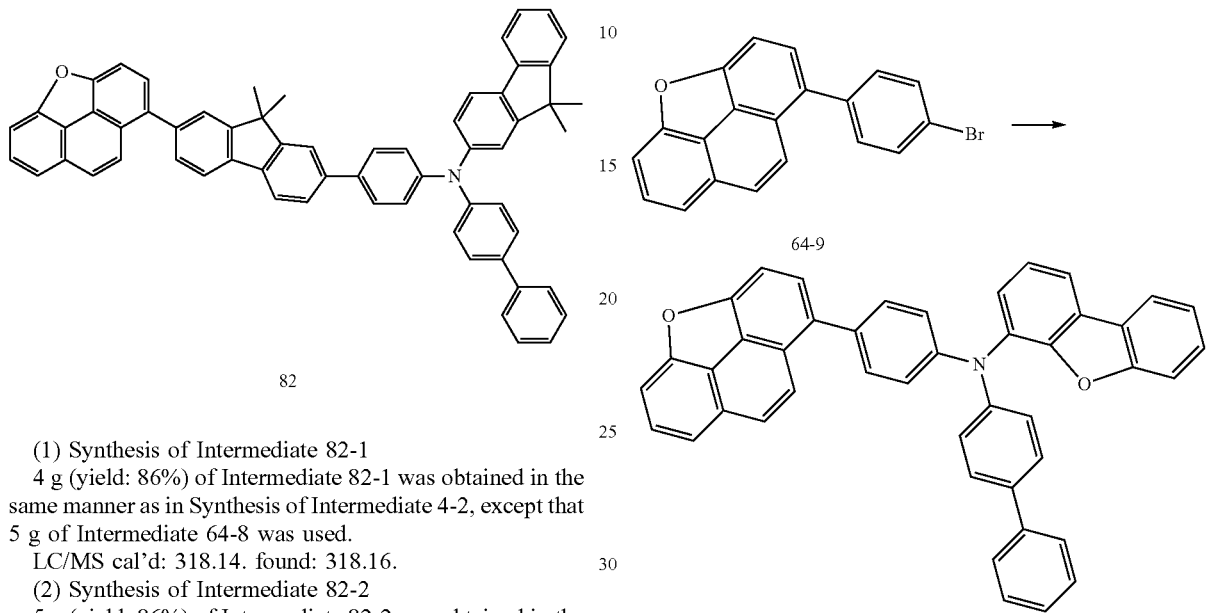

(1) Synthesis of Intermediate 82-1

4 g (yield: 86%) of Intermediate 82-1 was obtained in the same manner as in Synthesis of Intermediate 4-2, except that 5 g of Intermediate 64-8 was used.

LC/MS cal'd: 318.14. found: 318.16.

(2) Synthesis of Intermediate 82-2

5 g (yield: 86%) of Intermediate 82-2 was obtained in the same manner as in Synthesis of Intermediate 4-3, except that 4 g of Intermediate 82-1 and 6.5 g of 2,7-dibromo-9,9-dimethyl-9H-fluorene were used.

LC/MS cal'd: 462.06. found: 462.07.

(3) Synthesis of Intermediate 82-3

4.3 g (yield: 73%) of Intermediate 82-3 was obtained in the same manner as in Synthesis of Intermediate 4-10, except that 5 g of Intermediate 82-2 was used.

LC/MS cal'd: 538.09. found: 538.12.

(4) Synthesis of Compound 82

5 g (yield: 77%) of Compound 82 was obtained in the same manner as in Synthesis of Compound 21, except that 4.3 g of Intermediate 82-2 was used.

LC/MS cal'd: 819.35. found: 813.36.

Synthesis Example 9: Synthesis of Compound 86

4.4 g (yield: 84%) of Compound 86 was obtained in the same manner as in Synthesis of Compound 4, except that 3 g of Intermediate 64-9 and 3 g of N-([1,1'-biphenyl]-4-yl)dibenzo[b,d]furan-4-amine were used.

LC/MS cal'd: 601.20. found: 601.23.

Spectrum values of the compound synthesized above are shown in Table 1 below.

TABLE 1

| Compound | $^1$H NMR (CDCl$_3$, 400 MHz) | LC/MS found | calc. |
|---|---|---|---|
| 4 | 8.03 (d, 1H), 7.82 (d, 2H), 7.80 (m, 1H), 7.75 (m, 1H), 7.64 (m, 1H), 7.57-7.51 (m, 6H), 7.48-7.43 (m, 9H), 7.37 (d, 2H), 6.83-6.78 (m, 6H) | 587.22 | 587.24 |
| 21 | 8.00 (d, 1H), 7.81-7.74 (m, 9H), 7.66 (t, 1H), 7.57-7.54 (m, 2H), 7.48-7.30 (m, 10H), 7.11 (m, 2H), 6.70 (dd, 1H), 6.56-6.48 (m, 4H), 6.41 (dd, 1H), 1.61 (s, 6H) | 703.29 | 703.31 |
| 25 | 8.04 (d, 1H), 7.82-7.75 (m, 6H), 7.68 (t, 1H), 7.57-7.34 (m, 12H), 7.23 (td, 1H,), 6.98-6.87 (m, 4H), 6.72 (dd, 2H) | 601.20 | 601.21 |
| 33 | 7.81-7.62 (m, 11H), 7.58-7.44 (m, 14H), 7.37 (m, 2H), 7.08 (dd, 1H), 6.75-6.71 (m, 5H) | 663.26 | 663.26 |
| 40 | 8.13 (d, 1H), 7.84-7.78 (m, 4H), 7.73 (m, 1H), 7.70 (t, 1H), 7.64-7.41 (m, 15H), 7.27 (td, 2H), 7.04 (td, 2H), 6.94-6.91 (m, 4H), 6.61-6.58 (m, 2H) | 687.26 | 687.29 |
| 49 | 8.12 (d, 1H), 7.88 (dd, 1H), 7.79 (t, 2H), 7.61-7.56 (m, 3H), 7.47-7.33 (m, 11H), 7.28-7.12 (m, 11H), 6.81 (dd, 1H), 6.72 (dd, 1H), 6.53-6.50 (m, 4H), 6.52 (d, 1H) | 751.29 | 751.29 |

TABLE 1-continued

| Compound | $^1$H NMR (CDCl$_3$, 400 MHz) | LC/MS found | calc. |
|---|---|---|---|
| 64 | 7.89 (d, 1H), 7.74 (m, 1H), 7.72 (d, 1H), 7.62-7.54 (m, 7H), 7.53-7.41 (m, 11H), 7.42-7.38 (m, 2H), 6.94-6.91 (m, 2H), 6.86-6.81 (m, 4H) | 587.22 | 587.22 |
| 82 | 7.84-7.80 (m, 2H), 7.78-7.69 (m, 6H), 7.64-7.54 (m, 5H), 7.50 (d, 1H), 7.48-7.31 (m, 17H), 7.14-7.08 (m, 2H), 6.70 (dd, 1H), 6.52-6.45 (m, 4H), 6.51 (d, 1H), 1.61 (s, 6H), 1.58 (s, 6H) | 819.35 | 819.36 |
| 86 | 7.88-7.84 (m, 2H), 7.75 (m, 1H), 7.70 (d, 1H), 7.68-7.65 (m, 2H), 7.61-7.55 (m, 5H), 7.51-7.32 (m, 10H), 7.00-6.92 (m, 2H0, 6.56-6.52 (m, 4H) | 601.20 | 601.23 |

EXAMPLES

Example 1

A 15 Ω/cm$^2$ (1,200 Å) ITO glass substrate (manufactured by Corning) was cut into a size of 50 mm×50 mm×0.7 mm and ultrasonically washed out with isopropyl alcohol and pure water, each for 5 minutes. The ITO glass substrate was irradiated by UV for 30 minutes, cleaned by exposing to ozone, and then, transported to a vacuum evaporator.

2-TNATA was vacuum deposited on the ITO anode to form an HIL having a thickness of 600 Å. Compound 4, as a hole transporting compound, was vacuum deposited on the HIL to form an HTL having a thickness of 300 Å. Then, 9,10-di-naphthalene-2-yl-anthracene (hereinafter, referred to as DNA), a blue fluorescent host, and 4,4'-bis[2-(4-(N, N-diphenylamino)phenyl)vinyl]biphenyl (hereinafter, referred to as DPAVBi), a blue fluorescent dopant, were co-deposited at a weight ratio of 98:2 on the HTL to form an emission layer having a thickness of 300 Å.

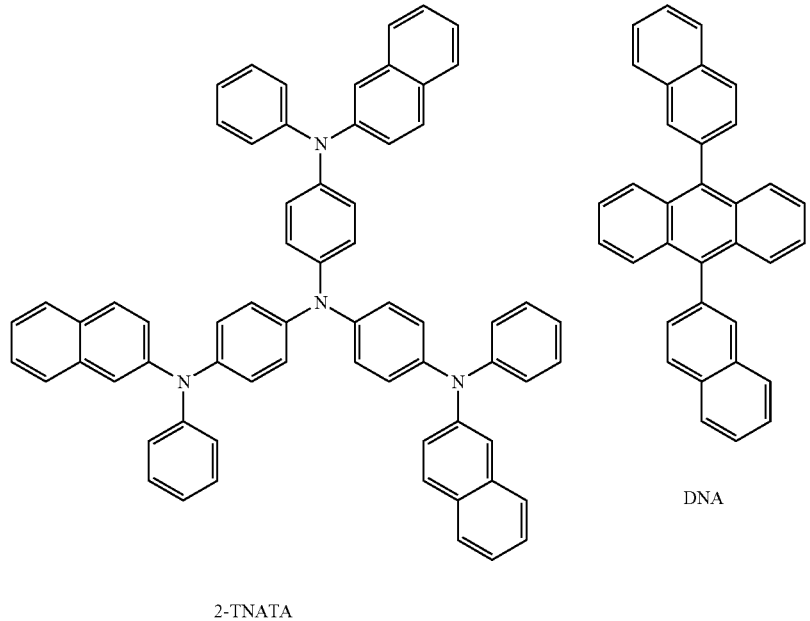

2-TNATA

DNA

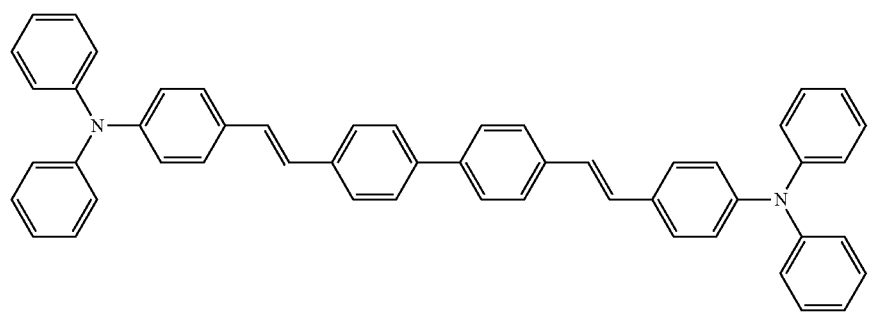

DPAVBi

Then, Alq₃ was deposited on the emission layer to form an ETL having a thickness of 300 Å, and LiF, a halogenated alkali metal, was deposited on the ETL to form an EIL having a thickness of 10 Å. Al was deposited on the EIL to form a cathode (i.e., a LiF/Al electrode) having a thickness of 3,000 Å, thereby manufacturing an organic light-emitting device.

Example 2

An organic light-emitting device was manufactured in the same manner as in Example 1, except that in forming the HTL, Compound 21 was used instead of Compound 4.

Example 3

An organic light-emitting device was manufactured in the same manner as in Example 1, except that in forming the HTL, Compound 25 was used instead of Compound 4.

Example 4

An organic light-emitting device was manufactured in the same manner as in Example 1, except that in forming the HTL, Compound 33 was used instead of Compound 4.

Example 5

An organic light-emitting device was manufactured in the same manner as in Example 1, except that in forming the HTL, Compound 40 was used instead of Compound 4.

Example 6

An organic light-emitting device was manufactured in the same manner as in Example 1, except that in forming the HTL, Compound 49 was used instead of Compound 4.

Example 7

An organic light-emitting device was manufactured in the same manner as in Example 1, except that in forming the HTL, Compound 64 was used instead of Compound 4.

Example 8

An organic light-emitting device was manufactured in the same manner as in Example 1, except that in forming the HTL, Compound 82 was used instead of Compound 4.

Example 9

An organic light-emitting device was manufactured in the same manner as in Example 1, except that in forming the HTL, Compound 87 was used instead of Compound 4.

Comparative Example 1

An organic light-emitting device was manufactured in the same manner as in Example 1, except that in forming the HTL, 4,4'-bis[N-(1-naphthyl)-N-phenylan amino group]biphenyl (hereinafter, referred to as NPB) was used instead of Compound 4.

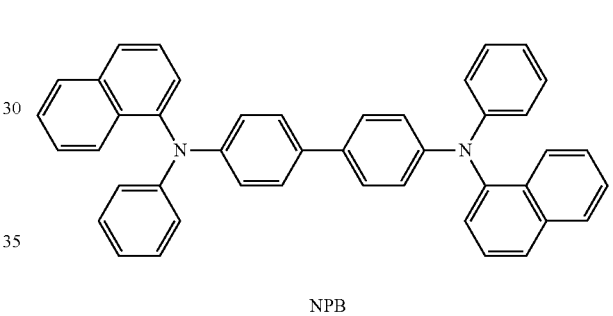

NPB

The characteristics of the organic light-emitting devices prepared in Examples 1 to 9 and Comparative Example 1 are shown in Table 2 below.

TABLE 2

| | Hole transporting material | Driving voltage (V) | Current density (mA/cm2) | Brightness (cd/m²) | Efficiency (cd/A) | Emitting color | Half-lifespan (hr @100 mA/cm²) |
|---|---|---|---|---|---|---|---|
| Example 1 | Compound 4 | 5.72 | 50 | 2,720 | 5.44 | blue | 278 |
| Example 2 | Compound 21 | 5.51 | 50 | 2,860 | 5.72 | blue | 256 |
| Example 3 | Compound 25 | 5.84 | 50 | 2,965 | 5.93 | blue | 286 |
| Example 4 | Compound 33 | 5.46 | 50 | 2,760 | 5.52 | blue | 295 |
| Example 5 | Compound 40 | 5.58 | 50 | 2,905 | 5.81 | blue | 314 |
| Example 6 | Compound 49 | 6.12 | 50 | 2,980 | 5.96 | blue | 306 |
| Example 7 | Compound 64 | 5.67 | 50 | 3,015 | 6.03 | blue | 323 |
| Example 8 | Compound 82 | 5.50 | 50 | 2,945 | 5.89 | blue | 255 |
| Example 9 | Compound 87 | 5.66 | 50 | 2,895 | 5.79 | blue | 296 |
| Comparative Example 1 | NPB | 7.15 | 50 | 2,115 | 4.23 | blue | 153 |

Referring to Table 2, it may be seen that when the compound of Formula 1 was used for forming the HTL, the driving voltage of the light-emitting device was significantly improved. In addition, the efficiency and lifespan characteristics of the light-emitting device including the compound of Formula 1 were significantly improved. For example, excellent lifespan characteristics of the light-emitting device including the compound of Formula significantly increased the lifespan of the light-emitting device.

As described above, an organic light-emitting device including a compound according to the one or more of the above embodiments may have high efficiency, low driving voltage, high brightness, and long lifespan characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic light-emitting device, comprising:
a first electrode;
a second electrode facing the first electrode; and
an organic layer between the first electrode and the second electrode, the organic layer including an emission layer,
wherein:
the first electrode is an anode, the second electrode is a cathode, and the organic layer includes: a hole transport region between the first electrode and the emission layer, the hole transport region including a hole transport layer and one or more of a hole injection layer or an electron blocking layer, and an electron transport region between the emission layer and the second electrode, the electron transport region including one or more of a hole blocking layer, an electron transport layer, or an electron injection layer, and
the hole transport layer includes a compound represented by one of Formula 2, Formula 3, or Formula 4:

<Formula 2>

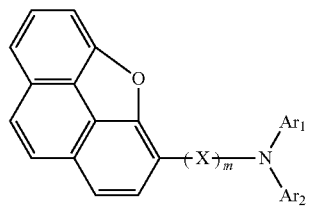

<Formula 3>

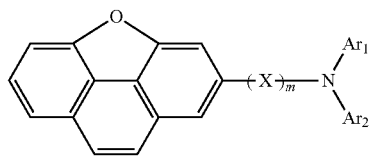

<Formula 4>

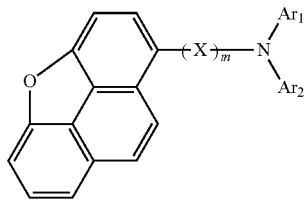

wherein, in Formula 2, Formula 3, and Formula 4,
$Ar_1$ and $Ar_2$ are each independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group;
X is a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group,
m is an integer 0 to 4,
at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_2$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group is:
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{11}$), or —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), or —B($Q_{26}$)($Q_{27}$); or —N($Q_{31}$)($Q_{32}$), wherein $Q_{11}$ to $Q_{17}$, $Q_{21}$ to $Q_{27}$, and $Q_{31}$ to $Q_{32}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group, and X is identical to or different from each other when m is 2, 3, or 4.

2. The organic light-emitting device as claimed in claim 1, wherein X is a substituted or unsubstituted $C_6$-$C_{60}$ arylene group, a substituted or unsubstituted $C_1$-$C_{60}$ heteroarylene group, or a substituted or unsubstituted divalent non-aromatic condensed polycyclic group.

3. The organic light-emitting device as claimed in claim 1, wherein X a group represented by one of the following Formulae 2a to 2c:

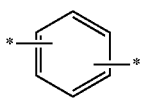

2a

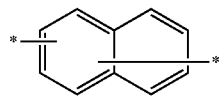

2b

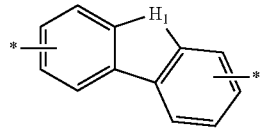

2c wherein, in Formulae 2a to 2c,
$H_1$ is $CR_1R_2$, O, or S,
$R_1$ and $R_2$ are each independently a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, or a substituted or unsubstituted monovalent non-aromatic condensed heteropolycyclic group, and
* is a binding site to a neighboring atom.

4. The organic light-emitting device as claimed in claim 1, wherein $Ar_1$ and $Ar_2$ are each independently a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

5. The organic light-emitting device as claimed in claim 1, wherein $Ar_1$ and $Ar_2$ are each independently a group represented by one of the following Formulae 3a to 3d:

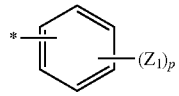

3a

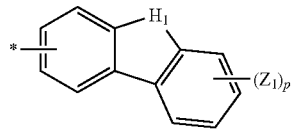

3b

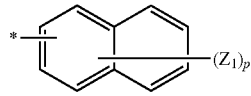

3c

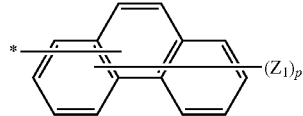

3d wherein, in Formulae 3a to 3d,
$H_1$ is $CR_1R_2$, O, or S,
$R_1$, $R_2$, and $Z_1$ are each independently a hydrogen, a deuterium, an amine group substituted with a $C_6$-$C_{20}$ aryl group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, or a substituted or unsubstituted monovalent non-aromatic condensed heteropolycyclic group, p is an integer of 1 to 9, and
* is a binding site to a neighboring atom.

6. The organic light-emitting device as claimed in claim 5, wherein $R_1$, $R_2$, and $Z_1$ are each independently a hydrogen, a deuterium, or a group represented by one of the following Formulae 4a to 4e:

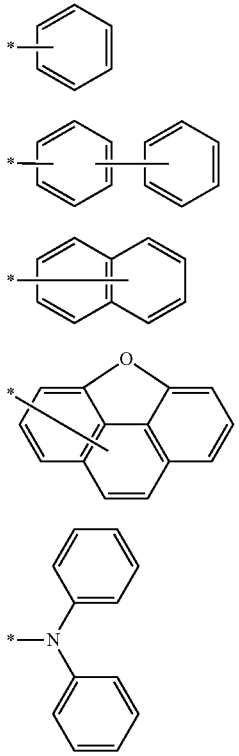

wherein, in Formulae 4a to 4e, * is a binding site to a neighboring atom.

7. The organic light-emitting device as claimed in claim 1, wherein the compound is represented by Formula 2.

8. The organic light-emitting device as claimed in claim 1, wherein the compound is represented by Formula 3.

9. The organic light-emitting device as claimed in claim 1, wherein the compound is represented by Formula 4.

10. The organic light-emitting device as claimed in claim 1, wherein the compound is one of the following Compounds 1 to 90:

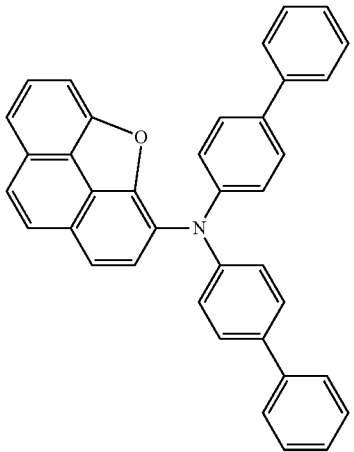

-continued

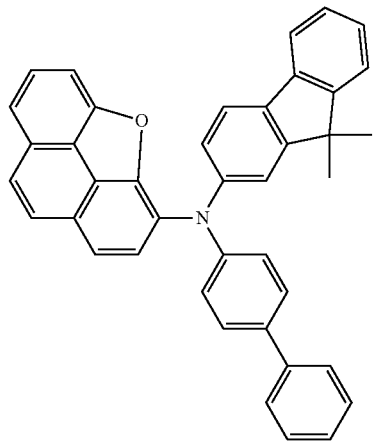

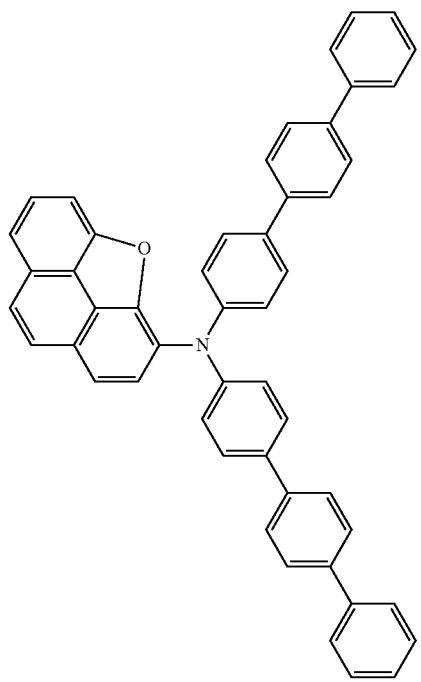

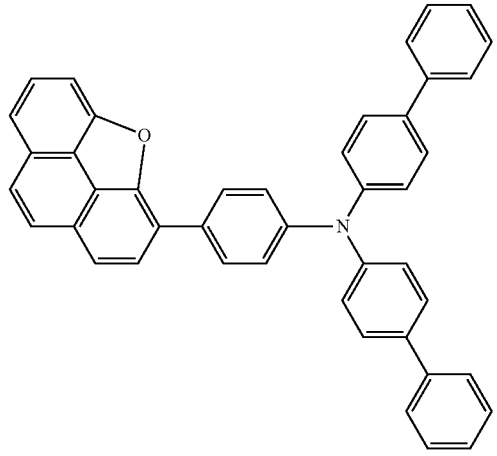

5
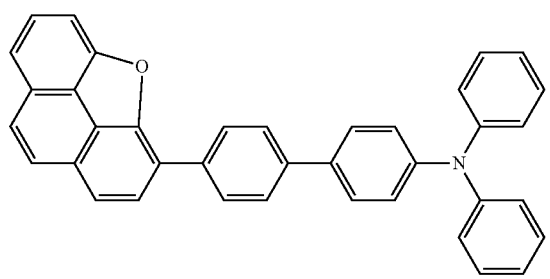
6
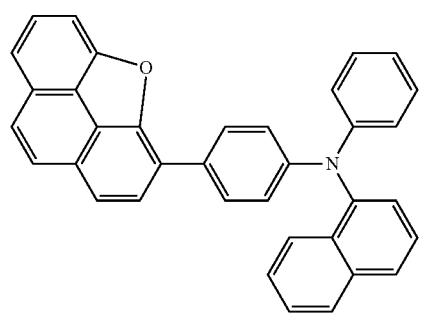
7
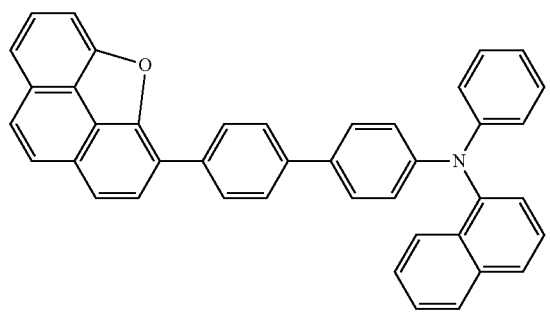
8
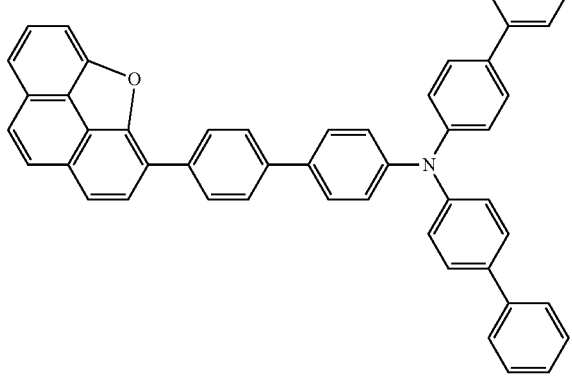
9
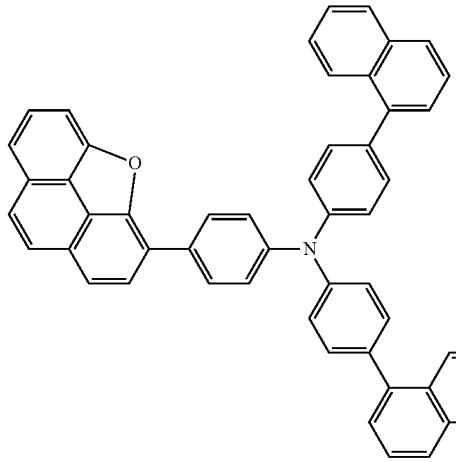
10
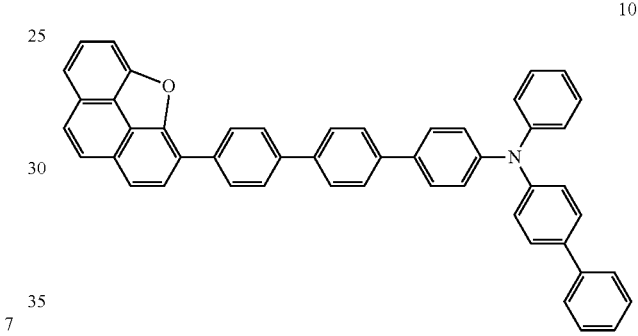
11
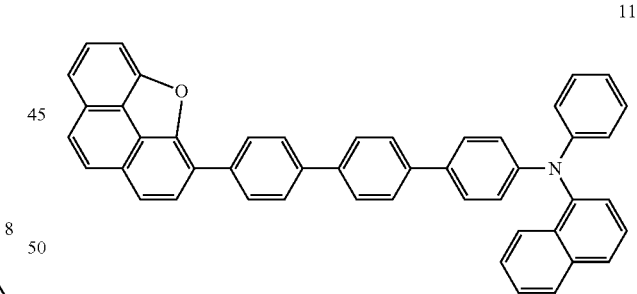
12
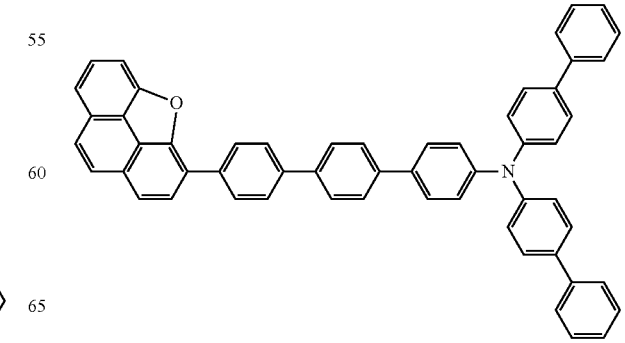

123
-continued
13
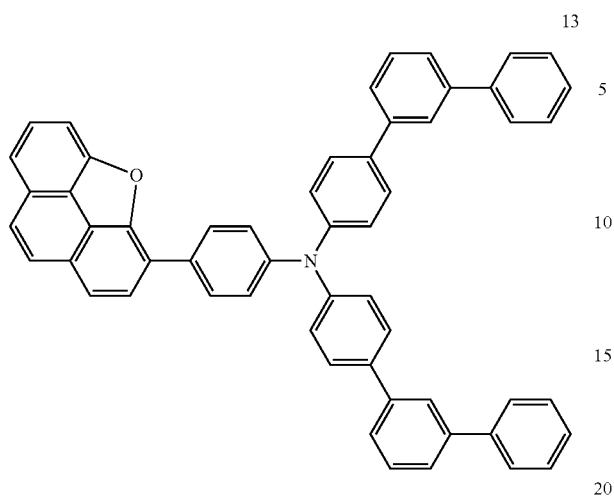
14
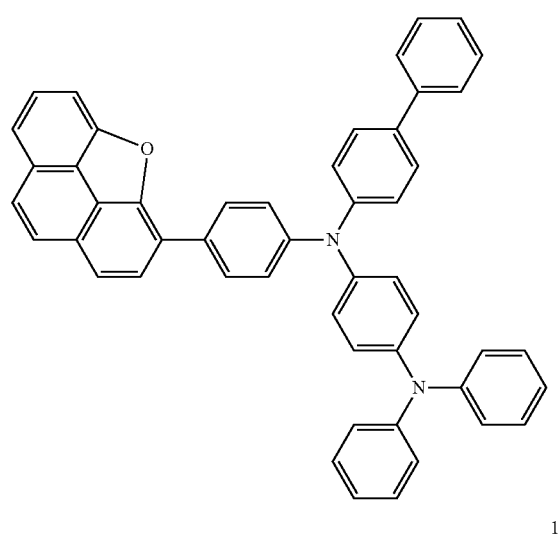
15
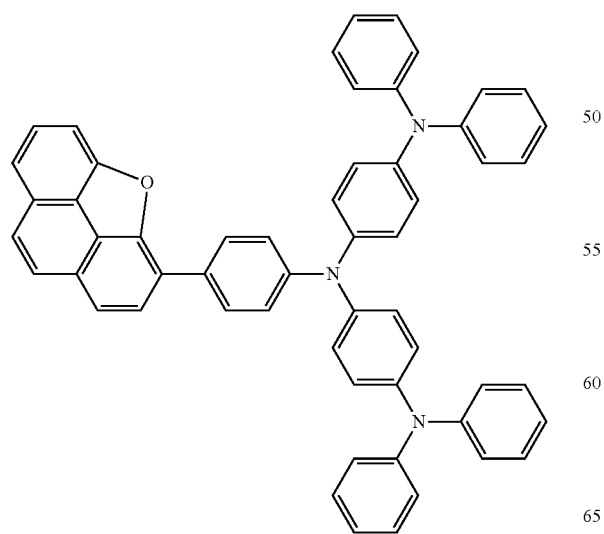
124
-continued
16
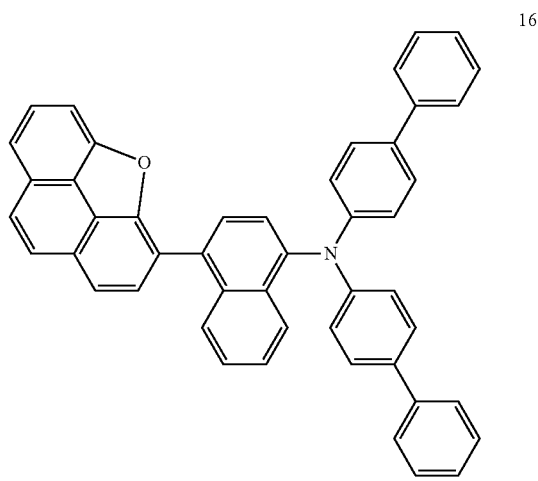
17
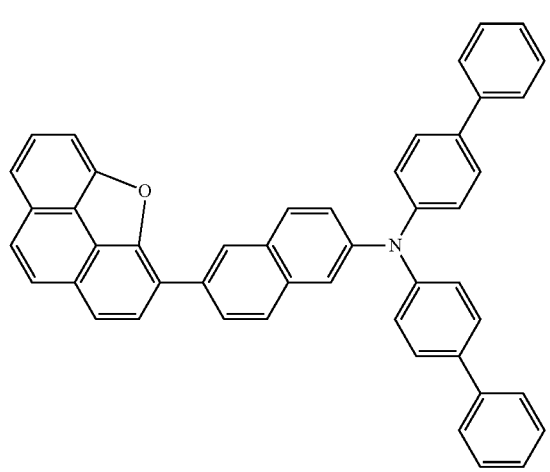
18
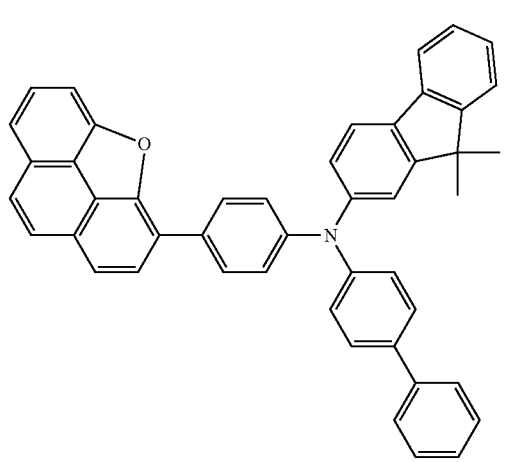

125
-continued
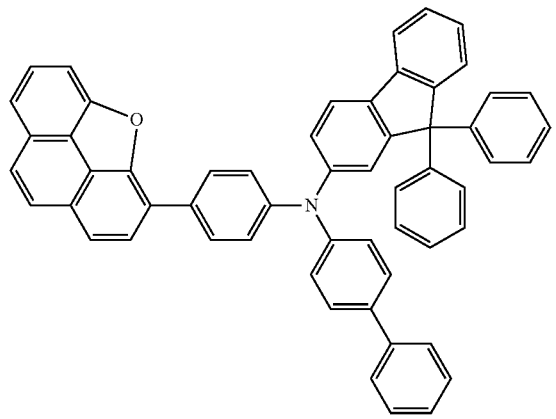
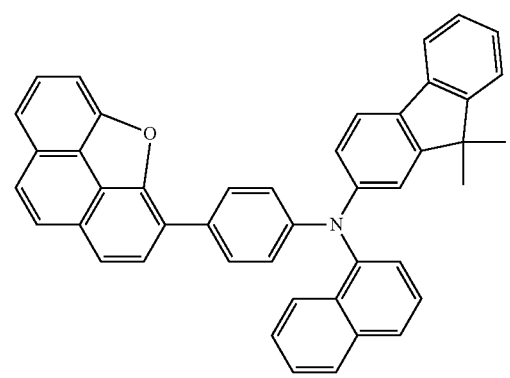
126
-continued
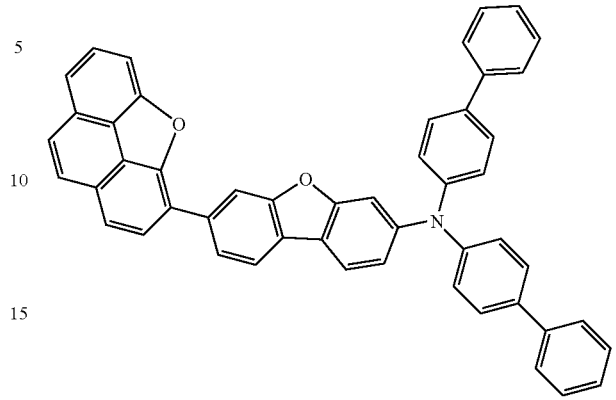
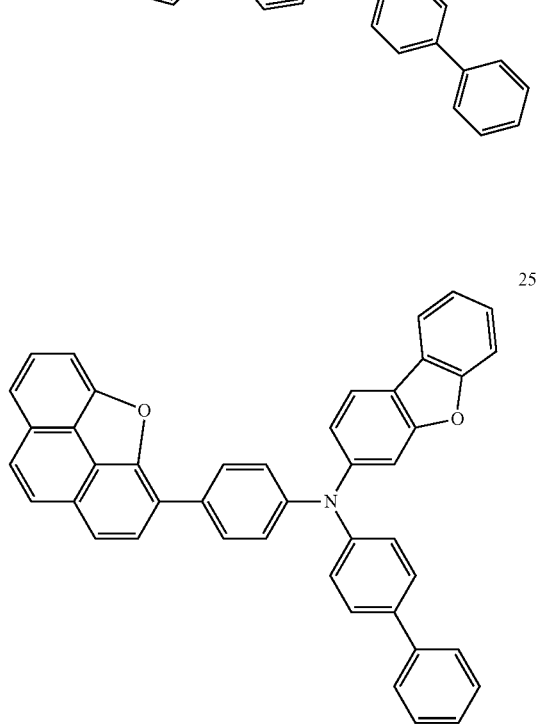

127
-continued
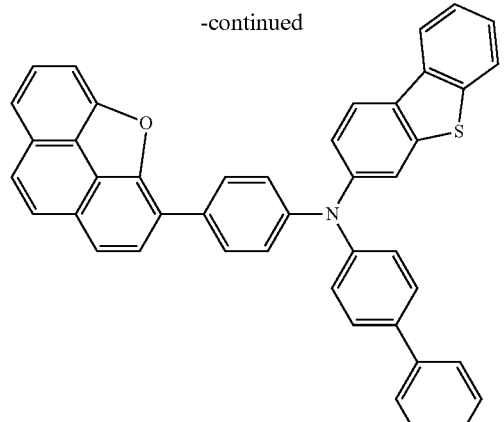
26
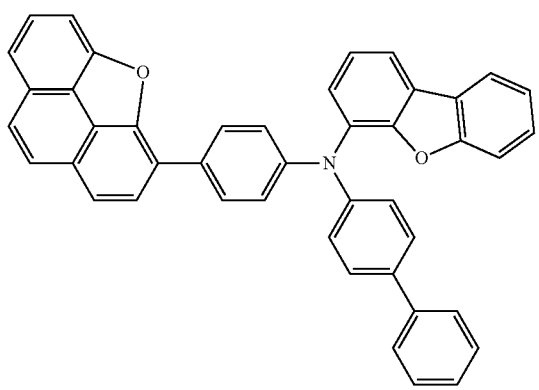
27
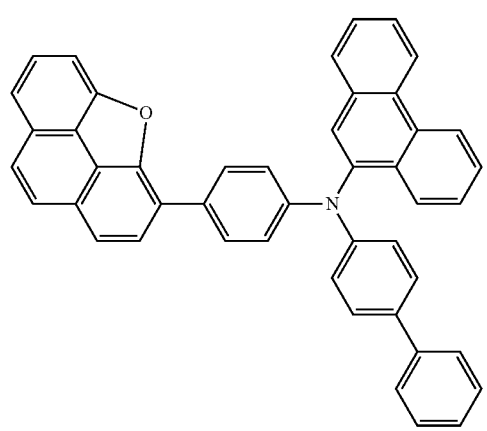
28
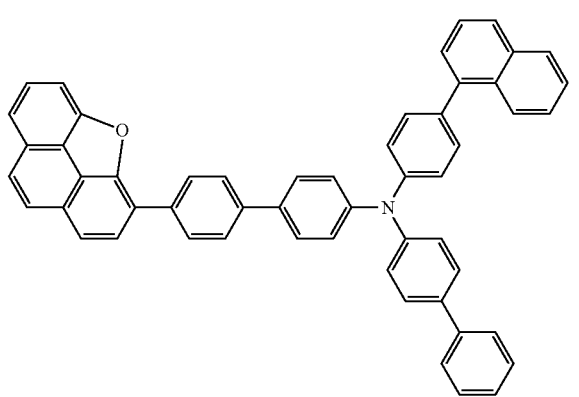
29
128
-continued
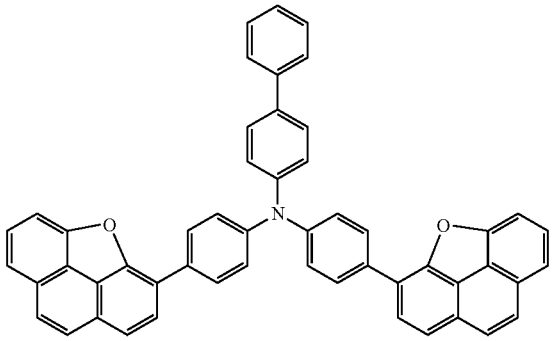
30
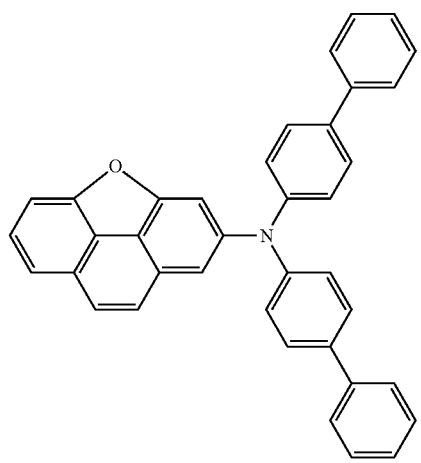
31
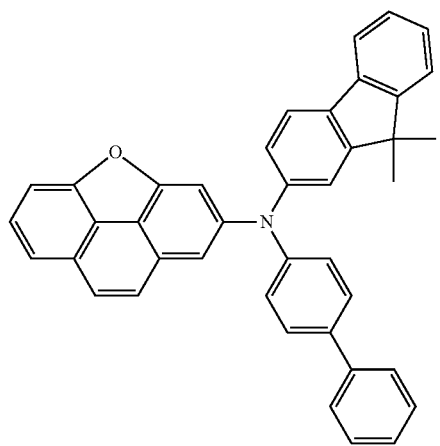
32

33
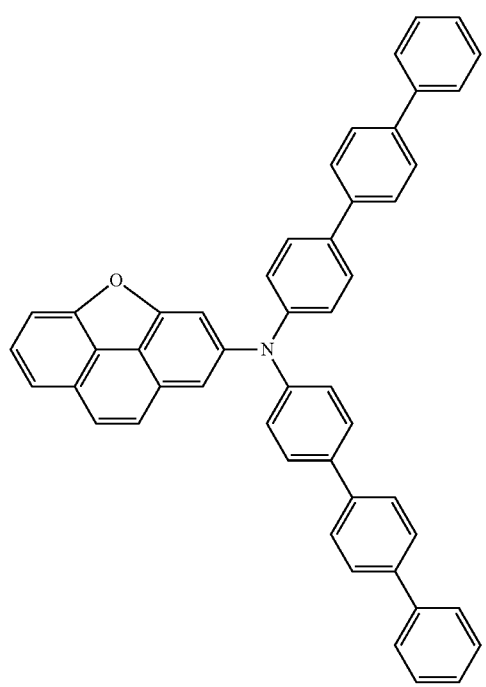
34
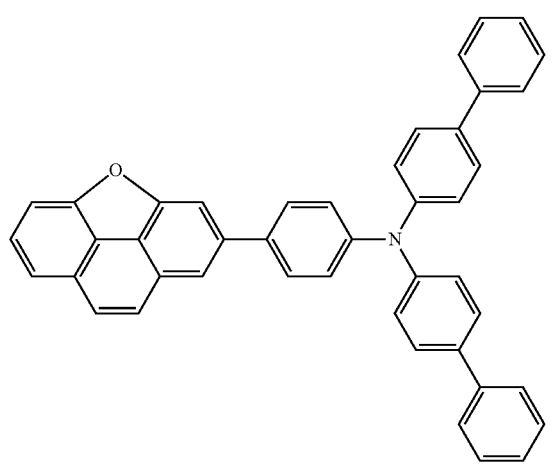
35
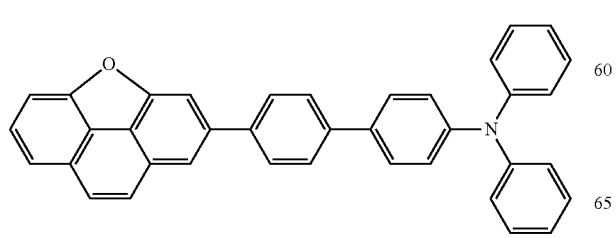
36
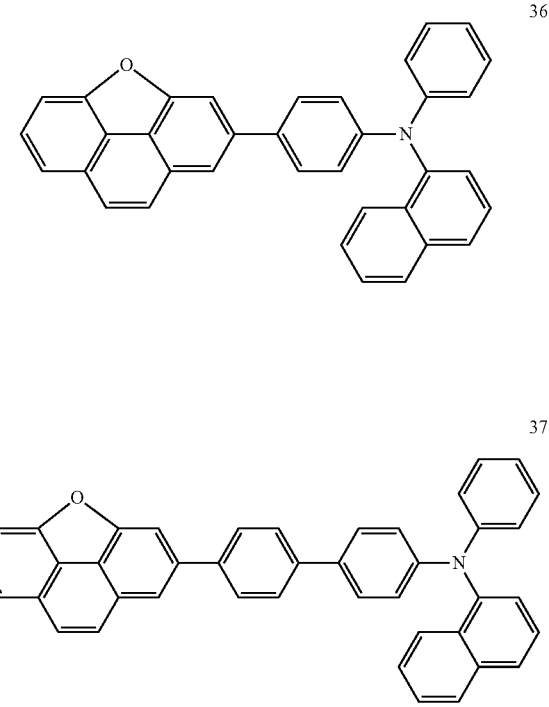
37
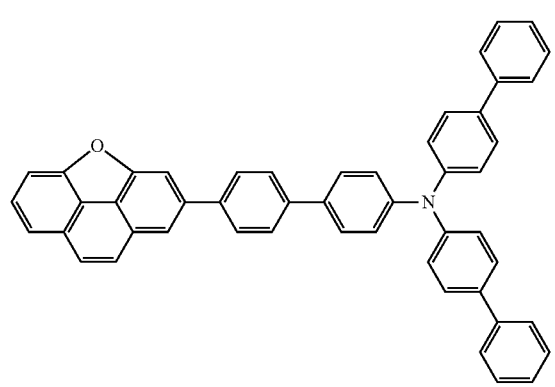
38
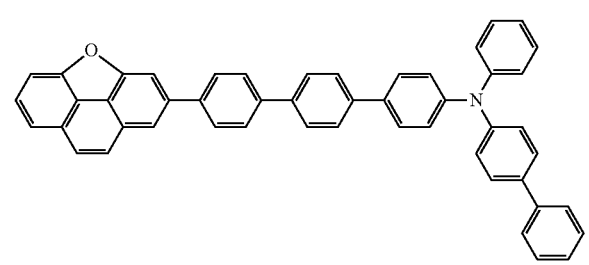
39

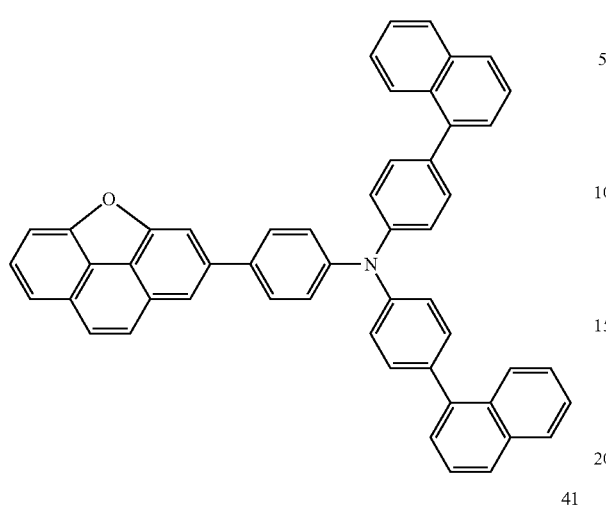
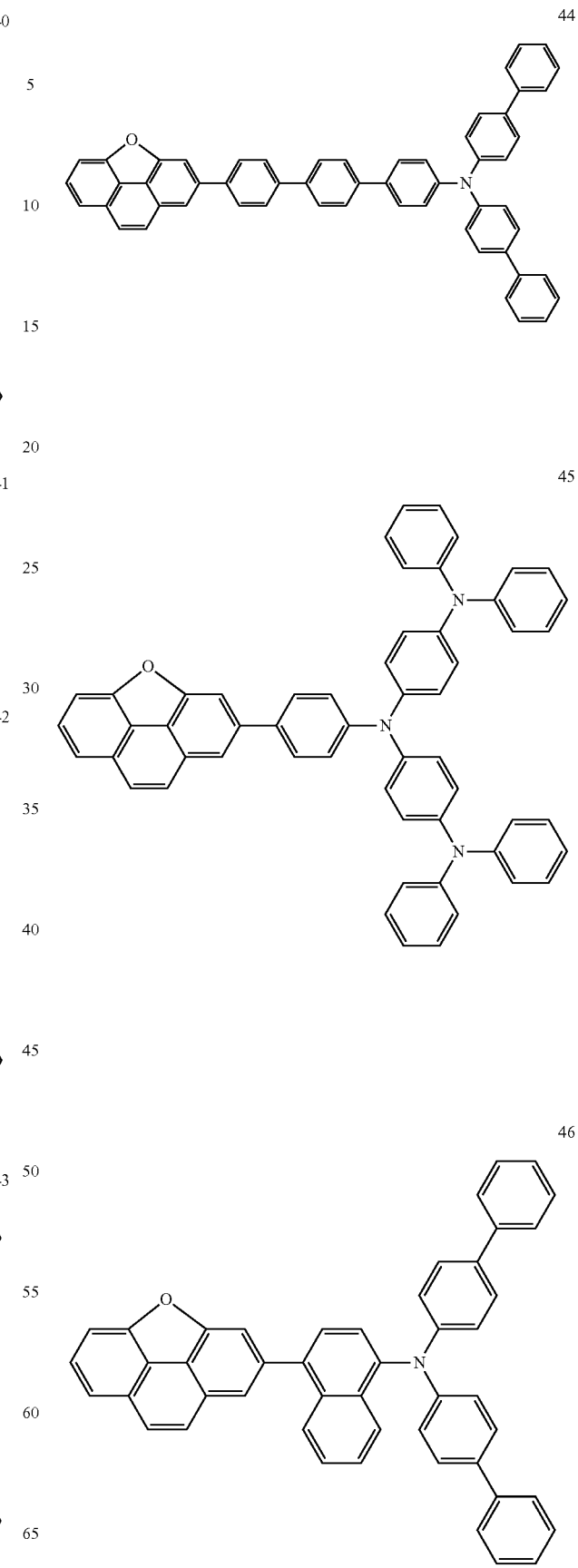

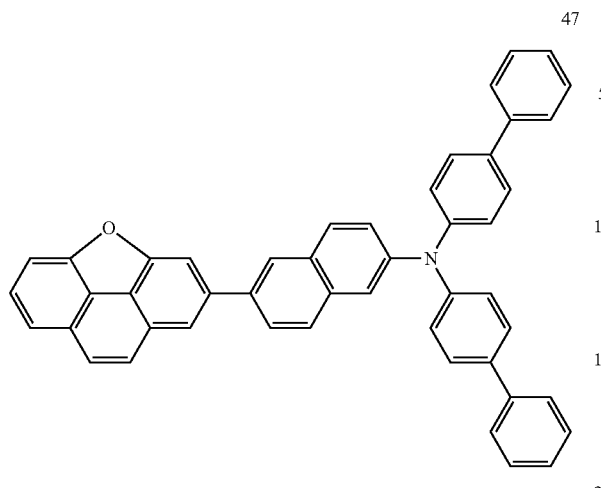
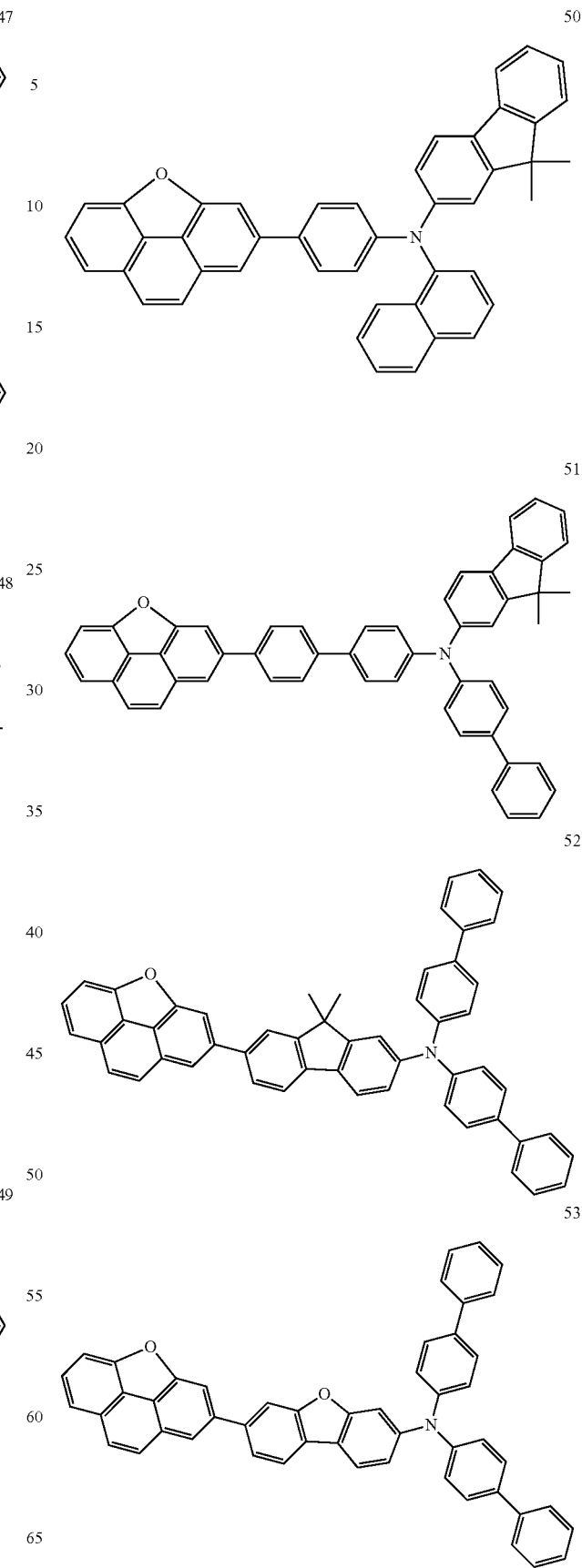

54
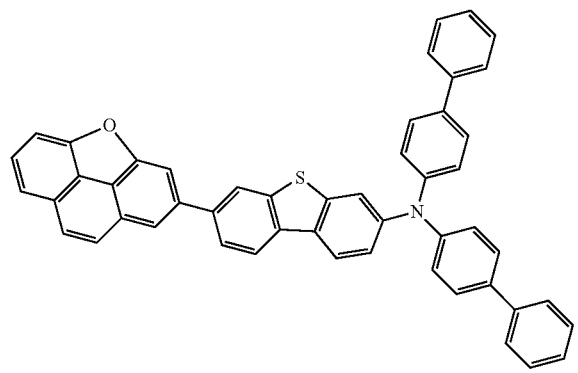
55
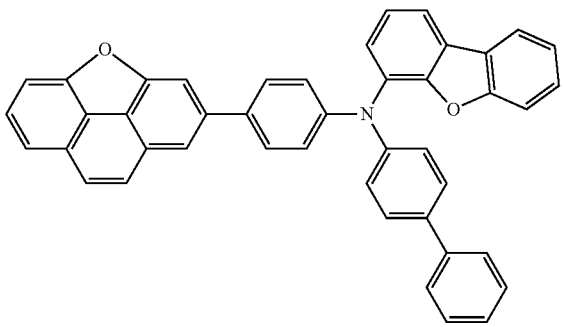
56
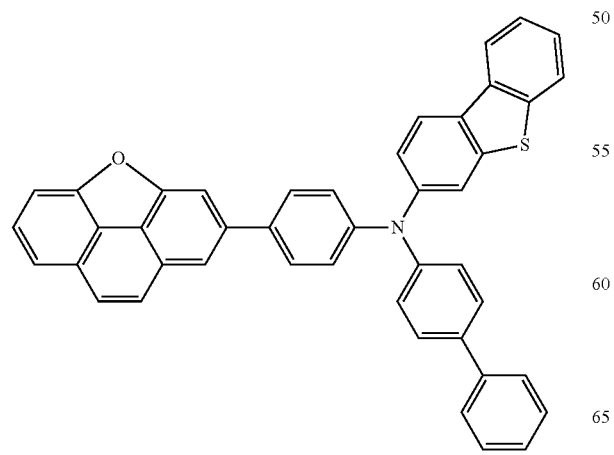
57
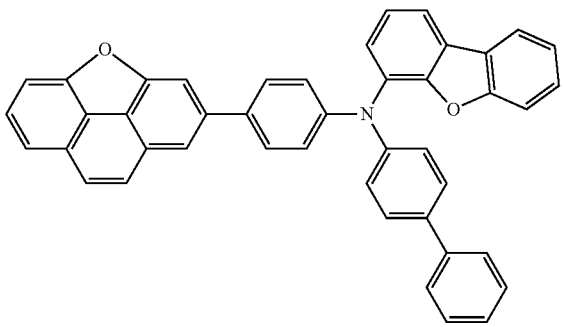
58
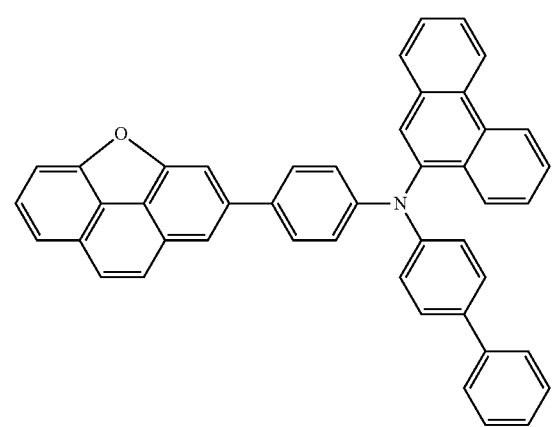
59
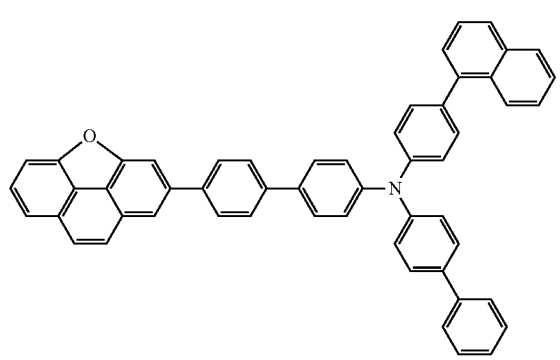
60
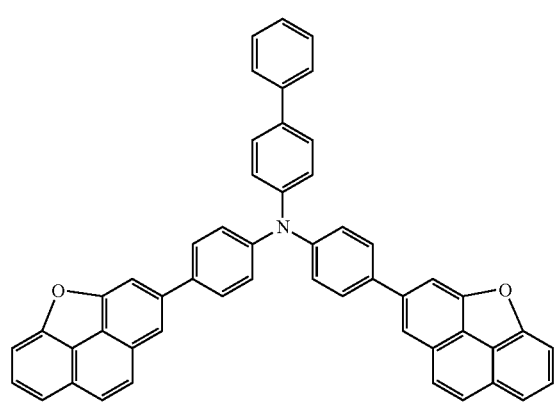

61
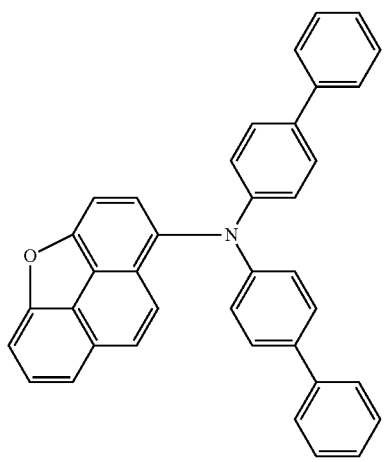
62
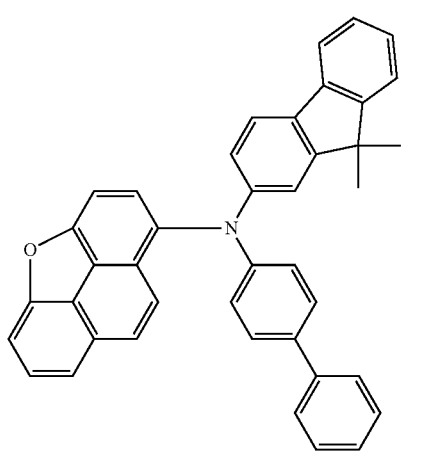
63
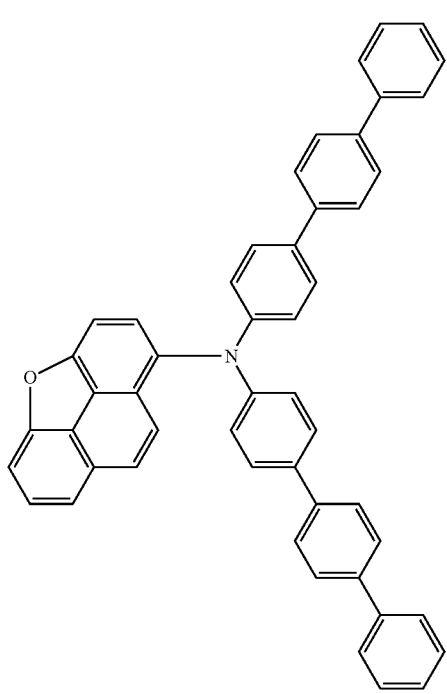
64
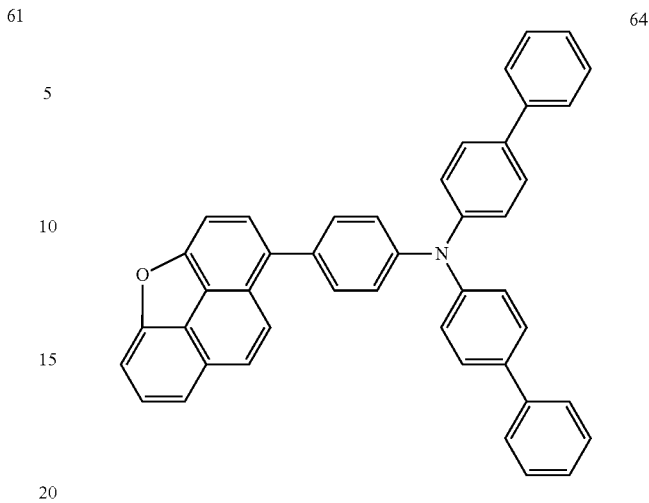
65
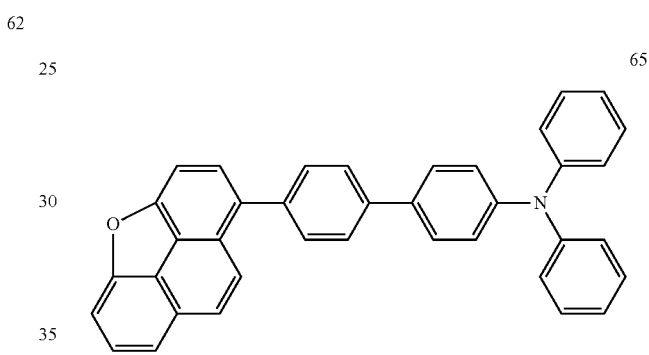
66
67
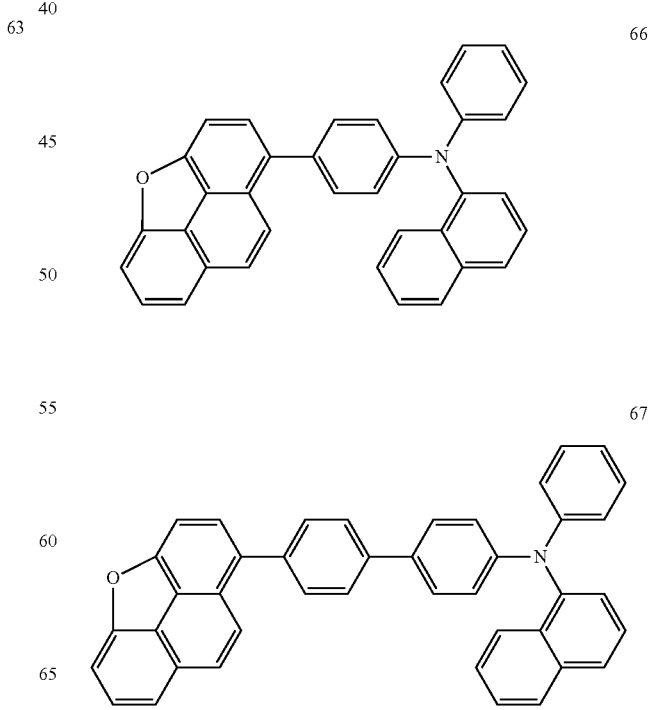

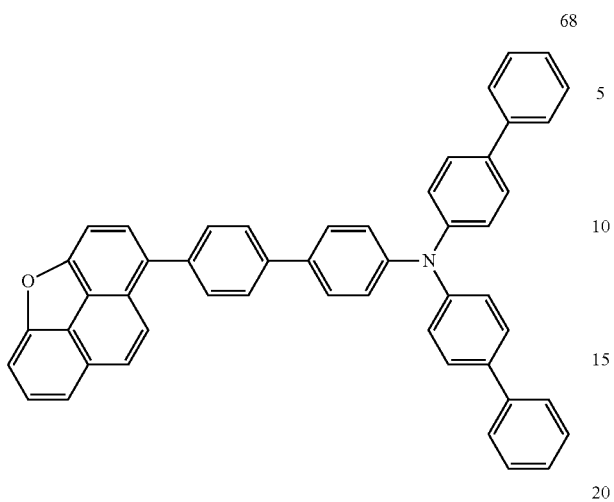
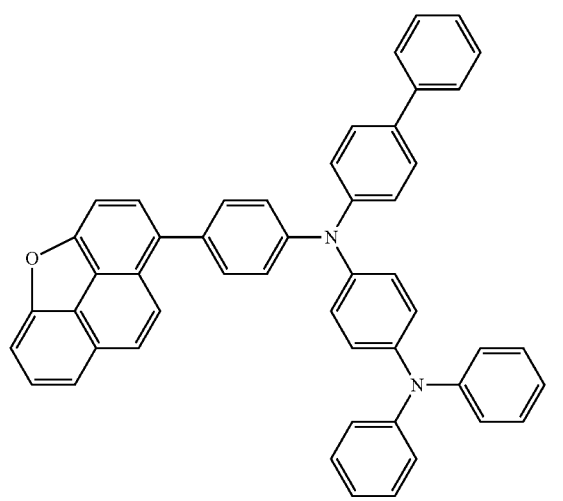
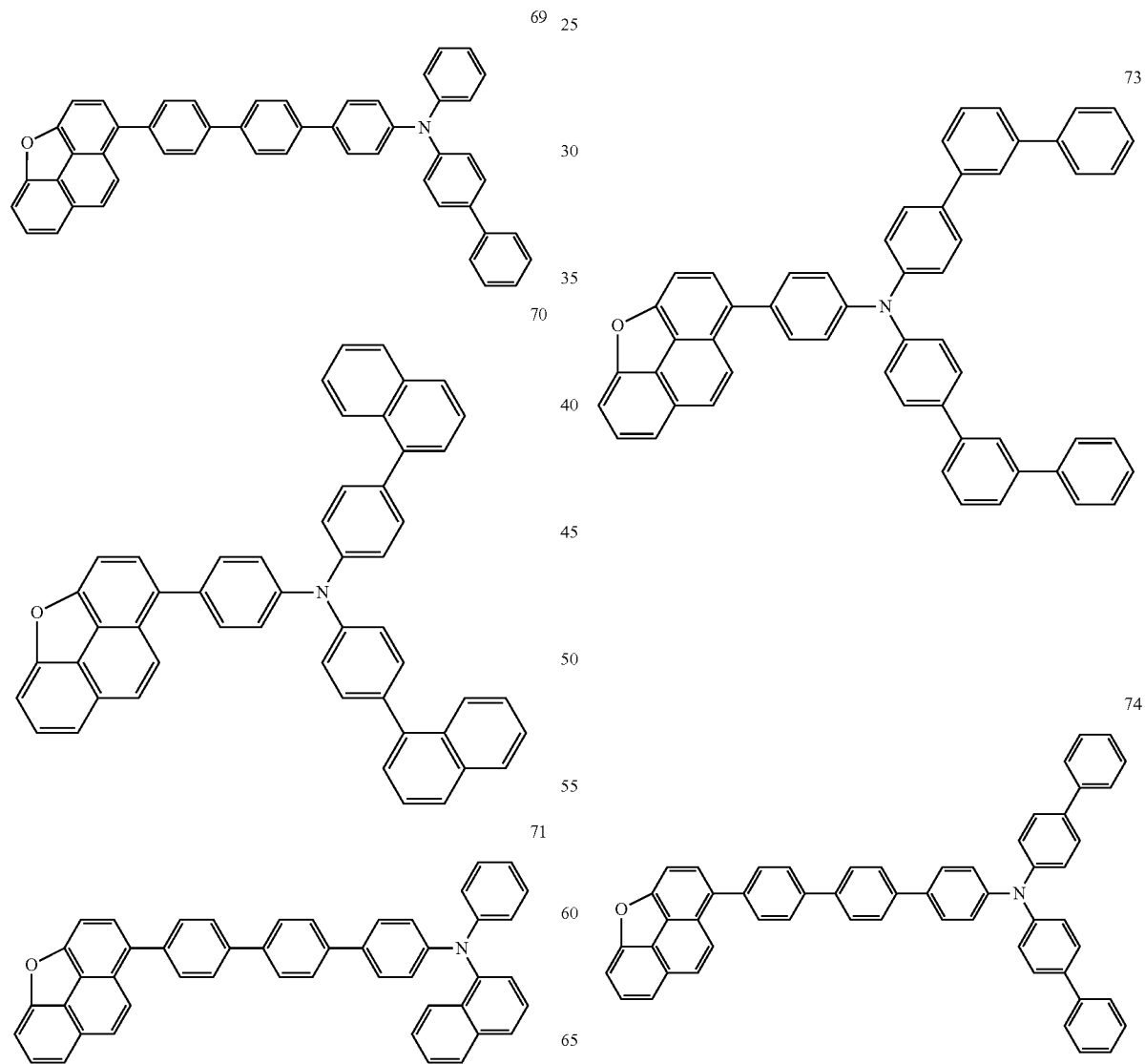

141
-continued
75
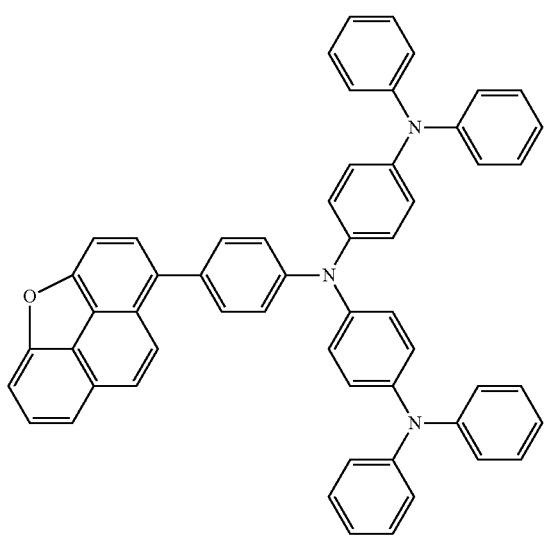
76
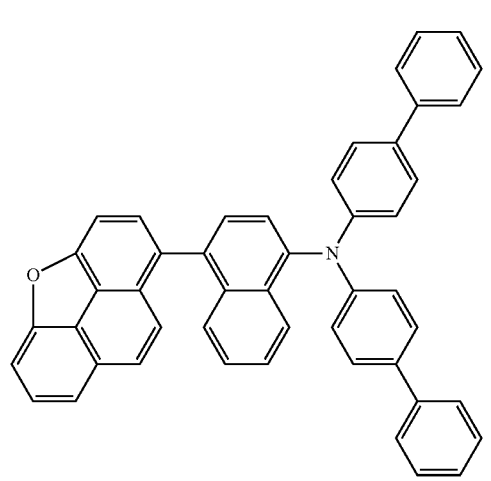
77
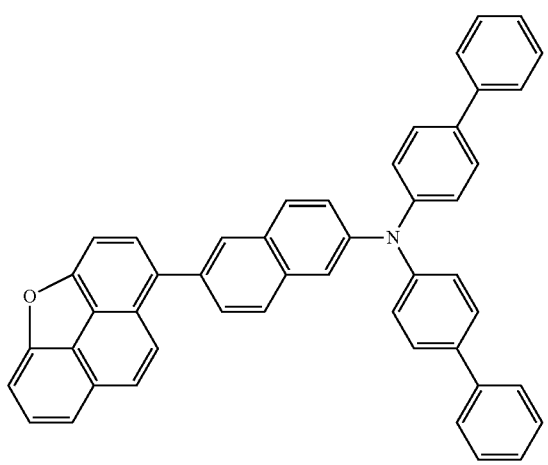
142
-continued
78
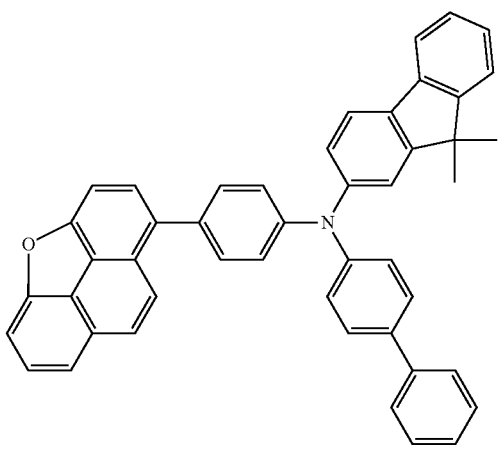
79
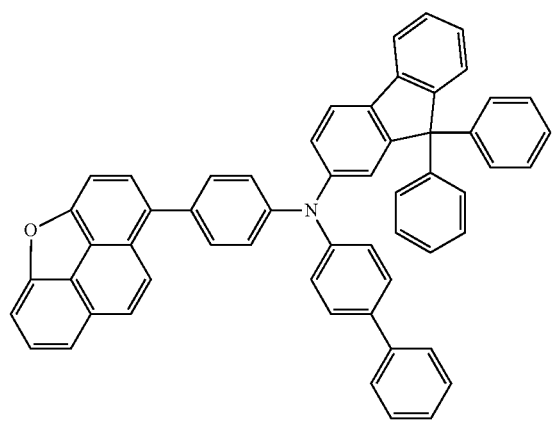
80
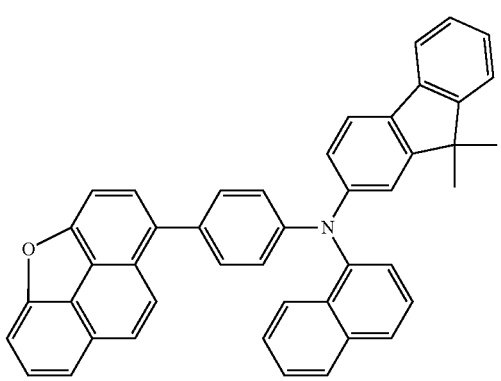

143
-continued
81
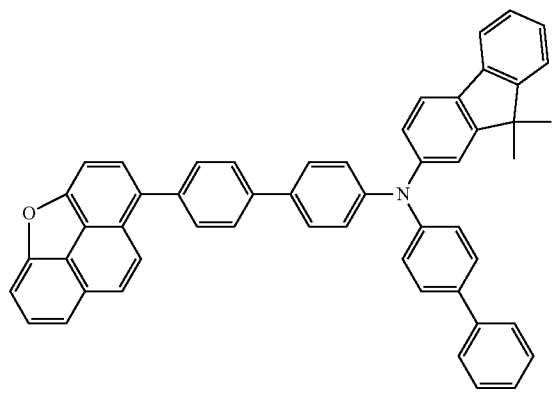
82
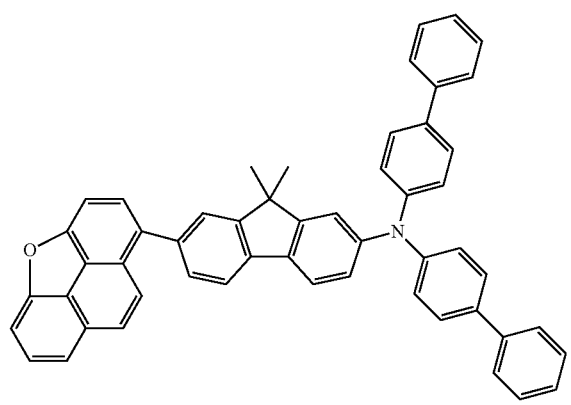
83
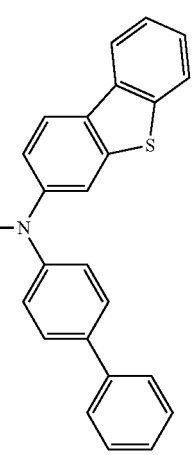
144
-continued
84
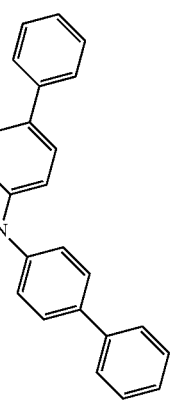
85
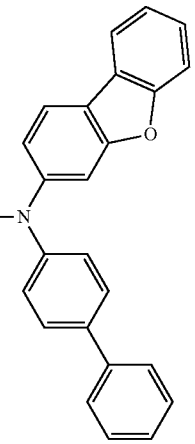
86
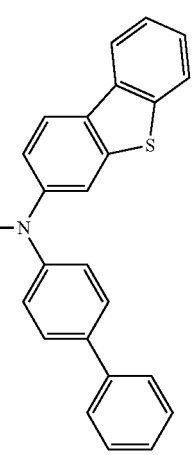

87

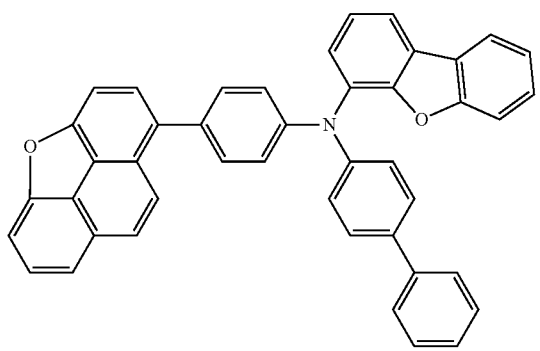

88

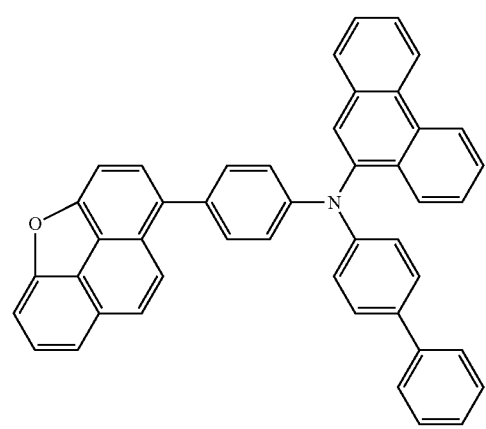

89

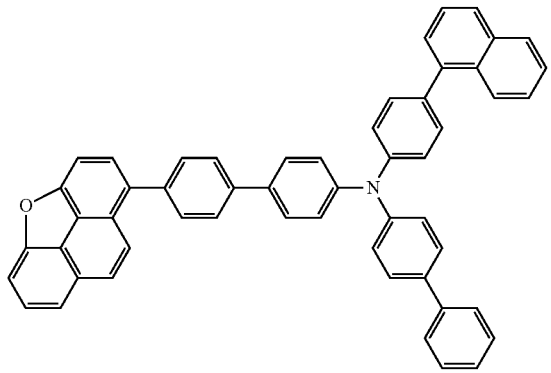

90

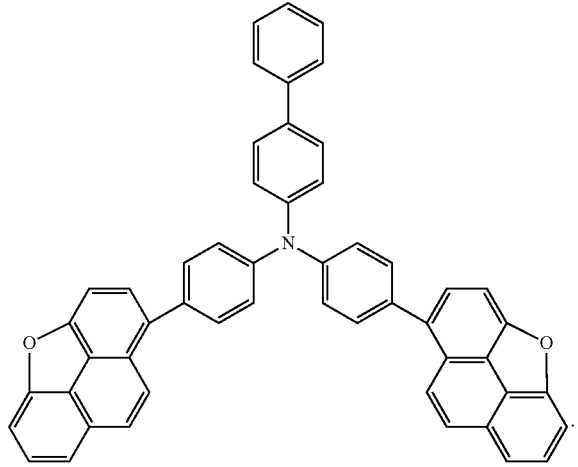

11. The organic light-emitting device as claimed in claim 1, wherein the hole transport region includes a charge-generating material.

12. The organic light-emitting device as claimed in claim 11, wherein the charge-generating material includes a p-dopant.

13. The organic light-emitting device as claimed in claim 1, wherein the electron transport region includes a metal complex.

14. The organic light-emitting device as claimed in claim 1, wherein the electron transport region includes ET-D1 or ET-D2:

ET-D1

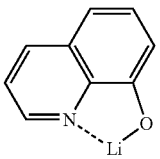

ET-D2

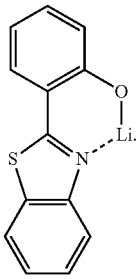

15. A display apparatus, comprising:
a thin film transistor, the thin film transistor including a source electrode and a drain electrode; and
the organic light-emitting device as claimed in claim 1, wherein the first electrode of the organic light-emitting device is electrically connected to the source electrode or the drain electrode of the thin film transistor.

* * * * *